United States Patent
D'Acosta et al.

(10) Patent No.: US 12,195,416 B2
(45) Date of Patent: *Jan. 14, 2025

(54) PROCESS FOR CONVERTING C2—C5 HYDROCARBONS TO GASOLINE AND DIESEL FUEL BLENDSTOCKS

(71) Applicant: Swift Fuels, LLC, West Lafayette, IN (US)

(72) Inventors: Chris D'Acosta, West Lafayette, IN (US); Jeffery Miller, Naperville, IL (US); Kurtis Sluss, Westfield, IN (US); Benjamin Wegenhart, West Lafayette, IN (US)

(73) Assignee: SWIFT FUELS, LLC, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/966,232

(22) Filed: Oct. 14, 2022

(65) Prior Publication Data
US 2023/0106548 A1   Apr. 6, 2023

Related U.S. Application Data

(63) Continuation of application No. 17/219,345, filed on Mar. 31, 2021, now abandoned.
(Continued)

(51) Int. Cl.
C07C 2/12 (2006.01)
C07C 5/327 (2006.01)
C10G 57/02 (2006.01)

(52) U.S. Cl.
CPC ............. C07C 2/12 (2013.01); C07C 5/327 (2013.01)

(58) Field of Classification Search
CPC .. C07C 2/12; C07C 5/32; C07C 5/327; C10G 57/02
See application file for complete search history.

(56) References Cited

U.S. PATENT DOCUMENTS

| | | |
|---|---|---|
| 3,119,883 A | 1/1964 | Kluksdahl |
| 3,579,601 A | 5/1971 | Kilven |

(Continued)

FOREIGN PATENT DOCUMENTS

| | | |
|---|---|---|
| EP | 0 311 310 B1 | 5/1992 |
| KR | 10-2012-0134192 | 12/2012 |

(Continued)

OTHER PUBLICATIONS

Catalytic Dewaxing, Shell, https://www.shell.com/business-customers/global-solutions/industry-focus/catalytic-dewaxing.html, Accessed Apr. 25, 2018.

(Continued)

*Primary Examiner* — Youngsul Jeong
*Assistant Examiner* — Jason Y Chong
(74) *Attorney, Agent, or Firm* — Woodard, Emhardt, Henry, Reeves & Wagner, LLP

(57) ABSTRACT

A process for converting C2-5 alkanes to higher value C5-24 hydrocarbon fuels and blendstocks. The C2-5 alkanes are converted to olefins by thermal olefination, without the use of a dehydrogenation catalyst and without the use of steam. The product olefins are fed to an oligomerization reactor containing a zeolite catalyst to crack, oligomerize and cyclize the olens to the fuel products which are then recovered. Optionally, hydrogen and methane are removed from the product olefin stream prior to oligomerization. Further optionally, C2-5 alkanes are removed from the product olefin stream prior to oligomerization.

7 Claims, 23 Drawing Sheets

Related U.S. Application Data

(60) Provisional application No. 63/091,644, filed on Oct. 14, 2020, provisional application No. 63/068,457, filed on Aug. 21, 2020, provisional application No. 63/060,835, filed on Aug. 4, 2020, provisional application No. 63/042,305, filed on Jun. 22, 2020, provisional application No. 63/002,887, filed on Mar. 31, 2020.

(56) References Cited

U.S. PATENT DOCUMENTS

| | | |
|---|---|---|
| 3,714,023 A | 1/1973 | Stine |
| 3,760,024 A | 9/1973 | Cattanach |
| 3,770,614 A | 11/1973 | Graven |
| 3,960,978 A | 6/1976 | Givens et al. |
| 4,100,218 A | 7/1978 | Chen et al. |
| 4,293,722 A | 10/1981 | Ward et al. |
| 4,304,948 A | 12/1981 | Vora et al. |
| 4,499,055 A | 2/1985 | DiNicolantonio et al. |
| 4,542,247 A | 9/1985 | Chang et al. |
| 4,753,720 A | 6/1988 | Morrison |
| 4,762,958 A | 8/1988 | Martens et al. |
| 4,780,196 A | 10/1988 | Alagy et al. |
| 4,827,076 A | 5/1989 | Kokayeff et al. |
| 4,929,797 A | 5/1990 | Yamaguchi et al. |
| 5,082,983 A | 1/1992 | Breckenridge et al. |
| 5,162,599 A | 11/1992 | Matturro et al. |
| 5,326,463 A | 7/1994 | Fletcher et al. |
| 5,407,559 A | 4/1995 | Degnan et al. |
| 5,435,906 A | 7/1995 | Johnson et al. |
| 5,523,502 A | 6/1996 | Rubin |
| 5,856,604 A | 1/1999 | Stine et al. |
| 6,897,345 B2 | 5/2005 | Marchionna et al. |
| 7,319,179 B2 | 1/2008 | Nieto et al. |
| 7,956,227 B2 | 6/2011 | Randolph et al. |
| 9,266,036 B2 | 2/2016 | Luebke et al. |
| 9,731,270 B2 * | 8/2017 | Yao .................. C10G 50/00 |
| 9,873,654 B2 | 1/2018 | Oda et al. |
| 2008/0177177 A1 | 7/2008 | Aoki et al. |
| 2008/0269536 A1 | 10/2008 | Crone et al. |
| 2015/0157998 A1 | 6/2015 | Luebke et al. |
| 2016/0176781 A1 | 6/2016 | Hershkowitz et al. |
| 2016/0362351 A1 | 12/2016 | Nagaki et al. |
| 2017/0247302 A1 | 8/2017 | Nielsen et al. |
| 2021/0077982 A1 | 3/2021 | Kim et al. |

FOREIGN PATENT DOCUMENTS

| | | |
|---|---|---|
| WO | WO 2017/198546 A1 | 11/2017 |
| WO | WO 2019/051101 A1 | 3/2019 |

OTHER PUBLICATIONS

J. A. Dutton, Catalytic Dewaxing, Penn State University; FSC 432, https://www.e-education.psu.edu/fsc432/content/catalytic-dewaxing, Accessed Apr. 25, 2018.

R. A. Rakosczy, P. M. Morse, Consider catalytic dewaxing as a tool to improve diesel cold-flow properties, Hydrocarbon Processing, Jul. 2013.

Zhao, X. Characterization of Modified Nanoscale ZSM-5 Catalyst and Its Application in FCC Gasoline Upgrading Process, Energy & Fuels, vol. 20 (May 12, 2006) pp. 1388-1391.

* cited by examiner

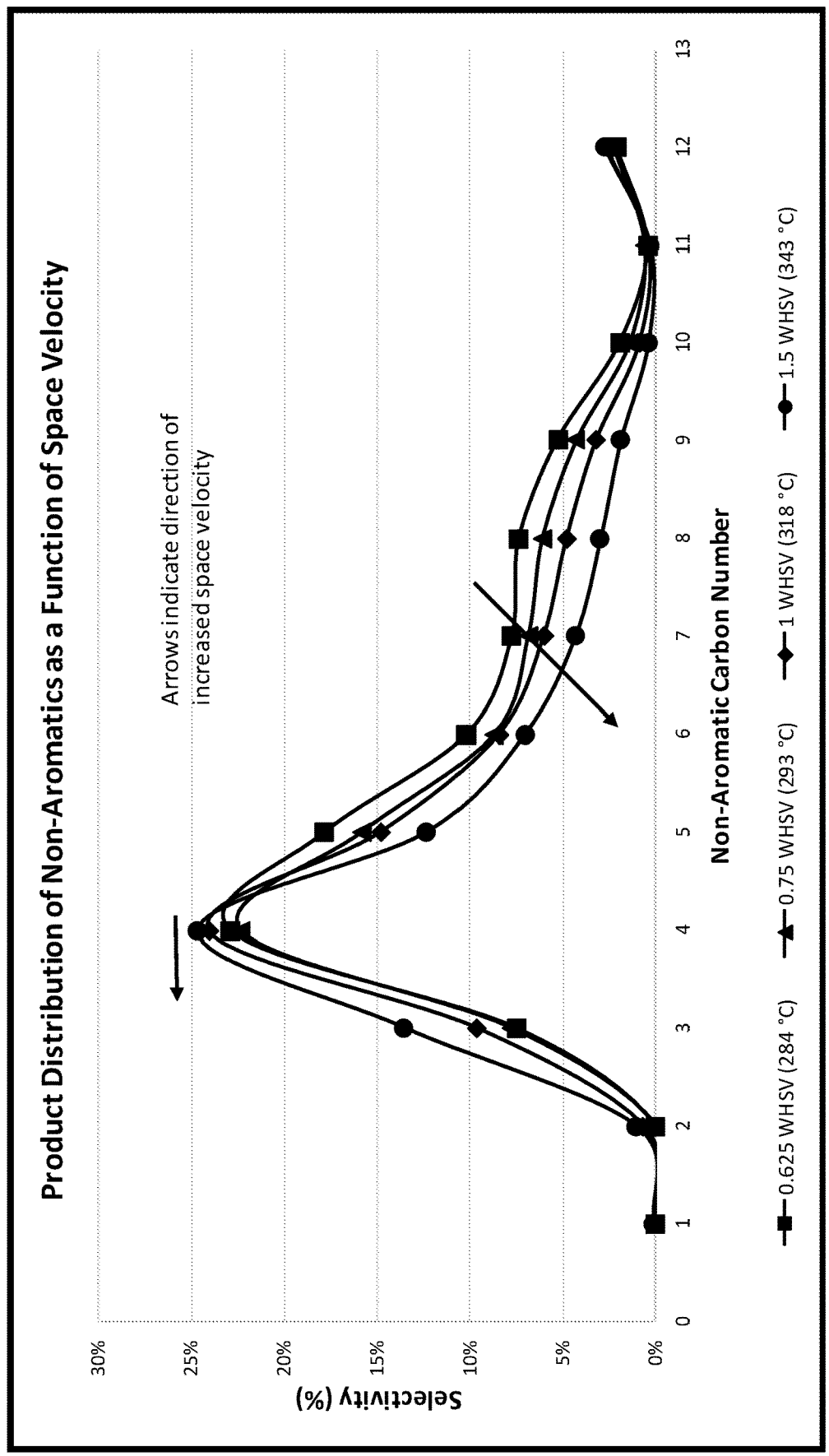
FIG. 5A (Impact of Δ WHSV)

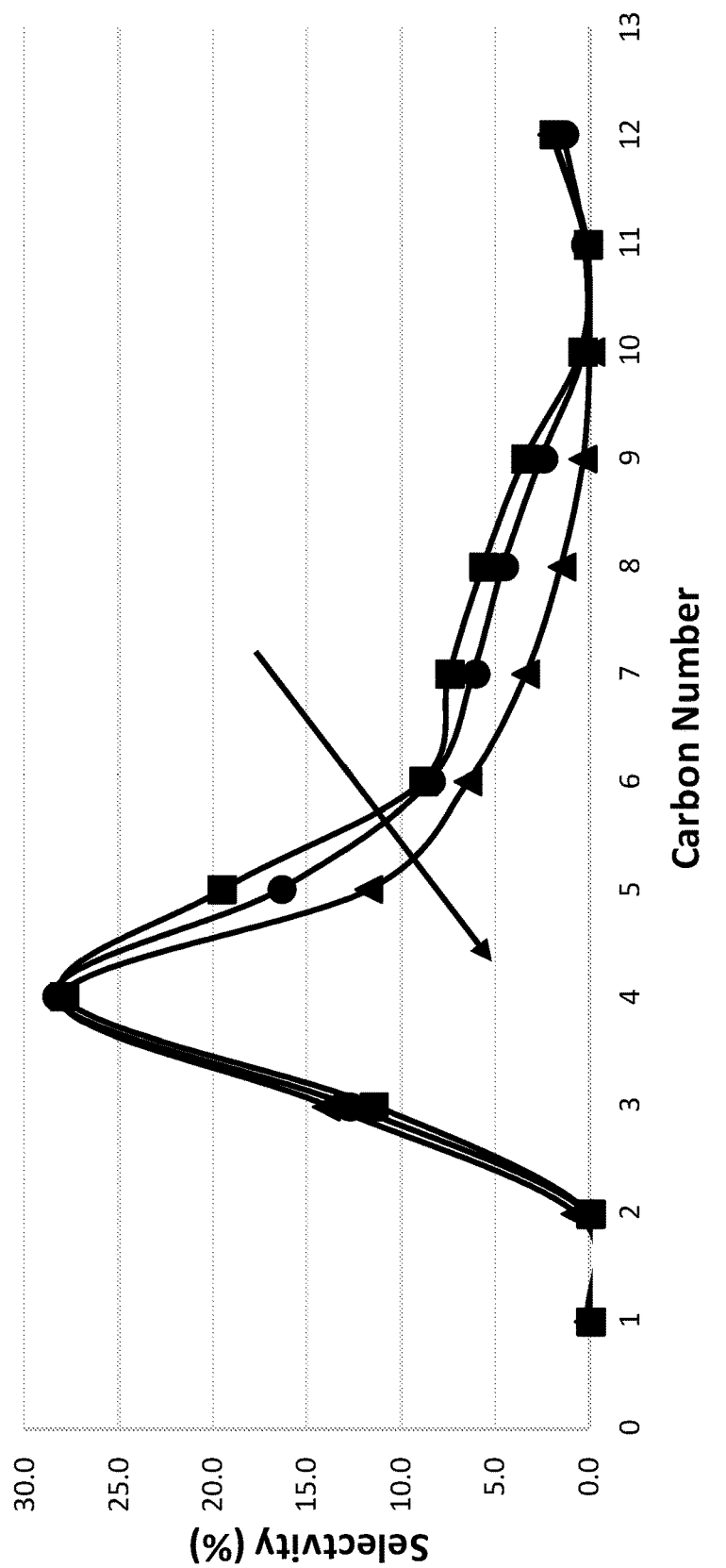
FIG. 5B (Impact of Δ°C)

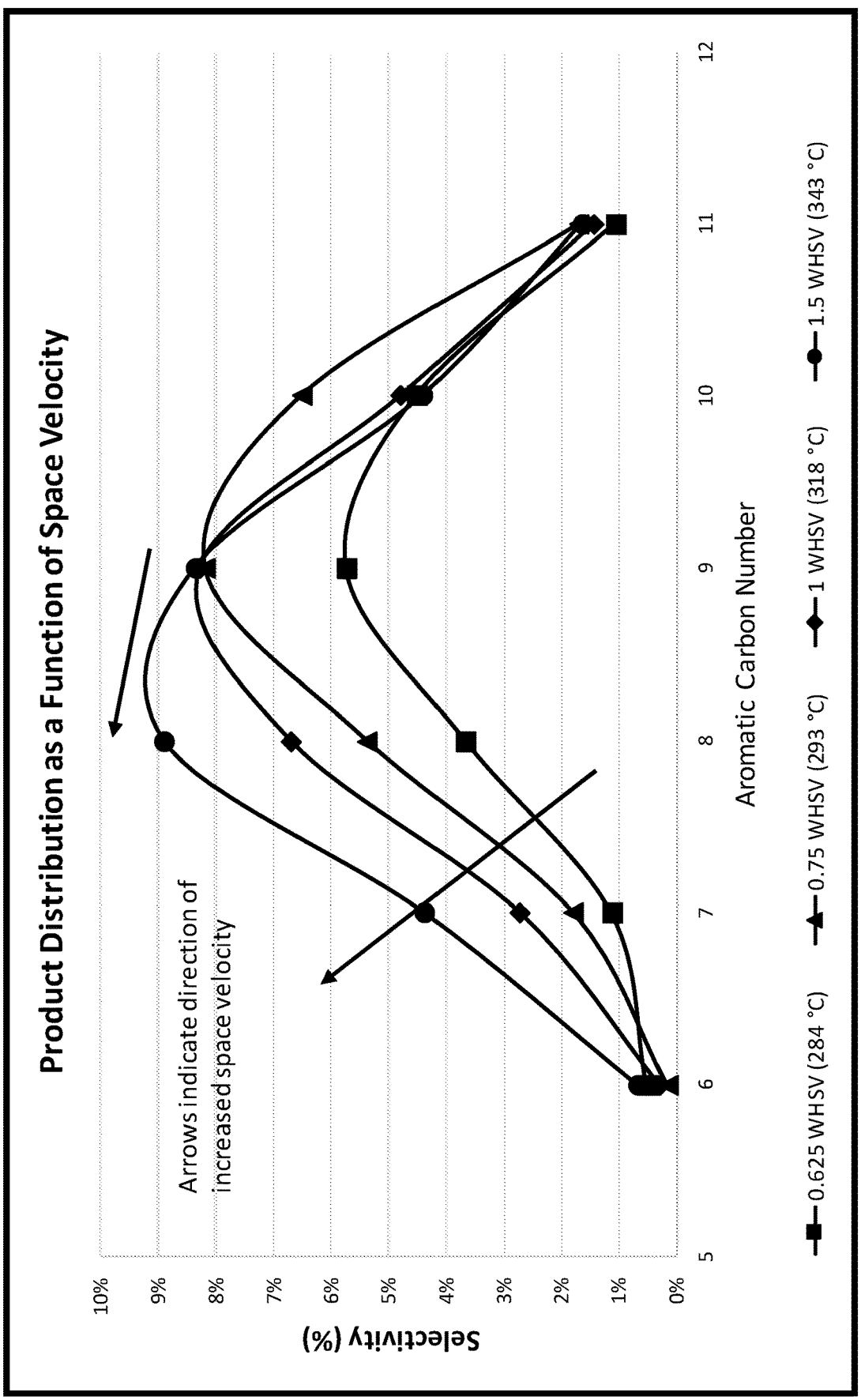
FIG. 6A (Impact of Δ WHSV)

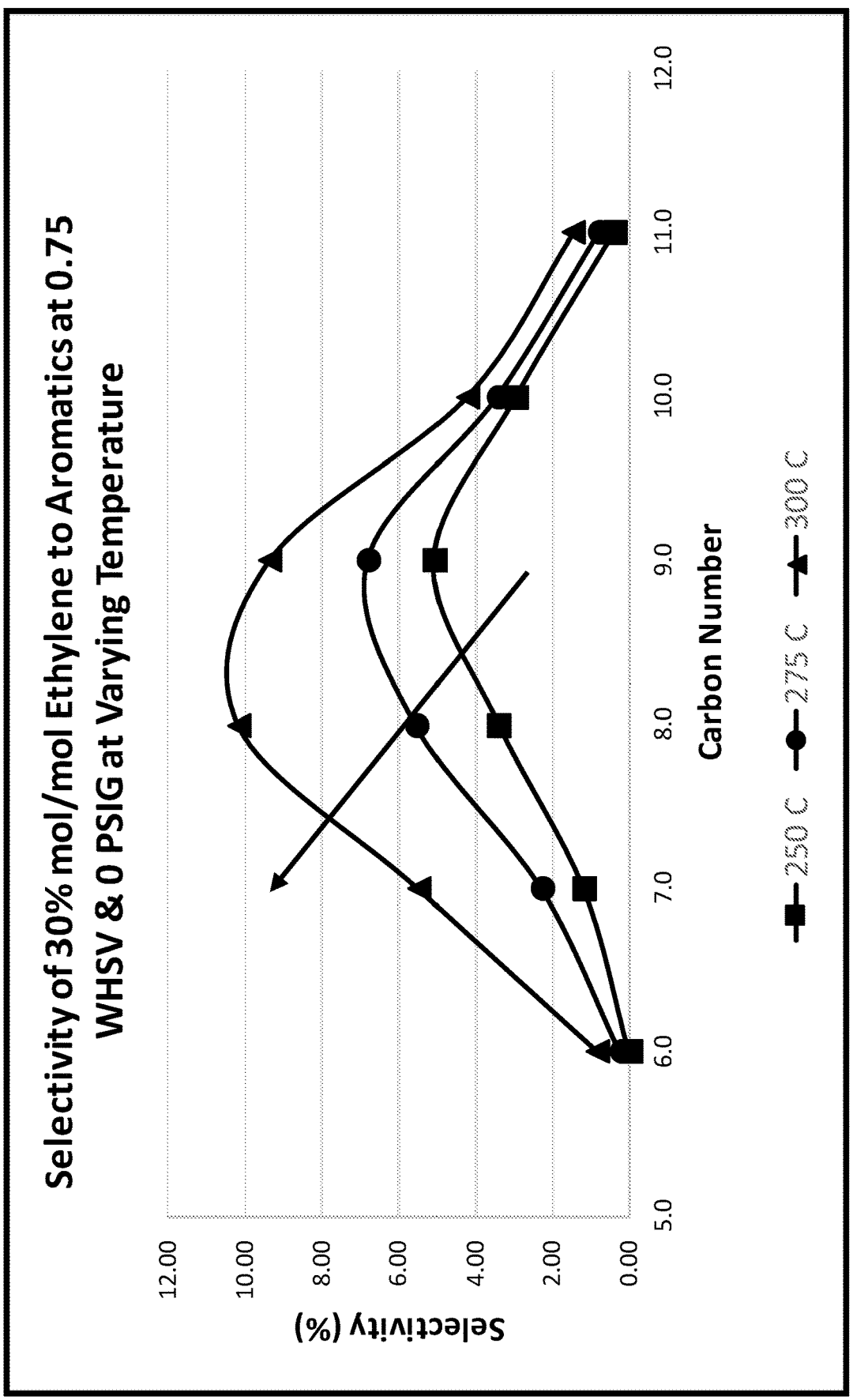
FIG. 6B (Impact of Δ°C)

PROCESS FOR CONVERTING C2—C5 HYDROCARBONS TO GASOLINE AND DIESEL FUEL BLENDSTOCKS

FIELD

The field of this invention is the low-cost production of performance-grade gasoline and distillate fuel products from C2-C5 alkane-rich light hydrocarbon feedstreams. The field more particularly relates to a specialized dry-heat "Thermal Olefination" reaction converting C2-C5 alkanes to alkenes and subsequently uses a controlled zeolite-catalytic reaction or sequence of reactions to crack, oligomerize, dimerize, trimerize, couple and/or cyclize the alkenes to form fuel formulations and blendstocks. A particular application of the invention is in the tailored derivation of performance-grade fuels and fuel blendstocks from readily-available, lower-value, hydrocarbon streams.

BACKGROUND

While the total U.S. demand for gasoline is steady or in a small level of decline, there is an increasing demand for premium gasoline blendstocks to meet the needs of new, more efficient, higher-compression spark-ignited automotive engines. There is also an increasing demand of high-performance, ultra-low sulfur, diesel fuel blendstocks with high cetane values and effective cold-temperature flowability properties used in compression-ignition diesel engines and gas turbine engines. These demands exist while surplus light hydrocarbons are stranded in certain markets without supply-chain options, despite being available from midstream, refinery and petrochemical facilities for transformation to fuel grade products.

According to the US Energy Information Administration (EIA), sources of natural gas and gas liquids in the midstream industry are abundant across the nation. See, for example, Table 1. The EIA recently estimated that the total production of C2+ light hydrocarbon gases (NGL's) on a global scale is 7.8 million barrels per day. Note that the portrayal of NGL volumes in the US may under-report rejected ethane sold with methane. Any separation of natural gas from natural gas liquids, e.g. via de-methanization, leaves an alkane-rich admixture of light hydrocarbon compounds, typically C2-C5+ natural gas liquids (NGL's). These may undergo further separations, e.g., de-ethanization, de-propanization, de-butanization of gases and liquids. This invention particularly targets any C2-C5 alkane rich source of NGL's (preferably NGL's without ethane rejection), or similar industrial gases comprising such light hydrocarbons, to transform alkane-rich feedstreams to high-value fuel products, thereby avoiding the need for such C2, C3, C4 separations.

TABLE 1

| US GAS PLANT PRODUCTION | 2-YEAR AVG. (BBL/DAY) |
| --- | --- |
| ETHANE | 1,577,870 |
| PROPANE | 1,323,455 |
| n-BUTANE | 340,604 |
| iso-BUTANE | 370,782 |
| PENTANES+ | 478,112 |

The petrochemical industry, a major consumer of ethane and propane, uses extremely complex, high-precision, and capital-intensive methods to separate and purify chemical grade compounds such as ethylene and propylene. For example, conversion of propane to propylene, or ethane to ethylene, requires cryogenic separation (−100° C.) followed by ultrapure, dry, non-contaminated hydrogeneration processing to eliminate very-close boiling molecules (e.g., butadiene, propyne, acetylene) that can be highly reactive to chemical processing and/or poison polymerization catalysts. None of these are a concern for the process of this invention.

SUMMARY

The invention comprises a process of thermal and chemical reactions which provide a high-conversion of alkane-rich C2-C5 hydrocarbon feedstreams that contain ethane, propane, butanes, or pentanes, or any admixture thereof, to performance-grade gasoline and distillate fuel products, and aromatic hydrocarbons. The process includes a specialized method of converting certain alkane feeds to olefins by way of a low-cost, non-catalytic, dry-heat, alkane-to-olefin reaction called "Thermal Olefination". The process combines this Thermal Olefination reaction with subsequent cracking, oligomerization, dimerizing, trimerizing coupling, and/or cyclization reactions of olefins to fuel-grade products using zeolite catalysts. In embodiments, the process includes variations useful in the conversion of alkene-containing feedstreams.

The process can be arranged in appropriate sequences with thermal and catalytic reactors operating in parallel or in series and utilizing various recycling methods based upon feedstock characteristics, operating conditions, and desired products.

The thermal and catalytic reactors utilize innovative low-cost methods to minimize carbon build-up including the use of specialized catalytic regeneration techniques. These techniques reduce coking of the reactor and minimize deactivation of the catalysts.

The liquid fuel products produced from the process can be specifically targeted by operating conditions and catalyst choices to yield any desired range of $C_4$ to $C_{12}$ gasoline compounds (i.e., high octane paraffins, olefins and aromatics), or to yield $C_9$ to $C_{16+}$ high-performance middle distillate compounds (e.g., containing low-ppm sulfur, high cetane, low pour point) for use in ultra-low-sulfur diesel fuel that achieve pre-specified fuel performance targets.

The process also accommodates any alkene-containing C2-C5 light hydrocarbon feedstreams that contain ethene, propene, butenes or pentenes, or any admixture thereof, which are convertible to fuel blendstocks using the same thermal and catalytic process and reactions albeit sequenced based upon the characteristics of the collective feedstream constituents as outlined in this invention.

Further objects and advantages will be apparent from the description which follows.

BRIEF DESCRIPTION OF THE DRAWINGS

FIGS. 5A and 5B are graphs showing selectivity of product distribution of aliphatics as a function of space velocity.

FIGS. 6A and 6B are graphs showing selectivity of product distribution of aliphatics as a function of space velocity.

DESCRIPTION

Figure 1:
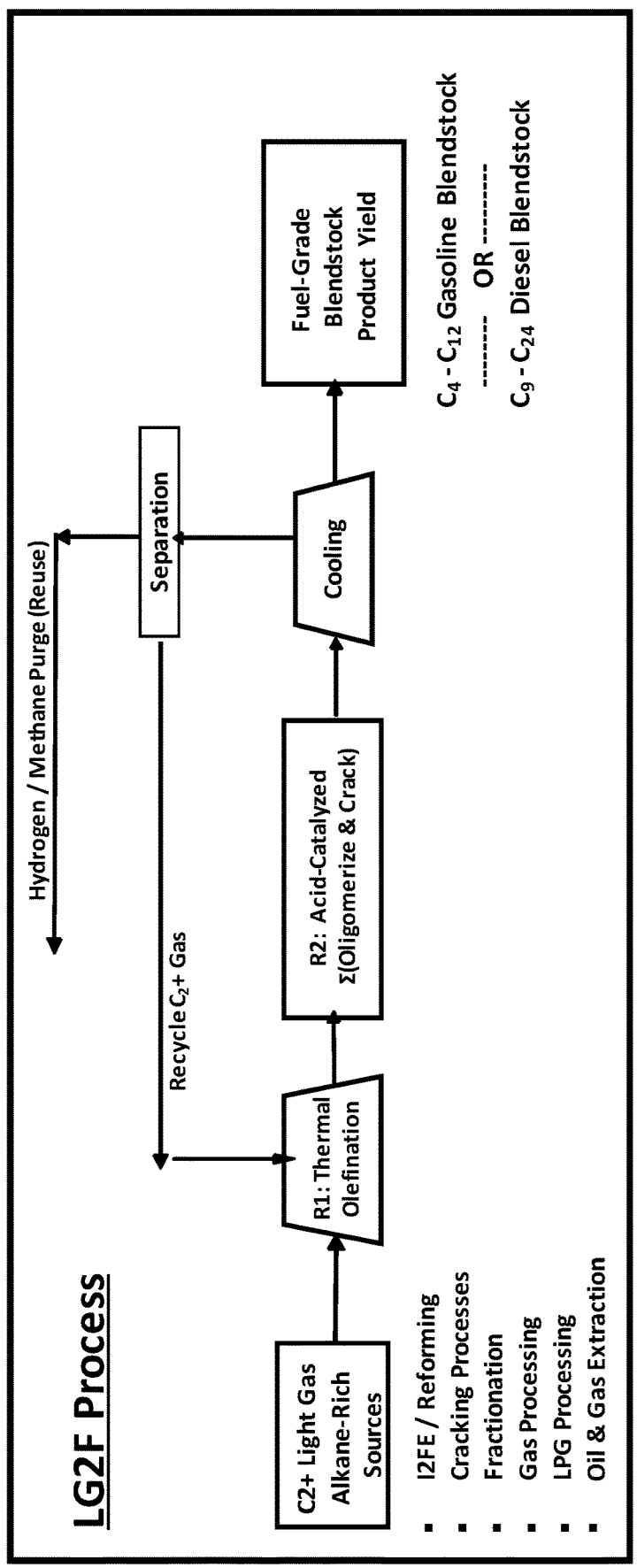
FIG. 1 is a schematic showing the process flow and system components of the conversion method and system of the present invention.

For the purpose of promoting an understanding of the principles of the invention, reference will now be made to the embodiments illustrated herein and specific language will be used to describe the same. It will nevertheless be understood that no limitation of the scope of the invention is thereby intended. Any processing alternatives, sequencing options, alterations and/or further modifications in the described embodiments, and any further applications of the principles of the invention as described herein are contemplated as would normally occur to one skilled in the art to which the invention relates. Embodiments of the invention are shown in detail, but it will be apparent to those skilled in the relevant art that some features that are not relevant to the present invention may not be shown for the sake of clarity. All percentages used herein are weight percentages, unless indicated otherwise.

An aspect of this disclosure, referred to herein generally as the Light Gas to Fuel Process, or "LG2F Process", converts alkane-rich feedstreams of hydrocarbons comprising 2-5 carbons, or any admixture of $C_{2-5}$ hydrocarbon compounds, to selected ranges of $C_4$ to $C_{16+}$ fuel grade hydrocarbons. The process includes a non-catalytic dry-heat Thermal Olefination reaction using R1, followed by an acid-catalyzed reaction using specific zeolite catalysts in R2 (which may vary in different embodiments) which chemically create a controlled series of cracking, oligomerizing, dimerizing, trimerizing, coupling, and/or cyclizing reactions. The process may be performed in a variety of sequences using single or multi-bed reactors subject to the feedstream characteristics, operating parameters and targeted products. As used herein, the term LG2F Process includes all processes, and corresponding systems, coming within the scope of the present disclosure.

This invention utilizes a Thermal Olefination reactor producing a series of complex high-temperature reactions that may include non-catalytic dehydrogenation and cracking reactions to upgrade any source of light hydrocarbon gas phase alkane-rich compounds (i.e., in preferred embodiments >90% alkanes) to produce an olefin-containing light gas effluent stream. These lower-boiling olefin compounds are then transformed to produce a spectrum of longer alkanes and/or alkenes and/or aromatics, by using zeolite catalysts in a temperature and pressure controlled catalytic reactor(s). This complete thermal and catalytic transformation of light alkane-rich gases results in unique, higher-valued longer-chain hydrocarbon streams which can be condensed into liquid products including targeted high-octane compounds for use as gasoline blendstocks or longer-chain, high-cetane compounds for use as diesel blendstocks.

The LG2F Process is extremely efficient and does not require complex multi-stage distillation or fractionation columns, multi-stage cryogenic separation, or hydrogenation processing (such as those typically used for purification in the base petrochemical industry), while producing a diverse molecular spectrum across selected $C_4$ to $C_{16+}$ blendstocks with targeted performance characteristics ideal for transportation fuels with up to 60% less capital investment.

The LG2F Process employs a Thermal Olefination technique to avoid traditional catalytic dehydrogenation and/or the use of steam cracking, while leveraging a light-gas recycle system to maximize finished product yields of targeted high-performance fuel products.

The LG2F reactor systems may utilize unique reactor and catalytic regeneration/cleansing processes to eliminate the need for steam cracking, boilers and in-line water separation processes. An automated, in-line regeneration process allows operability of the reactors to be extended preferably in excess of 10 years for R1 thermal activation and preferably in excess of ~4 years for efficient R2 catalyst activity levels including R2 and R2L).

The LG2F process can also convert de-methanized gas streams and industrial alkane-rich off-gas compounds to liquid fuels, and thereby minimize production losses attributed to low-value off-gas compounds. The LG2F process can receive methane of any amount in the alkane-rich feedstream, but since it is virtually inert, the inclusion of methane in LG2F is commercially preferably at equilibrium from 5% to 25% (wt) to serve both as a diluent and to control heat management. In some aspects, C3+ or C4+ or C5+ gas streams can be easily condensed and removed to increase the concentration of C1/C2+ alkanes to feed the R1 reaction. Due to market/location imbalances, compounds such as methane vs. NGL's, or even various grades of gasoline or diesel, may have economic values which vary, allowing location arbitrage introducing an additional factor in assessing the optimal configuration of feed sources, operating conditions, and market dynamics impacting targeted product and byproduct portfolios. The availability of light hydrocarbon feedstreams (e.g., whether alkane-rich or alkene-containing) and the appropriate sequencing of the Thermal Olefination and catalytic processes of this invention are tailored to yield high-octane gasoline blendstocks or high cetane diesel fuel blendstocks or aromatic hydrocarbons to meet specific market-based, performance-based, and regulatory-driven fuel specification requirements.

Overview

The present disclosure is based upon a unique and efficient process for the conversion of C2+ light paraffins into performance-grade fuel components suitable for the transportation fuels market. Selected alkane-rich feeds undergo Thermal Olefination reactions in a first reactor (R1), transforming the light paraffin compounds to olefins. The olefins from the Thermal Olefination reactions are then catalytically transformed via a specified zeolite catalyst in a second reactor or sequence of reactors (R2) into high-performance fuel-grade blendstock. This combination of the specific Thermal Olefination and catalytic conversion reactions is referred to herein as the LG2F Process. This process converts light hydrocarbon gases into high-grade transportation fuels and fuel blendstocks that span select ranges of hydrocarbon compounds possessing targeted fuel compositions and performance characteristics.

Industry Need

Due to the increased abundance of C2-C5 light hydrocarbons and shale gas production on a global scale there is a surplus supply and growing market dislocation of light hydrocarbons (also known as NGL's) with limited pathways to petrochemical markets (e.g. ethane crackers). Accordingly, there is growing interest in converting and upgrading such lower value light hydrocarbons (particularly the lighter ethane and ethane/propane mixtures) using R1 Thermal Olefination with non-catalytic dry heat and R2 with zeolites in the absence of steam, cryogenics and heavy fractionation to produce selected higher-value C6-C24+ fuel range components as performance-ready consumable fuel products leveraging the existing transportation fuels supply chain. This requires that fuel components be produced to match critical performance specifications for gasoline, middle distillate and diesel fuels, etc. such that they can be blended into existing supply chain pathways.

Solution

The LG2F process provides an efficient, low-capital-intensive technique to produce any number of hydrocarbon fuels or fuels blendstocks in the gasoline and middle distillate spectrum that are capable of meeting fuel performance criteria set by the industry. This allows the fuels produced by this invention to be compatible with fuels in the existing supply chain and available for immediate blending primarily with transportation fuels, or as petrochemical feedstocks or other boutique blends with some added commercial value.

The basic LG2F Process is exemplified in FIG. 1. A C2-5 light gas alkane-rich feedstream is directed to Thermal Olefination reactor (R1), wherein C2-5 Alkanes are converted into olefins. Cracking, oligomerization and/or aromatic cyclization take place in a second, catalytic conversion reactor (R2). Upon completion of the catalytic process, the resulting hydrocarbon stream undergoes any appropriate steps to liquify the products (e.g. cooling, compressing, quenching, partially condensing, and flashing) for liquid recovery of the fuel-grade blendstock product. Any uncondensed gases and vapors not targeted for fuel grade products are available for recycling. At this point, some portion of the hydrogen and methane in the cooled light gases from the catalytic reactor are separated from the C2+ gases for commercial reuse, and the remaining collection of gases and vapors may be recycled to the Thermal Olefination reactor.

Fuel-grade hydrocarbons, with selected ranges of $C_4$-$C_{12}$ blendstock for gasoline and $C_9$-$C_{24+}$ blendstock for diesel fuel are recovered. As a result, select $C_{2+}$ light alkanes are transformed to any range of $C_4$ to $C_{16+}$ hydrocarbon constituents for use in various transportation fuels, with methane and hydrogen as byproducts. Another feature of the light gas transformation is the creation of aromatic hydrocarbons which add energy density and bring a higher-octane value to the gasoline blendstock and contribute to thermal stability and cold-flow properties for diesel fuels. Optionally, the aromatic hydrocarbons are recoverable as low-cost petrochemical feedstock, e.g. for BTX operations, as naphtha supply constraints gradually increase pushing aromatic prices higher.

C2-5 Alkane Feedstreams

The Thermal Olefination reactor receives and processes alkanes including 2-5 carbon atoms, namely, ethane, propane, butane and/or pentane. As used herein, the term "C2-5 Alkane" is used to refer to alkanes having specifically from 2 to 5 carbon atoms. The term "Feedstream" refers to a reactor feed not including any recycle component. The term "C2-5 Alkane Feedstream" refers to a Feedstream comprising any single compound or admixture of C2-5 alkanes. For example, a typical C2-5 Alkane Feedstream may include ethane, propane, n-butane, iso-butane and n-pentane. As described hereafter, in a preferred aspect the C2-5 Alkane Feedstream is sourced as an effluent stream from existing commercial operations. It may have been the subject of pretreatments, and it may also be formed from the combination of more than one feed source. Depending upon the feedstock source, these light hydrocarbon feedstreams may be treated to remove unwanted trace compounds that can otherwise contaminate process streams or corrode equipment.

The LG2F Process specifically uses a C2-5 Alkane Feedstream which is "alkane-rich", meaning that in a typical embodiment at least 50% of the Feedstream comprises C2-5 Alkanes, and in the preferred embodiment at least 90% of the Feedstream comprises C2-5 Alkanes. In another aspect, the alkane-rich, C2-5 Alkane Feedstream includes at least 95%, and preferably at least 98%, C2-5 Alkanes. The C2-C5 Alkane Feedstream in certain embodiments may then be merged with LG2F recycled compounds, including up to about 25-40% wt. inert compounds (e.g. methane, hydrogen, etc.) operating as diluents or unreactive compounds, which once merged are fed into the R1 Thermal Olefination Reactor.

In particular embodiments, the C2-5 Alkane component is a specific subset of all C2-5 Alkanes. For example, certain embodiments utilize a C2-5 Alkane Feedstream constituting a single C2-5 Alkane, namely any one of ethane, propane, butane or pentane. In a particular aspect, the LG2F Process uses ethane as the C2-5 Alkane Feedstream. In other embodiments, the C2-5 Alkane Feedstream contains at least 90%, preferably at least 95%, and more preferably at least 98% ethane. In an alternative embodiment, the C2-5 Alkane Feedstream comprises 80-100% ethane and 0-20% propane. Ethane and propane are less expensive alkanes and there is thus a greater value in upgrading them to use in fuels. In another aspect, the C2-5 Alkane Feedstream comprises at least 90% of a mixture of ethane, propane and butane.

In particular embodiments, the upstream preparation of the C2-C5 Alkane Feedstream for use in the LG2F process may come from any appropriate raw gas feed, or stored, or processed C2-C5 light gas streams or the prior demethanization of C2-C5 light gas streams, or the deethanization of C2-C5 light gas streams, or the depropanization of C2-C5 light gas streams, or the debutanization of C2-C5 light gas streams, or any combination of related methods known to those schooled in the art of C1-C5 light gas separation technology. There may also be opportunities to modify the system requirements between the LG2F process and any upstream C1-C5 Alkane Feedstream gathering processes to manage the efficient co-usage of compression horsepower, electricity, methane as fuel gas (or as diluent), light-gas stripping/flashing, hot oil, instrument air, heat exchangers, boiler feed water, chillers, distillation methods (e.g. tray configurations, etc.), cooling or refrigeration requirements, and other related matters between the interfacing systems.

In one embodiment, a demethanizer tower is adjusted to provide a slit stream comprised of >90% wt. ethane being thereby separated from the C3+ light gas stream for use as a highly concentrated ethane source for input to the R1 Thermal Olefination process. The compression horsepower is adjusted to meet the needs of the demethanizer and the LG2F front-end process. Upon establishing an LG2F processing equilibrium, the fresh ethane stream continues thereafter with the option to merge with an existing LG2F recycle stream containing about 60%-80% unreacted C2+ alkanes and about 20-40% inert gases (e.g. methane, hydrogen). In a similar embodiment, a slit-stream method is employed to provide a >80% C2 ethane feed stream for use as a concentrated ethane source for input to the R1 Thermal Olefination process. Upon establishing a processing equilibrium, the fresh ethane stream continues thereafter with the option to merge with a the LG2F recycle stream containing additional C2+ unreacted alkanes and inert gases. In another embodiment, an ethane pipeline is employed comprising a >90% C2 ethane feed stream for use as a highly concentrated ethane source for input to the R1 Thermal Olefination process. Upon initiation of the LG2F process, an equilibrium is formed whereby the fresh ethane stream continues thereafter with the option to merge with a the LG2F recycle stream comprised of C2+ alkanes, methane and other inert gases. In another embodiment, an ethane storage facility is employed comprising a >90% C2 ethane feed stream for use as a highly concentrated ethane source for input to the R1 Thermal Olefination process. Upon initiation of the LG2F processing, an equilibrium is formed whereby the fresh ethane stream continues thereafter with the option to merge with a the LG2F recycle stream comprised of C2+ unreacted alkanes, methane and other inert gases.

Similar embodiments can be expressed for the use across a wide range of operational scenarios whereby any C2-C5 light gas mixture comprising ethane, or ethane and propane (e.g. E/P mix), or mixtures comprising ethane, propane, and butane, including higher concentrations of >20% propane and/or high concentrations of >20% butane. The proportionality of C2-C5 carbon molecules in the feedstream directly impacts the R1 Thermal Olefination processing temperature, which can be adjusted to compensate for the degree of heat needed to thermodynamically crack the carbon bond in the C2-C5 feedstream. A higher proportion of C2 ethane molecules in the feedstream requires a higher R1 operating temperature (e.g. typically 800-1050° C. at <10 atm), whereas a higher proportion of C3 propane molecules requires a milder R1 operating temperature (e.g. 650-850° C. at <10 atm), and a higher proportion of C4 butane molecules requires an even milder R1 operating temperature (e.g. 550-850° C. at <10 atm) in the Thermal Olefination reactor.

The Thermal Olefination reaction can be designed to use any combination of R1 reactors in any sequence operating at any appropriate conditions to convert alkanes to alkenes. These techniques are well known to those schooled in the art of high-temperature reactor design. The Thermal Olefination reaction does not employ or require the use of catalysts and is therefore not described as a dehydrogenation (chemical) reaction. It is instead a high-temperature thermal reaction operated without steam, catalyst or toxic chemical additives (e.g. DMDS) with or without the specially designed plating (anti-coking), carbon capture and regeneration methods outlined herein.

Other Feedstream Constituents

The typical C2-5 Alkane Feedstream contains at least 50% to 90% by weight of C2-5 Alkanes. Therefore, in certain embodiments the Feedstream includes other constituents. These other constituents may, for example, include other hydrocarbons, contaminants and inert materials.

The additional components may include other hydrocarbons. Methane may be present in the Feed Stream, particularly depending on the source. Methane is preferably kept to a low amount (preferably less than 5-20%) as it is unreactive and therefore unproductive in the LG2F Process. Controlled accumulations of methane via recycle can be productive for dispersing consumed and generated heat in the R1 and R2 reactors, respectively. In an embodiment, methane gas may be used as a diluent to sustain heat for the R1 Thermal Olefination reactor (an endothermic reaction). In a related embodiment, methane gas may be used as a diluent to disperse heat in the zeolite-catalytic R2 reactor (an exothermic reaction). In another embodiment, it is possible to utilize a membrane or other (non-distillation) gas separation unit prior to the Thermal Olefination reaction to remove unproductive quantities of methane from the feedstream for higher purity C2-C5 feedstreams. Higher alkanes may be present and can be thermally cracked in the LG2F Process, but they are also useful as gasoline constituents and there is therefore limited value in including them in the Alkane Feed Stream. Accordingly, in a similar embodiment, an option exists to capture C6+ liquids from the C2-C5 feedstream in a liquid/vapor flash drum prior to the Thermal Olefination reaction to minimize cracking of these compounds. Light hydrocarbon feedstreams with smaller quantities of alkenes and alkynes are to be avoided as they lead to low yield (making benzene and methane), and they tend to coke the R1 reactor. Note that LG2F alternatives exist to handle feedstreams with larger quantities of alkenes via use of the R2 reaction. Furthermore, R2 converts alkenes at levels greater than 90-95%. Therefore, alkenes and alkynes preferably comprise less than 5% of the R1 recycle feedstream, and more preferably less than 2%, of the C2-5 Alkane Feed Stream including once merged with the R2 recycle stream.

Figure 16:
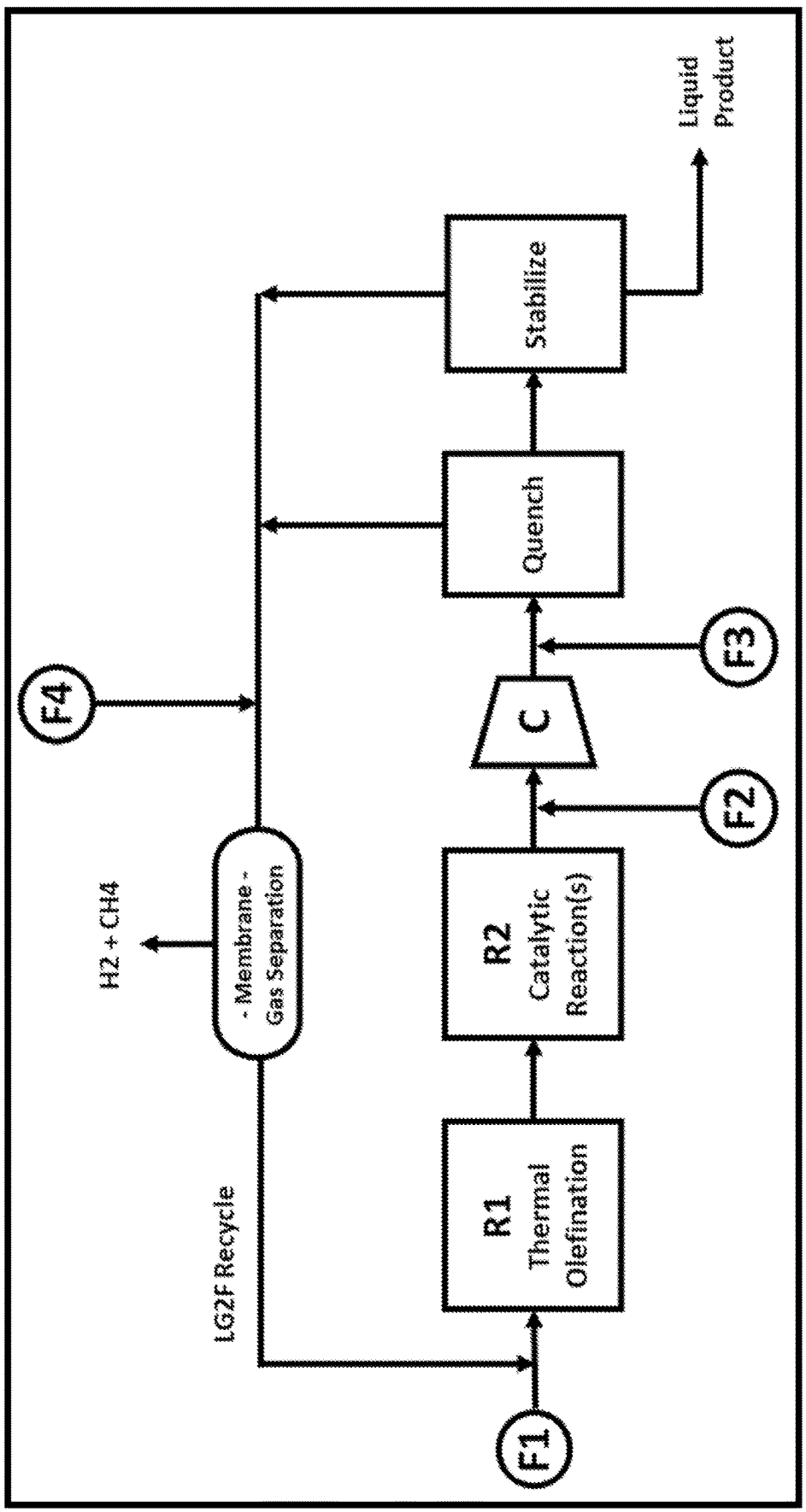
FIG. 16 is a flow diagram showing the process including four alternatives for the entry of C2-C5 alkanes into the LG2F process by way of alkane-rich feedstream options F1, F2, F3 and F4.

FIG. 16 illustrates the flexibility of the LG2F process to accommodate a wide range of light hydrocarbon feedstreams. The chart identifies four main options F1, F2, F3 and F4 that feedstreams comprised of C2-C5 alkanes may enter the LG2F process.

Using feedstream option F1, the alkane-rich feedstream would preferably be comprised of >80% (wt.) ethane prior to being combined with the LG2F recycle loop. Using feedstream option F2, the alkane-rich feedstream would preferably be comprised of >50% C3+ alkanes at low pressure. Using feedstream option F3, the alkane-rich feedstream would preferably be comprised of >50% C3+ alkanes at a pressure higher than the pressure level output from compressor C. Feedstreams F2 and F3 will undergo the liquid recovery process (quench and stabilization) of the C4+ compounds with the further option to recycle these or use these in the liquid product (depending upon the liquid product requirements). Using feedstream option F4, the alkane-rich feedstream would preferably be comprised of >20% (wt.) methane allowing some excess methane to be separated for fuel or commercial use and some to pass through recycle at equilibrium for use as diluent in the LG2F process. The LG2F process can accommodate any single feedstream option or any combination of alkane-rich feedstream options F1, F2, F3 or F4.

In the case where the available C2-C5 feedstream is alkene-rich, the LG2F process can accommodate this by feeding the C2+ alkene-rich feedstream directly into the R2 catalytic reaction and bypassing the initial Thermal Olefination reaction, as previously mentioned in this invention. It is also possible to tailor a process using an alkene-rich feed comprised of C3+ or C4+ alkenes to isolate these compounds for direct entry into the quench and stabilization process and then the resulting stream comprised of C3+ alkenes can be recycled directly into the R2 catalytic process (not depicted in Chart X1) to maximize the production of fuel grade products from alkene feedstreams. The LG2F process can accommodate these further alkene-rich alternatives, including those comprised of >20% wt. methane (as depicted in stream F4 above) which are then diverted to R2 oligomerization reaction, as long as the alkene-rich feedstreams are appropriately isolated from the alkane-rich feedstreams to be used in R1 Thermal Olefination.

In one embodiment, a C2-C5 alkane-rich feedstream preferably comprised of >50% C3+ alkanes is merged with the effluent of the R2 catalytic reactor (e.g. via F2 or F3) and processed by the liquid recovery system to remove specified C4+ liquids and separate light gases and then the C3 alkane-rich feedstream is returned via the recycle loop, but without receiving ethane from the F1 feedstream, to reenter the LG2F process via the R1 reactor configured for Propane Thermal Olefination. In another embodiment, an C2-C5 alkene-rich feedstream preferably comprised of >50% C2+ alkenes (e.g. refinery FCC intermediates) is merged with the recycling effluent of the R2 catalytic reactor (F2 or F3), then processed by the liquid recovery system to remove specified liquids and separate light gases and then returned via the recycle loop, without receiving ethane from the F1 feedstream or utilizing any Thermal Olefination, to directly enter the single or multi-step R2 catalytic oligomerization process to produce fuels. In another embodiment, an alkane-rich feedstream comprised of >20% methane enters the LG2F process by being merged with the recycling light gas effluent of the LG2F liquid recovery system (shown as feedstream F4), then together is processed by separating the H2 and methane light gases without cryogenics or fractionation, and then the light alkanes collectively are returned via the recycle loop being merged with the F1 feedstream before they enter the LG2F Thermal Olefination process. In this embodiment, surplus LG2F methane can be utilized individually or in any combination as: a diluent, industrial fuel gas, flare gas (C3+ removed), commercial use, converted to LNG, stored or sequestered underground from the atmosphere. In another embodiment, a C2-C5 alkane-rich feedstream preferably comprised of >20% C3+ alkanes is merged with the effluent of the R2 catalytic reactor (e.g. via F2 or F3) and processed by the liquid recovery system to remove specified C4+ liquids and separate light gases and then the C3 alkane-rich feedstream is returned using a high pressure module (e.g. >100-400 psi) to condense and separate C3 alkanes from lighter compounds and passing the C3 compounds into the C3 recycle loop, but without receiving ethane from the F1 feedstream, to reenter the LG2F process via the R1 reactor configured for Propane Thermal Olefination. The propane Thermal Olefination process may benefit from receiving a slit stream of methane gas from the light gas separation process. A parallel flow stream is established for C2 and lighter alkanes (once separated from the C3's) to merge with the ethane feedstream depicted as the F1 feedstream and then enters the Ethane Thermal Olefination process. These parallel Thermal Olefination processes (Ethane and Propane) are devised to optimize the recovery of liquid products where the ratio of alkane-rich feedstream for C2's vs. C3+ is less than 4:1 (wt. %).

Figure 17:
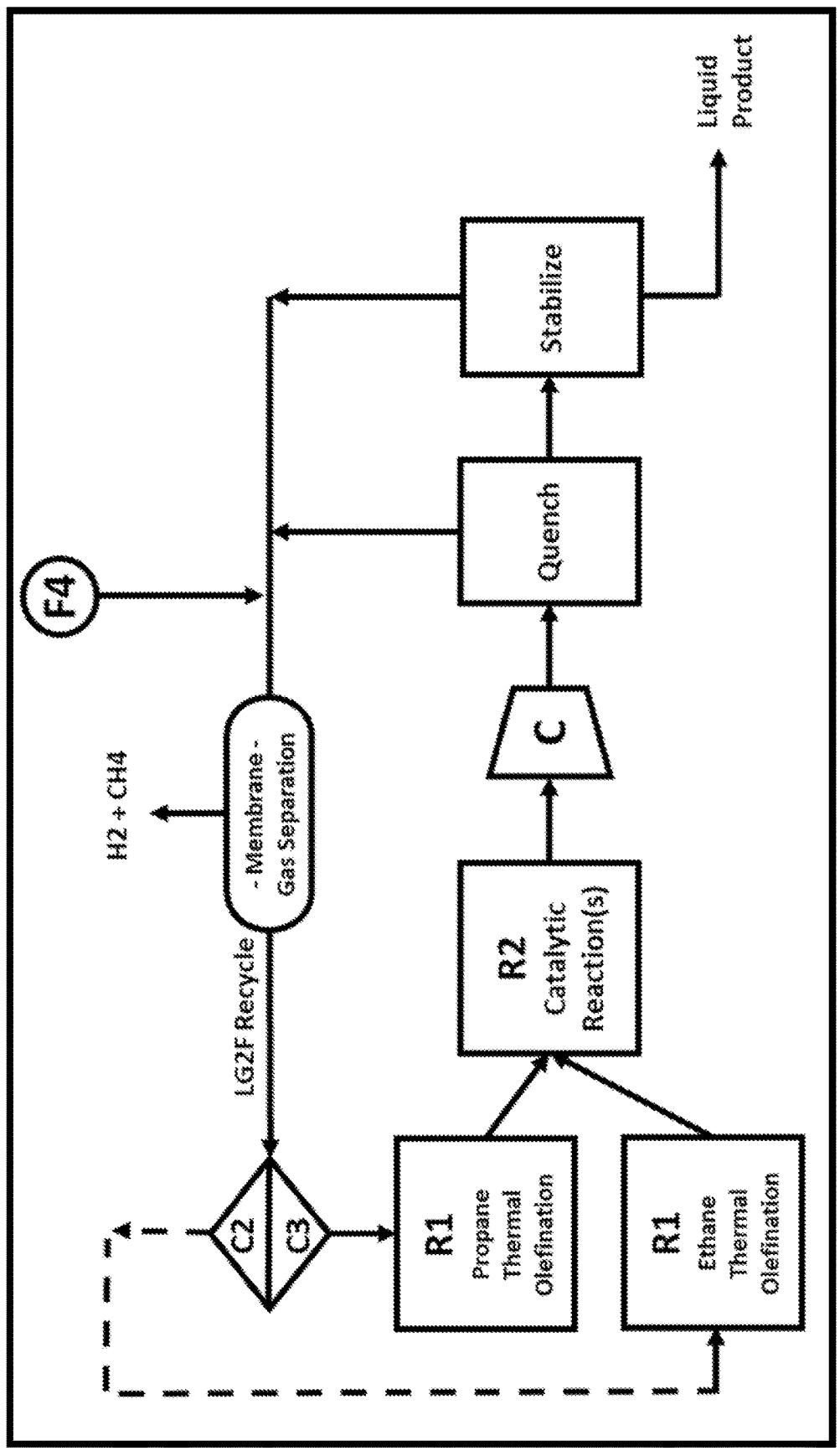
FIG. 17 is a flow diagram showing an embodiment of the process in which an unprocessed wet gas feedstream comprises of greater than 50% (wt.) methane is merged into the LG2F process at feedstream F4.

The LG2F process can be utilized to extract C3+ compounds known to emit black carbon upon combustion. Black carbon emissions are often emitted into the atmosphere when C3+ hydrocarbons comprised in wet natural gas feedstreams are combusted into the air at the time of flaring or any form of open-air combustion. This type of flaring may occur particularly where crude oil and condensate liquid production is underway but there is an absence of a natural gas supply chain. In one embodiment, shown in FIG. 17, the LG2F process operates to dry methane gas by extracting C3 and black carbon emissions. The unprocessed wet gas feedstream comprised of >50% (wt.) methane is merged into the LG2F process at feedstream F4, whereby the majority of the methane gas is separated under pressure without cryogenics or fractionation (i.e. "cleansed" of C3+ hydrocarbons) and if sufficient C2+ light alkanes remain, they can be merged and fed into the Thermal Olefination process. In the event the ratio of remaining C2 vs. C3 alkanes (i.e. % weight once the methane is stripped away) is less than 4:1, then a module is utilized to separate the C3+ hydrocarbons under pressure (e.g. 100-400 psi) to condense and separate the C3 alkanes from the lighter compounds and passing the C3 compounds into the C3 recycle loop, but without receiving ethane from the F1 feedstream, to reenter the LG2F process via the R1 reactor configured for Propane Thermal Olefination. The propane Thermal Olefination process may benefit from receiving a slit stream of methane gas from the light gas separation process. An optional parallel flowstream can be established for C2 and lighter alkanes (once separated from the C3's) to enter the Ethane Thermal Olefination process. This parallel process can then be remerged before entering the R2 catalytic oligomerization process. All liquid product produced from the liquid recovery system can be utilized as gasoline blendstock, gasoline fuel, product storage or comingled with the crude oil or fuel supply chain for efficient transportation. In this embodiment, surplus LG2F methane can be utilized individually or in any combination as: a diluent, industrial fuel gas, anti-coking flare gas (C3+ removed), commercial use, converted to LNG, stored or sequestered underground from the atmosphere.

Figure 18:
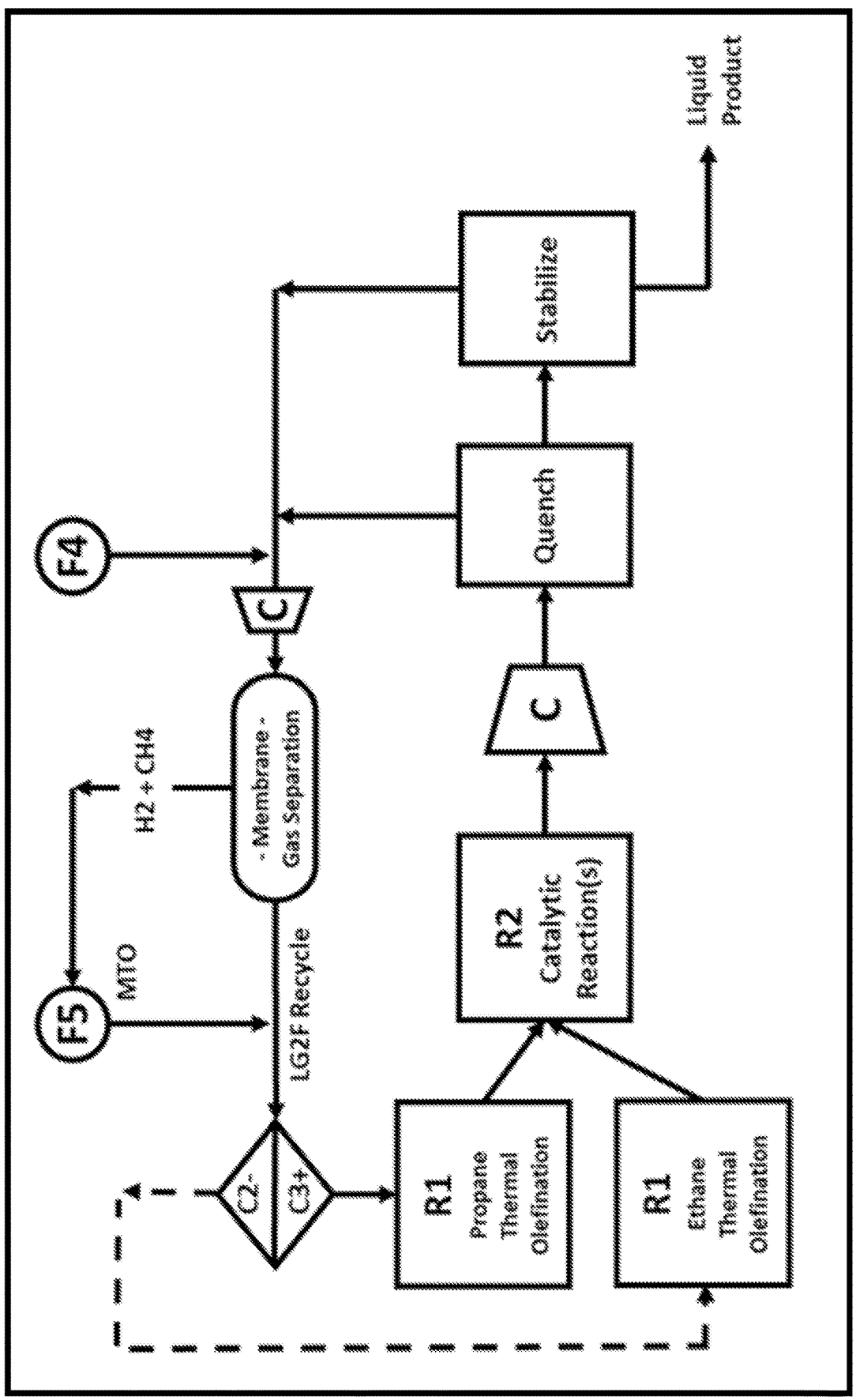
FIG. 18 is a flow diagram showing an embodiment including the use of the Methane Thermal Olefination process to transform the methane molecules to alkanes or alkenes and entry of the converted molecules into the LG2F process at feedstream F5, without methane gas open-air combustion.

A similar embodiment shown in FIG. 18 follows the same pattern of methane gas entering at feedstream 4, however instead of combusting or flaring the methane gas post-separation, the methane is processed by the Methane Thermal Olefination (MTO) process, or any equivalent methane activation process known to those schooled in the art of such activation, to decouple and primarily transform the methane molecules to alkanes or alkenes. The converted molecules reenter the LG2F process at feedstream 5, after which they are available for downstream utilization of either alkane-rich feedstreams (for R1 processing) or alkene-rich feedstreams (for R2 processing) to produce the desired liquid products. This technique allows for the full-scale elimination of wet-gas flaring and is a major environmental benefit to remote oil field operations throughout the world by 1) reducing emissions of un-combusted methane, 2) lowering CO2 emissions by ceasing unnecessary gas flaring, and 3) eliminating so-called "black carbon scarring" that results from C3+ emissions and soot being deposited on the artic snow and polar ice caps.

In practice, some field sources of the C2-5 Alkanes may contain contaminants. In this setting, a contaminant may be any component that adversely affects the LG2F Process or its system components. For example, contaminants may include ammonia, hydrogen sulfide, nitrogen, sulfur and/or water. Some source streams are not scrubbed to reduce such contaminants. These contaminants could poison later-used catalysts or cause accelerated corrosion to downstream (e.g., refining or petrochemical) processing units.

Significant concentrations of these contaminants are preferably removed in advance by conventional pre-treatments including various scrubbing and catalytic methods. The C2-5 Alkane Feedstream preferably contains less than 1%, and more preferably less than 0.5% contaminants. However, pre-treatment is not necessary when using clean light gas feedstocks, e.g., cracked gases from reformate, as these light hydrocarbon streams are treated upstream and contain ultra-low quantities of contaminants.

Inert components (e.g., nitrogen, argon, helium) are by definition non-reactive in the LG2F Process. However, it remains preferable to keep the inert components in limited amounts prior to being purged (e.g. via membrane) from the LG2F Process. Accordingly, the C2-5 Alkane Feedstream (excluding methane) preferably contains less than 5%, and more preferably less than 1% inert materials.

A given C2-5 alkane-rich hydrocarbon source may be processed as obtained, or it may be combined with other available light gas streams for transformation to targeted gasoline or diesel-range transportation fuel blendstocks. Blending streams from 2 or more sources, or augmenting a source stream with one or more added components, is one manner of directing the compositions of the final products.

Example C2-5 Alkane Sources

There are many diverse sources of C2 to C5 light hydrocarbon gas streams. Sources include NGL's, gas condensate, industrial fuel gas, petroleum gases and liquified petroleum gases (LPG), which are available across the oil, gas and petrochemical industry. Suitable C2-5 Alkane sources are typically found in refineries, oil and gas extraction facilities, gas processing plants, petrochemical plants, and liquid petroleum gas (LPG) storage facilities. C2-5 Alkane sources also include any light hydrocarbon gases output of catalytic cracking or catalytic reforming, or streams exiting any paraffin cracking unit. Additional examples include light hydrocarbon gases from hydrotreating and hydrodesulfurization units. These and other C2-5 sources are all eligible to be thermally and catalytically converted to $C_{5+}$ constituents to maximize liquid volume yield of gasoline or diesel fuel blendstocks.

Such streams are light gas compounds, typically containing ethane, propane, butane, pentane or any mixtures thereof. Pentane and butane/pentane mixtures may also be in liquid form at ambient temperatures and pressures. Some sources may be an isolated stream of virtually one compound (e.g. propane). Any combination of suitable C2-5 alkane gas streams can be merged together to utilize this transformative LG2F Process.

The LG2F Process thus provides enhanced utilization of available plant effluents. For example, a cracked, long-chain paraffin byproduct having between 3% and 14% hydrocarbon gases upgrades from low-value industrial fuel uses to a higher-value gasoline blendstock by the LG2F Process. Similar gas constituents (predominately $C_2$+ with hydrogen) from the outputs of catalytic reformers create the opportunity for even larger liquid volume yields of high-octane gasoline blendstocks using the LG2F Process. Any such gas streams can be pretreated if necessary, and processed individually or merged with any number of other available C2-C5 alkane-rich gas streams. For example, in one embodiment, a single incoming or merged light gas feedstream stream may contain a sulfur content in the form of $H_2S$ exceeding a desired fuel specification of typically less than 10 ppm S. In this case, a desulfurization membrane, molecular sieve, or similar separation or molecular absorption technique can be utilized alone or in series to reduce the sulfur content to the required fuel specification levels without adding hazardous processes (e.g. requiring reaction with HF or $H_2SO_4$ or other such toxic chemical reactions) to the process solely to remove sulfur. Since sulfur does not react in the LG2F process, this separation technique can be utilized at any point upstream of the liquid recovery process, but preferably upstream of the Thermal Olefination reactor to reduce any likelihood of sulfur corrosion to the LG2F metallurgy. This technique results in a closed-loop, fully integrated LG2F production process that can provide high-quality ultra-low-sulfur fuels and fuel blendstocks without high cost and resulting in low corrosivity to equipment.

Thermal Olefination

Using an alkane-rich feedstream comprised of ≥90% alkanes, the production of liquid fuels in one embodiment starts with the alkanes being largely converted to olefins via a dehydrogenation step. The LG2F Process uses a Thermal Olefination reaction for this purpose.

Thermal Olefination utilizes endothermic reactions which suitably occur, for example, in an isothermal reactor operating with a constant supply of heat. The Thermal Olefination reactor uses dry heat (>600° C.) to convert the C2-5 Alkanes into olefins having 2 or more carbons ("$C_{2+}$"). The Thermal Olefination reaction avoids the use of catalysts and steam, operating with a very fast reaction time to minimize coking. Various light gas compounds are produced as byproducts, depending on the alkane feedstream but generally, the olefins formed from the Thermal Olefination reaction have the same or fewer carbons than the alkane reactant. For example, pentane may be cracked into olefins and paraffins as illustrated by the following examples:

$$C_5H_{12} \rightarrow C_4H_8(\text{olefin}) + CH_4(\text{paraffin})$$

$$C_5H_{12} \rightarrow C_3H_6 + C_2H_6$$

$C_5H_{12} \rightarrow C_2H_4 + C_3H_8$ $C_5H_{12} \rightarrow C_5H_{10} + H_2$

As another example, ethane may be cracked into ethene, with small quantities of methane and hydrogen as light gas byproducts.

The results of the Thermal Olefination reactions therefore depend largely upon the composition of the alkane-rich C2-5 Alkane Feedstream. The intermediate product is a mix comprised of C2 to C5 olefins, along with a lesser amount of C1-5 alkanes and hydrogen as byproducts. The conversion is selected to maximize gasoline or diesel fuel yields. Methane byproduct may undergo separation (e.g. via various known selective and/or reverse selective membrane separation techniques) from the other light gases and can be utilized as fuel or used as a temperature controlling diluent in the reaction process.

In one embodiment, an alkane feedstream comprised of >90% ethane is merged with a recycle stream containing a blend C1 to C5 of alkanes comprising up to 25% methane and up to about 1% hydrogen. It is found that the inclusion of methane and hydrogen acting as a diluent in the non-catalytic Thermal Olefination reaction not only effectively controls the temperature of reaction in the radiant and adiabatic sections of the reactor, but it also increases the metallurgical longevity of the reactor tube. Unlike LG2F, traditional steam crackers tend to experience corrosion due to the presence of H20 and other chemical additives (e.g. DMDS) which add processing cost and can compromise the metallurgy of the reactor. Based upon our analysis of the reactor, the preferred residence time of the Thermal Olefination reaction is <1 second. The "new ethane" added to the merged feed stream from the recycled portion of the R2 effluent produces a light olefin conversion of more than 80% (wt) in a single pass yield, net of incremental methane and hydrogen from the prior recycle stream. In addition, olefin conversions of greater than 100% are possible because the R2 catalytic conversion created light alkanes which can be recycled to the R1 thermal olefination reaction.

In a second embodiment in a similar thermal reaction, an alkane feedstream is comprised of >10% methane and <1% hydrogen. In a third embodiment in a similar thermal reaction, an alkane feedstream is comprised of >15% methane and <1% hydrogen. In a fourth embodiment in a similar thermal reaction, an alkane feedstream is comprised of >20% methane and <1% hydrogen. In a fifth embodiment in a similar thermal reaction, an alkane feedstream is comprised of >30% methane and <2% hydrogen. In a sixth embodiment, the merged flow rate, either with or without "new ethane", varies in such a way as to keep at least 50% wt. of C2-C5 alkanes present in the R1 Thermal Olefination reaction to sustain a high net olefin conversion rate in a single pass. The use of methane as an inert hydrocarbon diluent in these embodiments also serves to reduce carbon dioxide emissions from the process which in traditional steam crackers is caused by the reaction of excess carbon and steam.

As used herein, the term Thermal Olefination refers to the conversion of alkanes to olefins in relation to controllable variables including the Feedstream composition, temperature, pressure and space velocity. As used herein, Thermal Olefination does not comprise the use of either catalytic or steam cracking. The absence of any dehydrogenation catalyst avoids the high cost and marginal value of managing such dehydrogenation catalysts. The absence of steam in the LG2F Thermal Olefination process eliminates the burden of handling water, steam and fractionation columns and any water separation prior to the downstream R2 catalytic reactor(s). Water is known to rapidly deactivate zeolite catalysts which are utilized in the downstream R2 process. This invention thus uses a low-cost, steam-free, non-catalytic dehydrogenation technique targeting alkane-rich feedstreams.

Figure 2:
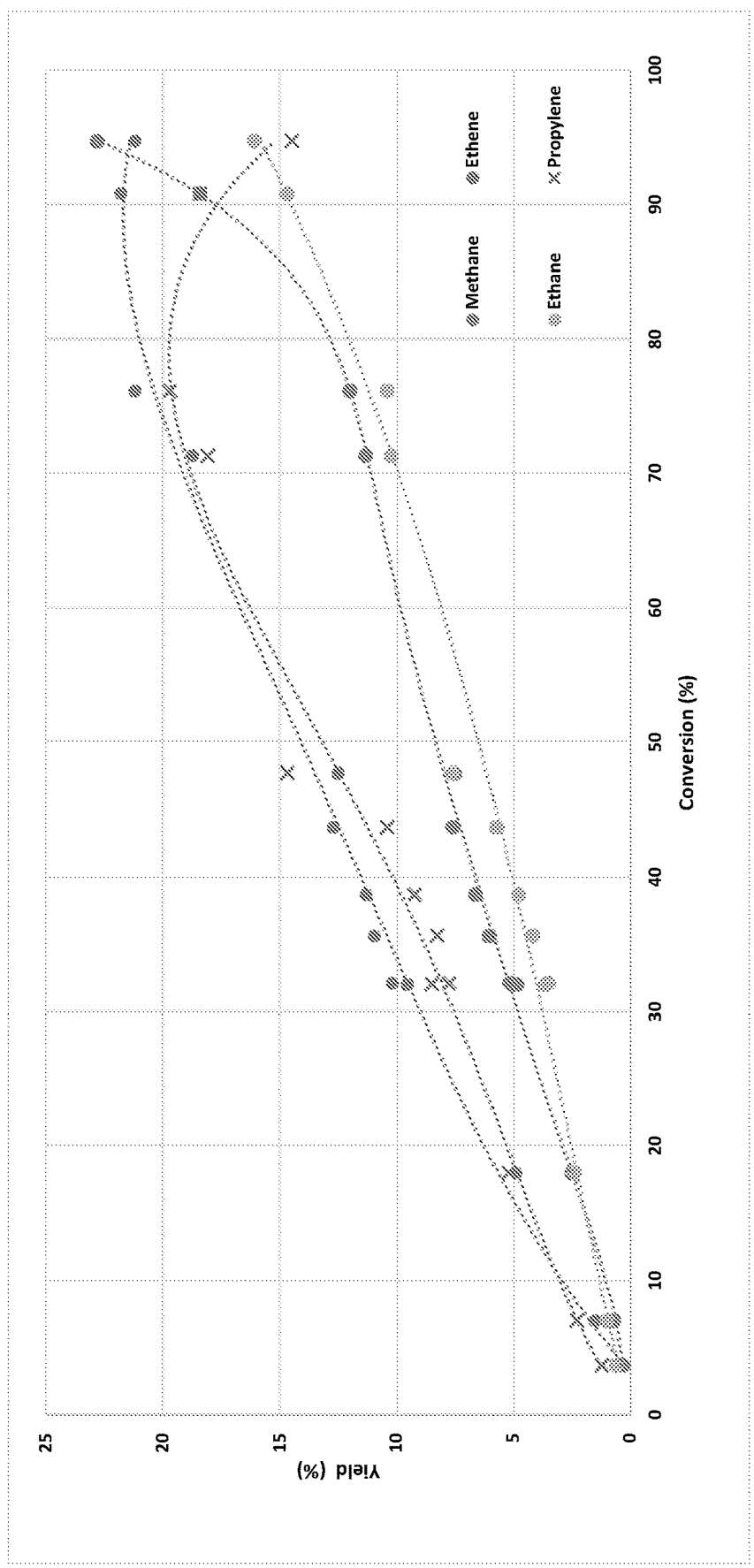
FIG. 2 is a graph showing yield versus conversion for processing of pentane in accordance with the method of FIG. 1.

The results of an exemplary, single-pass LG2F processing of a C5 alkane (pentane) feedstock is shown in FIG. 2. This demonstrates the dependence of the product mix on operating parameters of the LG2F Process. That is, modification of the C2-5 Alkane Feedstream and/or of the operating conditions allows control of the product mix. For example, it is apparent from FIG. 2 that the production of ethene as compared to methane reached an optimal point for product yield. It is also shown that going to 100% conversion was disadvantageous in view of the increased production of methane and the consequent reduction in ethene.

Light Olefin Concentration—The LG2F Process eliminates the use of cryogenic and fractionation processes typi-

| | Single-Pass Yield of New + Recycled Feedstream Comprising C1-C5 Alkanes | | | | | | | |
|---|---|---|---|---|---|---|---|---|
| | R1 Residence Time (sec) | | 0.20 | 0.20 | 0.65 | 0.60 | 0.56 | 0.52 |
| | New Ethane (lbs/hr) | | 700 | 700 | 700 | 700 | 700 | 700 |
| | Merged Flow Rate (lbs/hr) | | 1,574 | 1,574 | 1,574 | 1,666 | 1,757 | 1,849 |
| FEED | Hydrogen | % wt | 0.73 | 0.73 | 0.73 | 0.69 | 0.65 | 0.62 |
| | Methane | % wt | 11.65 | 11.65 | 11.65 | 16.62 | 20.88 | 24.80 |
| | Ethane | % wt | 64.94 | 64.94 | 64.94 | 61.37 | 58.17 | 55.28 |
| | Propane | % wt | 6.84 | 6.84 | 6.84 | 6.47 | 6.13 | 5.82 |
| | Propylene | % wt | 0.63 | 0.63 | 0.63 | 0.60 | 0.57 | 0.54 |
| | C4's | % wt | 12.82 | 12.82 | 12.82 | 12.11 | 11.48 | 10.91 |
| | C5's | % wt | 1.52 | 1.52 | 1.52 | 1.44 | 1.36 | 1.29 |
| | C6's | % wt | 0.87 | 0.87 | 0.87 | 0.70 | 0.76 | 0.74 |
| YIELD | Hydrogen | % wt | 2.57 | 2.55 | 2.90 | 2.77 | 2.66 | 2.55 |
| | Methane | % wt | 20.16 | 20.14 | 24.98 | 28.56 | 31.48 | 34.34 |
| | Ethylene | % wt | 31.65 | 31.46 | 37.16 | 35.50 | 33.96 | 32.47 |
| | Propylene | % wt | 3.82 | 3.83 | 2.35 | 2.31 | 2.28 | 2.25 |
| | C4-Olefins | % wt | 2.32 | 2.33 | 2.19 | 2.07 | 1.95 | 1.85 |
| | Unconverted Ethane | % wt | 34.86 | 35.05 | 25.48 | 24.28 | 23.16 | 22.20 |
| | Unconverted C3+ | % wt | 4.62 | 4.64 | 4.94 | 4.51 | 4.51 | 4.34 |
| | Net Conversion-Olefins/C2+ FEED | % wt | 43.1% | 42.9% | 47.6% | 48.2% | 48.7% | 49.0% |
| | Net Conversion-Olefins/% New Ethane | % wt | 97.0% | 96.5% | 107.0% | 114.8% | 122.2% | 129.5% | cal of traditional techniques to process light gases to produce fuels, blendstocks and base chemicals (e.g. BTX aromatics). In one embodiment, the Thermal Olefination process can be isolated to produce a high proportion of light olefins which may also carry unreacted C2-C4 alkanes. New emerging techniques allow for the use of metal-organic frameworks and similar techniques to achieve >90% separation of C2-C4 olefins from alkanes (e.g. using Cu(I) applied to MFU-41 at varying concentrations, molecular sieves, membranes, etc.) without cryogenics, liquification or distillation. This technique thereby allows the unreacted C2-C4 alkane effluent from the Thermal Olefination process to be separated and recycled to R1 while the C2-C4 olefin effluent can be further concentrated or separated, with or without a subsequent R2 oligomerization reaction. In one further embodiment, the ethylene and/or propylene produced from this isolated Thermal Olefination reaction can be used as specialized petrochemical feedstocks as a precursor as for making such materials as polyethylene and polypropylene.

Standalone Thermal Olefination—The capabilities of the Thermal Olefination reaction without the use of catalysts, chemical additives or steam provide a unique and novel method for producing olefins from any C2-C5 alkane-rich streams of light hydrocarbons including ethane-rich feedstreams. In one embodiment, the traditional use of steam cracking of ethane can be replaced by the Thermal Olefination process to produce ethylene from ethane without the use of steam or chemical additives. In another embodiment, the traditional methods of steam cracking of propane or the use of propane dehydrogenation methods can be replaced by the Thermal Olefination process to produce propylene from propane without the use of steam, catalysts, or chemical additives. In another embodiment, the traditional methods of catalytic dehydrogenation of C3/C4 propane and butanes can be replaced by the non-catalytic Thermal Olefination process to produce light olefins without the use of steam, catalysts, or chemical additives. These traditional processes must continue to utilize capital-intensive separation methods including cryogenics and multiple fractionation steps to separate close boiling compounds to achieve high-purity compounds for petrochemical processing and certain alkylation methods. However, the isolated process of converting, for example, ethane to ethylene or propane to propylene or any combinations thereof are simplified by the Thermal Olefination process. Computer simulations and pilot scale production results indicate that ethylene and light olefin yields are very similar to steam cracking yields, coking levels are very low and runtimes average 60 to 90 days between regeneration steps. The absence of steam and chemicals such as DMDS brings the additional advantages of lowing costs, reducing CO2 emission levels, reducing the impact of corrosion on the metallurgy of the reactor, and reducing the handling of hazardous chemicals.

Thermal olefination performance was evaluated at a 17 lb/hr pure ethane feed stream with 950° C. furnace set-point. Absorbed duty of the reaction is 800 W/lb with a total net of 13.6 kW of absorbed duty.

|  | Thermal Olefination | Steam Cracking |
|---|---|---|
| Pressure | 15 PSIA | 15 PSIA |
| Ethane Partial Pressure | 15 PSIA | 7.5 PSIA |
| Outlet Temperature | 812° C. | 850° C. |
| Residence Time | 0.12 Sec | 0.1 Sec |
| Conversion Yield (w/w) | 65.5% | 67.4% |
| Hydrogen | 3.3.% | 4.1.% |
| Methane | 3.8.% | 5.0.% |
| Ethylene | 52.2% | 52.8% |
| C3 | 1.5.% | 1.4.% |
| C4 | 2.3.% | 1.9.% |
| C5 | 0.3.% | 0.4.% |
| C6 | 1.3.% | 0.9.% |
| C7 | 0.2.% | 0.1.% |

Ethane Thermal Olefination Vs. Steam Cracking—Single Pass High Ethylene Yield

| Propane Thermal Olefination | 1 | 2 | 3 | 4 | 5 | 6 | 7 | 8 | 9 |
|---|---|---|---|---|---|---|---|---|---|
| Conditions: | | | | | | | | | |
| Heater SP, ° C. | 665 | 690 | 690 | 700 | 700 | 700 | 710 | 710 | 715 |
| Internal T | 697 | 727 | 735 | 746 | 745 | 741 | 758 | 758 | 761 |
| Tube Exterior T | 696 | 720 | 723 | 732 | 732 | 733 | 743 | 743 | 747 |
| Propane, mL/min | 4 | 4 | 3 | 3 | 3 | 3 | 3 | 3 | 3 |
| Pressure, psig | 10 | 10 | 10 | 10 | 10 | 0 | 0 | 0 | 0 |
| % Propane Conversion | 22.6 | 35.6 | 48.7 | 47.4 | 53.1 | 44.8 | 52.0 | 54.0 | 57.1 |
| Yield, Wt %: | | | | | | | | | |
| Methane | 4.68 | 7.51 | 10.71 | 10.33 | 11.81 | 9.21 | 11.07 | 11.49 | 12.33 |
| Ethylene | 7.80 | 12.17 | 16.54 | 16.20 | 18.12 | 15.99 | 19.11 | 19.85 | 21.19 |
| Ethane | 1.25 | 2.19 | 3.39 | 3.18 | 3.74 | 1.86 | 2.24 | 2.34 | 2.53 |
| Propylene | 7.57 | 11.95 | 15.23 | 14.63 | 15.85 | 14.77 | 16.33 | 16.83 | 17.22 |
| Propane | 77.45 | 64.37 | 51.29 | 52.58 | 46.92 | 55.19 | 47.97 | 46.04 | 42.86 |
| C2 + C3 Olefins | 15.38 | 24.12 | 31.77 | 30.83 | 33.97 | 30.76 | 35.45 | 36.68 | 38.41 |
| Selectivity | | | | | | | | | |
| Methane | 20.74 | 21.06 | 21.99 | 21.78 | 22.26 | 20.56 | 21.27 | 21.29 | 21.58 |
| Ethylene | 34.61 | 34.16 | 33.97 | 34.16 | 34.14 | 35.68 | 36.74 | 36.78 | 37.08 |
| Ethane | 5.55 | 6.15 | 6.97 | 6.71 | 7.04 | 4.14 | 4.3 | 4.34 | 4.42 |

-continued

| | | | | | | | | | |
|---|---|---|---|---|---|---|---|---|---|
| Propylene | 33.58 | 33.53 | 31.27 | 30.85 | 29.86 | 32.96 | 31.39 | 31.19 | 30.14 |
| C2 + C3 Olefin Selectivity | 68.19 | 67.69 | 65.23 | 65.01 | 64 | 68.64 | 68.13 | 67.97 | 67.22 |

| Propane Thermal Olefination | 10 | 11 | 12 | 13 | 14 | 15 | 16 | 17 | 18 | 19 |
|---|---|---|---|---|---|---|---|---|---|---|
| Conditions: | | | | | | | | | | |
| Heater SP, °C. | 715 | 715 | 715 | 715 | 715 | 715 | 725 | 725 | 735 | 735 |
| Internal T | 760 | 758 | 761 | 762 | 760 | 761 | 768 | 768 | 785 | 786 |
| Tube Exterior T | 747 | 747 | 747 | 747 | 746 | 746 | 758 | 758 | 768 | 768 |
| Propane, mL/min | 3 | 3 | 3.5 | 3.5 | 4 | 4 | 4 | 4 | 1 | 4 |
| Pressure, psig | 0 | 10 | 10 | 10 | 10 | 10 | 10 | 10 | 10 | 10 |
| % Propane Conversion | 55.2 | 65.5 | 63.2 | 71.1 | 67.5 | 67.6 | 74.5 | 78.3 | 85.1 | 87.8 |
| Yield, Wt %: | | | | | | | | | | |
| Methane | 11.79 | 15.71 | 14.76 | 17.44 | 15.94 | 16.21 | 18.61 | 19.89 | 24.08 | 25.42 |
| Ethylene | 20.37 | 22.20 | 21.37 | 24.05 | 22.91 | 22.92 | 25.72 | 26.94 | 30.40 | 30.80 |
| Ethane | 2.38 | 5.24 | 4.83 | 5.76 | 5.23 | 5.31 | 5.96 | 6.38 | 7.23 | 7.48 |
| Propylene | 16.93 | 17.14 | 16.67 | 17.12 | 17.40 | 17.17 | 17.41 | 16.86 | 15.01 | 14.06 |
| Propane | 44.83 | 34.53 | 36.77 | 28.89 | 32.49 | 32.36 | 25.50 | 21.74 | 14.86 | 12.23 |
| C2 + C3 Olefins | 37.30 | 39.34 | 38.04 | 41.17 | 40.32 | 40.09 | 43.13 | 43.79 | 45.41 | 44.86 |
| Selectivity | | | | | | | | | | |
| Methane | 21.37 | 24.00 | 23.35 | 24.53 | 23.61 | 23.96 | 24.98 | 25.41 | 28.28 | 28.96 |
| Ethylene | 36.92 | 33.90 | 33.80 | 33.82 | 33.94 | 33.89 | 34.52 | 34.42 | 35.70 | 35.10 |
| Ethane | 4.32 | 8.01 | 7.63 | 8.09 | 7.75 | 7.84 | 8.00 | 8.15 | 8.49 | 8.52 |
| Propylene | 30.68 | 26.18 | 26.36 | 24.08 | 25.78 | 25.39 | 23.37 | 21.54 | 17.63 | 16.02 |
| C2 + C3 Olefin Selectivity | 67.60 | 60.09 | 60.16 | 57.90 | 59.72 | 59.27 | 57.89 | 55.95 | 53.33 | 51.12 |

Propane Thermal Olefination (Recyclable)—1$^{st}$ Pass Ethylene/Propylene Yield and Selectivity In one embodiment, the Thermal Olefination reactor is configured to convert a light gas comprised of >90% ethane and propane into ethylene and propylene. As needed, critical feedstock impurities (e.g. sulfur, arsenic, mercury, metals) are removed prior to R1 processing. The R1 reactor system is configured as a single pass process without recycle to generate the maximum C2+ olefin yield. The absence of steam, CO, CO2, and sulfur brings significant processing advantages to this invention. The availability of excess hydrogen without CO is an advantage to this invention in the alkyne hydrogenation process. The Thermal Olefination effluent, following a rapid quench process in the transfer line exchanger, has the option to undergo membrane separation of inert gases (e.g. methane, hydrogen) and/or any alkane/alkene separation methods at ambient or moderate pressures as a precursor for downstream processing. Upon passing this optional separation phase, the (remaining) effluent enters a higher-pressure gas phase cryogenic separation process whereby the methane is separated from the effluent (demethanized) for recycle or commercial use. Then at about 20-40° C. and about 400-500 psi, the C2+ bottoms comprising close-boiling ethane and ethylene are further separated (deethanized), and then together fed to an alkyne hydrogenation process to improve alkane/alkene purity, followed by a C2 fractionation unit to split the ethane from the ethylene. Then taking the C3+ deethanized bottoms at about 150 to 300 psi, the close-boiling propane and propylene are separated (depropanized) and then together catalytically hydrotreated to remove alkynes, followed by a C3 fractionation unit to split the propane from the propylene. The remaining C4+ bottoms of the depropanizer may be further processed or used for LG2F fuel blendstock. At this point, the separated methane (as needed for diluent), ethane and propane streams can be recycled to the Thermal Olefination process. Polymer grade ethylene may require further handling and purification. Polymer grade propylene may require further handling and purification.

In another embodiment, the Thermal Olefination reactor is configured to process a light gas feedstream comprised of >50% ethane or propane for conversion into ethylene and propylene. As needed, critical feedstock impurities (e.g. sulfur, arsenic, mercury, metals) are removed prior to R1 processing. The R1 reactor system is configured as a recyclable process to generate the maximum C2+ olefin yield. The absence of steam, CO, CO2, and sulfur in the reaction brings low-cost processing advantages to this invention. The availability of excess hydrogen without CO is an advantage to this invention in the alkyne hydrogenation process. The Thermal Olefination effluent, following a rapid quench process in the transfer line exchanger, has the option to undergo membrane separation of inert gases (e.g. methane, hydrogen) and/or any alkane/alkene separation methods at ambient or moderate pressures as a precursor for downstream processing. Upon passing this optional separation phase, the (remaining) effluent enters a higher-pressure cryogenic separation process whereby the methane is separated from the effluent (demethanized) for recycle or commercial use, then at about 20-40° C. and about 350-500 psi the C2+ bottoms comprising close-boiling ethane and ethylene are separated (deethanized), and then together fed to an alkyne hydrogenation process to improve alkane/alkene purity, followed by a C2 fractionation unit to split the ethane from the ethylene. Taking the C3+ deethanized bottoms at about 150 to 300 psi which include the close-boiling propane and propylene are then separated (depropanized) and then together catalytically hydrotreated to remove alkynes, followed by a C3 fractionation unit to split the propane from the propylene. The remaining C4+ bottoms of the depropanizer may be further processed or used for LG2F fuel blendstocks. At this point, the separated methane (as needed for diluent), ethane and propane streams may be recycled to the R1 Thermal Olefination process. Polymer grade ethylene post-C2-fractionation may require further treating and purification. Polymer grade propylene post-C3-fractionation may require further treating and purification. Any residual C4+ materials are available as fuel grade blendstocks, for further product separations or for continued LG2F processing.

These specialized Thermal Olefination methods outlined herein that utilize techniques known to those schooled in the art of Hydrogen, C1, C2, C3 and C4 gas-liquids separation methods and the subsequent alkyne hydrogenation methods to increase alkane/alkene yields (purity) and the final splitting of ethane from ethylene and propane from propylene may be utilized in any commercially viable manner to accommodate this process. Cold box cryogenics and NGL fractionation technology including tray design (e.g. valve and sieve, dual-flow, crossflow, baffle-deck, etc.) and choice of random vs. structured packing materials are all critical design choices. Novel techniques may include the use of divided-wall distillation columns to separate C1 from C2 from C3 from C4 streams prior to the alkyne hydrogenation steps. Light gases from any of the fractionation towers may be recycled to the compression systems to offset demands for increased horsepower. High pressure gas separation methods (i.e. C2 and C3 splitters) include the configuration of condensers, reflex vessels, and reboilers to adequately affect separation of close-boiling alkane vs alkene hydrocarbons. Together these collective processes are called the Thermal Olefination process for producing Base Petrochemicals ("TOBP").

It is further understood that polymer grade ethylene from the TOBP process is a major feedstock to the production a wide range of petrochemical products including polyethylene (HDPE, LDPE, LLDPE), alpha-olefins (via oligomerization), and various other chemical products. Similarly, it is understood that polymer grade propylene from the TOBP process is a major feedstock to the production a wide range of petrochemical products including polypropylene, propylene oxide, acrylonitrile, and various other chemical products.

It is understood that any attempt to retrofit an ethane steam cracker or propane steam cracker or naphtha cracker or propane dehydrogenation unit or any similar thermal or catalytic unit to crack or dehydrogenate hydrocarbons to function as a Thermal Olefination reactor as described herein falls with the scope of this invention. The removal of steam, chemical additives, and/or catalytic techniques from these existing process devices in order to employ the benefits of the Thermal Olefination process is included in this invention. The Thermal Olefination process may also utilize any heating technique known to those schooled in the art, including gas-fired heat (comprised primarily of either methane or hydrogen as btu sources), and/or the use of electrical heating or resistance heating methods to deliver process heat in the convection and/or radiant sections of the furnace, but without any requirement to use catalysts or steam in the R1 reactor. Furthermore, the incorporation of the various plating (anti-coking) techniques and carbon capture methods and/or regeneration techniques are also distinguishing features of the Thermal Olefination process as identified in this invention. These factors taken individually or together bring about a process simplification, a reduction to CO and CO2, and a lower-cost alternative to the global process industry seeking to create valuable fuel products and petrochemicals from hydrocarbons.

The LG2F Process utilizes Thermal Olefination reactors configured to dehydrogenate the C2-5 Alkanes to form olefins without the requirement of any catalyst. The Thermal Olefination reactor may be of conventional design, including as simple as a tubular chamber, designed to withstand high continuous service temperatures from as low as 450° C. for cracking butanes to greater than about 925° C. for cracking ethane. To minimize carbon build-up, a protective layer may be crafted onto the internal surface area of the entire reactor via plating (e.g. chemical plating, electroplating, or other thin film deposition techniques,) to produce a superficial layer of aluminum that is oxidized to alumina. Alumina has known chemical and heat resistive properties up to 1700° C. in the absence of high-temperature steam and will thereby inhibit deposition of carbon onto the inner tube surface by preventing chemical access to iron surface atoms. This specialized aluminum/alumina coating thus increases the process lifecycle by reducing coke accumulation.

Other high temperature metals (e.g. B, Ce, Cr, Co, Hf, Ho, Ir, Mo, Nb, Re, Ta, and Ti), high temperature ceramics, or selected metallic oxides are viable materials for thin-layer deposition on the inner wall of any R1 reactor(s) for minimizing the effect of coking. Formulations for the thin film deposition technique vary but preferred embodiments include halide anions (activators) selected from fluoride (F—), chloride (Cl—), bromide (Br—), iodide (I—) and/or astatide (At—) to enhance the evaporation process. Other non-halide activators may also be applied as known by those schooled in the art of thin film deposition. The selected metals and metal oxides or their alloys (non-oxides) or combinations of these may be utilized for thin film deposition in the preferred embodiments must have melting points >500° C. and boiling points >2000° C. and may be applied using halides with specialized evaporative or vaporized carrier-gas bonding techniques to form a metallurgical aluminide surface.

| High Temp Metals | Element | Boiling Pt ° C. | Melting Pt ° C. |
| --- | --- | --- | --- |
| Aluminum | Al | 2,470 | 660 |
| Aluminum Oxide | $Al_2O_3$ | 2,977 | 2,072 |
| Boron | B | 3,927 | 2,076 |
| Cerium | Ce | 3,443 | 795 |
| Chromium | Cr | 2,672 | 1,907 |
| Cobalt | Co | 2,870 | 1,495 |
| Hafnium | Hf | 4,602 | 2,233 |
| Holmium | Ho | 2,695 | 1,472 |
| Iridium | Ir | 4,130 | 2,466 |
| Molybdenum | Mo | 4,639 | 2,623 |
| Niobium | Nb | 4,927 | 2,477 |
| Rhenium | Re | 5,597 | 3,185 |
| Tantalum | Ta | 5,457 | 3,017 |
| Titanium | Ti | 3,287 | 1,668 |

Other coke-resisting methods applied to the inner wall of the R1 reactor(s) may include the use of acid-bath passivation techniques. These methods outlined herein to minimize coking on the inner wall of the reactor are all integral to the design of the Thermal Olefination reactor.

In one embodiment, each Thermal Olefination (R1) reactor tube is configured using a special interior plating technique via a thermal evaporative thin film chemical deposition process whereby aluminum oxide (alumina) is deposited onto the entire inner wall of each reactor tube including the tubing and manifolds immediately downstream of the reactor leading to an entrained-gaseous carbon extraction device through which the effluent of the R1 reaction passes. In a second embodiment, the reactor tubes are packed with a powered formulation of metallic compounds comprising a high-temperature metal (preferably aluminum), a halide (preferably aluminum chloride) to activate the evaporation purposes and an inert diluent (preferably aluminum oxide) which are then sealed inside the tube and heated until the temperature exceeds the evaporation point of the powdered mixture, typically between 500° C. to 1500° C., for a period of 0.5 to 4 hours to form a thermochemical vapor followed by a diffusion bonding period of up to 48 hours during which the chemicals oxidize and uniformly diffuse across the sealed vessel creating a thin aluminum oxide layer onto the inner walls of each sealed vessel, thereby providing a non-reactive and non-corrosive sheath on the inner wall of each reactor tube. The time of the diffusion process and the chemical formula vary based upon the desired thickness of the deposition required. Another group of embodiments uses variations of this thin film deposition technique including chemical vapor deposition with one or more high temperature metals, halides and metal oxide compounds and/or any physical vapor deposition method for adhering to the inner walls of the reactor and related vessels via any appropriate high-temperature metallic oxide diffusion coating technique. These high-temperature metallic reactor vessels may use any appropriate form of physical vapor or chemical vapor thin film deposition process to achieve the desired coating thickness and anti-corrosion behavior typically ranging between as thin as 1-10 nanometers up to a thickness of 100 micrometers on their inner walls. This protective layer prevents the iron (Fe), typically found as a component at >50% (m/m) in various grades of carbon steel, stainless steel and iron- or nickel-based-alloy reactor vessels, from chemically bonding with the carbonic reactants from the dry-heat Thermal Olefination reaction which can thereby form coke deposits on the walls of the reactor which could then build-up and obstruct the high temperature gaseous hydrocarbon flow through the reactor.

Our research shows that the aluminized coating of a 310 stainless steel reactor tube operating at temperatures from 600° C. to 900° C. with a continuous gas flow of hydrocarbons in the absence of steam or harsh chemical additives (e.g. dimethyl disulfide) was able to virtually eliminate the effect of catalytic coking, operate with unobstructed gas flow and thereby extend the life of the reactor vessel. Prior to any thin-film aluminizing treatment, the inner reactor walls of a 310 stainless steel vessel became caked by the catalytic iron-carbonization reaction that drew iron out of the stainless steel vessel creating a coking hot-spot which accumulated multiple layers of carbon within 120-hours of operation ultimately leading to an obstruction in the gas flow. However, with the appropriate thin-film deposition technique using alumina on the inner wall of the entire reactor tube, there was no catalytic iron-carbonization affect observed along the entirety of the vessel over long operating periods and it was observed that the hydrocarbon gas flow was not obstructed. The impact of eliminating catalytic coking in this controlled experimental environment reduced the total amount of carbonized coke produced from the Thermal Olefination reaction by 80%. The residual 20% attributed to pyrolytic coking occurring away from the reactor walls was then efficiently captured by downstream carbon collectors for removal from the system—thereby reducing the total coke formation from the entire Thermal Olefination reactor system without any emissions of CO2.

The Thermal Olefination process can be applied with or without any of the chemical plating methods described above, such as the thermal evaporative deposition technique. However, the use of alkane feed compounds comprised of >10% C3+ alkanes generally tends to result in higher amounts of catalytic coking on the reactor walls in the absence of any plating technology. Test results of this invention have shown that the Thermal Olefination conversion from alkanes to alkenes is increased by 20-50% using alumina thin film deposition methods due to the significant reduction of coking specifically caused by the high-temperature gas stream coincidentally reacting to the inside metallurgy of the reactor walls caused particularly by the thermal cracking of C3+ alkanes. In the chart below, lab-scale test runs 4, 5, and 7-10 indicate the higher yield of olefins resulting from the use of such specialized plating techniques to shield the metallurgy on the interior of the reactor tube from the hot gas stream. In testing of this invention, the use of high-temperature materials for plating the inside of the reactor tube reduced coincidental coking by up to 85%.

| Thermal Olefination of Propane | | | | | | | | | | |
|---|---|---|---|---|---|---|---|---|---|---|
| | Run 1 | Run 2 | Run 3 | Run 4 | Run5 | Run 6 | Run 7 | Run 8 | Run 9 | Run 10 |
| Test A = 316 Stainless Steel | | | | | | | | | | |
| Feed | | | | | | | | | | |
| Heater SP, ° C. | 665 | 700 | 700 | 700 | 715 | 715 | 715 | 715 | 735 | 735 |
| Propane, mL/min | 4 | 3 | 3 | 3 | 3 | 3 | 3.5 | 3.5 | 4 | 4 |
| Pressure, psig | 10 | 10 | 10 | 0 | 0 | 10 | 10 | 10 | 10 | 10 |
| Yield | | | | | | | | | | |
| Conversion (wt % Reacted) | 13.3 | 40.8 | 42.2 | 31.3 | 41.5 | 50.7 | 45.9 | 48.7 | 52.7 | 51.9 |
| Ethylene (wt %) | 4.9 | 13.6 | 14.1 | 10.8 | 14.7 | 17 | 15.5 | 16.4 | 18.2 | 18.3 |
| Propylene (wt %) | 3.4 | 13.4 | 13.8 | 10.9 | 13.9 | 15.5 | 14.5 | 15.1 | 15.7 | 15.4 |
| Olefin Yield (wt %) | 8.3 | 27 | 27.9 | 21.7 | 28.6 | 32.5 | 30 | 31.5 | 33.9 | 33.7 |
| Test B = Aluminized 310 Stainless Steel | | | | | | | | | | |
| Feed | | | | | | | | | | |
| Heater SP, ° C. | 665 | 700 | 700 | 700 | 715 | 715 | 715 | 715 | 735 | 735 |
| Propane, mL/min | 4 | 3 | 3 | 3 | 3 | 3 | 3.5 | 3.5 | 4 | 4 |
| Pressure, psig | 10 | 10 | 10 | 0 | 0 | 10 | 10 | 10 | 10 | 10 |
| Yield | | | | | | | | | | |
| Conversion (wt % Reacted) | 22.6 | 47.4 | 53.1 | 44.8 | 55.2 | 65.5 | 63.2 | 71.1 | 85.1 | 87.8 |
| Ethylene (wt %) | 7.8 | 16.2 | 18.1 | 16 | 20.4 | 22.2 | 21.4 | 24.1 | 30.4 | 30.8 |

-continued

Thermal Olefination of Propane

|  | Run 1 | Run 2 | Run 3 | Run 4 | Run5 | Run 6 | Run 7 | Run 8 | Run 9 | Run 10 |
|---|---|---|---|---|---|---|---|---|---|---|
| Propylene (wt %) | 7.6 | 14.6 | 15.9 | 14.8 | 16.9 | 17.1 | 16.7 | 17.1 | 15 | 14.1 |
| Olefin Yield (wt %) | 15.4 | 30.8 | 34 | 30.8 | 37.3 | 39.3 | 38.1 | 41.2 | 45.4 | 44.9 |
| Olefin Yield Improvement (TEST B vs A) | | | | | | | | | | |
|  | 86% | 14% | 22% | 42% | 30% | 21% | 27% | 31% | 34% | 33% |

Chart: Impact of Aluminized SS Tubes in Thermal Olefination Reactor Using Propane In one embodiment, a high-temperature reactor is designed to utilize a configuration of stainless steel reactor tubes appropriately treated with plating methods such as aluminized thin film deposition techniques so as to largely eliminate coincidental catalytic coking of the walls of the tubes and related interfacing areas contacting the alkane-rich feedstream with >20% C3+ alkanes during the Thermal Olefination reaction. This resulted on average 30% higher olefin yields, fewer hot spots, less flow obstructions, and longer processing times between regeneration cycles for the reactor tubes. This C2-C5 alkane cracking technique without steam or catalysts can be utilized in a specialized single pass or recyclable process for producing a light gas effluent comprising ethylene and propylene for downstream petrochemical uses. Subsequent distillation may be utilized for tailoring specialized products to feed downstream processes. This C2-C5 alkane cracking technique without steam or catalysts can also be utilized in a single pass or recyclable process for producing an alkene-rich feedstream for the LG2F R2 Oligomerization process.

One advantage of the Thermal Olefination C2-C5 alkane-rich cracking technique without steam or catalysts used in this invention is, when applied to high concentrations of propane, this invention outperforms typical propane (catalytic) dehydrogenation techniques found in industry. This is the result of eliminating the complex catalytic regeneration processes often used in Propane Dehydrogenation processes (e.g. licensed as CATOLIN or Oleflex) which in many cases may require complex reactor designs supporting catalytic regeneration methods within 10-30 minutes or within 8 hours, respectively. The Thermal Olefination process in this invention as described only requires regeneration of the reactor tubes about every 30 to 90 days depending upon the processing configuration.

Olefination Operating Conditions

The Thermal Olefination reaction is performed at a high-temperature, with no catalyst or steam utilized. The Thermal Olefination reactor is preferably operated with dry heat at a temperature above 600° C., an internal pressure of 0-1500 psig, and a gas weight hourly space velocity of 30-1000 $hr^{-1}$. The Thermal Olefination process does not materially affect methane in the Feedstream. The presence of steam as a byproduct of the R1 Thermal Olefination reaction with light hydrocarbons must be avoided as it can be damaging to the subsequent R2 catalytic reaction.

TABLE 2

| | | Examples of R1 Thermal Olefination Reactions | | | | | | | | |
|---|---|---|---|---|---|---|---|---|---|---|
| | Test Run # | 018-1 | 018-3 | 118-1 | 118-2 | 118-3 | 118-4 | 218-1 | 218-2 | 218-3 |
| Conditions | Reactor T, ° C. | 800 | 800 | 800 | 800 | 800 | 800 | 810 | 820 | 830 |
| | Ethane, sccm | 1580 | 790 | 1185 | 1580 | 790 | 790 | 790 | 790 | 790 |
| | Pressure, Psig | 30 | 18 | 19 | 19 | 14 | 0 | 0 | 0 | 0 |
| | % Conv | 39.52 | 45.64 | 35.18 | 29.59 | 46.90 | 37.17 | 39.66 | 47.81 | 54.31 |
| % Yield | Methane | 5.74 | 9.30 | 5.48 | 4.03 | 9.25 | 4.13 | 4.85 | 6.59 | 8.22 |
| | Ethene | 28.02 | 33.53 | 27.56 | 23.71 | 34.77 | 31.48 | 33.16 | 39.14 | 43.69 |
| | Ethane | 60.89 | 54.62 | 65.07 | 70.64 | 53.38 | 63.09 | 60.61 | 52.47 | 45.97 |
| | Propylene | 1.69 | 1.21 | 0.89 | 0.71 | 1.22 | 0.60 | 0.61 | 0.81 | 0.92 |
| | Propane | 0.22 | 0.14 | 0.18 | 0.24 | 0.12 | 0.16 | 0.15 | 0.11 | 0.11 |
| | Benzene | 1.05 | 0.27 | 0.13 | 0.08 | 0.33 | 0.06 | 0.09 | 0.16 | 0.26 |
| % Selectivity | Methane | 14.51 | 20.37 | 15.57 | 13.63 | 19.73 | 11.10 | 12.23 | 13.79 | 15.13 |
| | Ethene | 70.92 | 73.46 | 78.35 | 80.14 | 74.14 | 84.69 | 83.63 | 81.87 | 80.44 |
| | Propylene | 4.27 | 2.64 | 2.52 | 2.41 | 2.61 | 1.61 | 1.55 | 1.70 | 1.69 |
| | Propane | 0.55 | 0.31 | 0.51 | 0.82 | 0.27 | 0.44 | 0.38 | 0.24 | 0.21 |

In one embodiment, the introduction of hydrogen (H2) into the R1 feedstream as a diluent can be used to manage the effective use of heat and reduce the potential of coking and carbon build-up in the R1 reactor system. This hydrogen can be introduced from any H2 byproduct recycled from any R2 rector and appropriately separated to isolate H2 or it can originate from any alternative H2 sources. The continuous recycle of this H2 gas reduces unnecessary or inefficient H2 consumption. For those skilled in the art of membrane separation, low-cost H2 recovery methods using various pressurized membrane diffusion methods are routinely available without the use of cryogenic cooling. Other cost-effective methods may also be employed in similar embodiments.

Reactor Regeneration—R1

The LG2F Thermal Olefination system may include an integrated reactor regeneration and cleaning sequence (RRC). Operability of the Thermal Olefination reactor(s) is dependent upon reactor lifecycles and the resulting amount of thermal resistance that may occur from carbon build-up on reactor walls. This RRC sequence is performed to reduce or eliminate carbon buildup (coking). Regeneration and cleaning of the reactor(s) operating at high temperatures involves a unique series of steps, during which the light hydrocarbon feedstream flow is paused, in order to restore active levels of the reactor(s). Alternative reactor designs (e.g. continuous regen designs) may also allow for a continuous R1 reactor operation without any pause in operation Two methods for regenerating and cleansing the Thermal Olefination reactors are provided, which can be used with a single reactor, or with multiple units operated in parallel or in series.

The Reactor Regeneration intentionally avoids the potential for deleterious amounts of high-temperature steam impacting the Thermal Olefination reactor and prevents water contaminants from passing to the downstream zeolite-catalytic reactor(s). This is to prevent permanent deactivation of the downstream zeolite catalyst used in the R2 reactor(s). The removal of generated water (i.e. via low-temperature burning of the hydrogen in carbon-coke) avoids the detrimental effects of water gaining access to the zeolite catalyst (via active site reduction and dealumination) used downstream in the R2 reaction. Subsequently, the remaining carbon in the coke is burned-off at higher temperatures forming CO2, which is not harmful to the zeolite catalyst.

The Thermal Olefination process allows for the capture and collection of residual carbon primarily caused by the pyrolytic coking of the thermal reaction. Coke deposits are gathered and shed by some combination of agitation and/or high temperature calcining of the residual carbon deposits captured in the collector device.

Traditionally, alkane dehydrogenation reactors have used either catalytic or steam cracking methods. Steam or steam/air methods were used to reduce or eliminate coking. However, such methods require large capital investments to manage water, steam boilers and water separation techniques. In the LG2F Processes, regeneration is performed without the use of steam or steam/air mixtures, making the overall LG2F System long-lived and cost efficient. The absence of added water (e.g., by way of steam) enhances operation of the LG2F System.

A. Low Temperature Hydrogen and High Temperature Carbon Regeneration

One Reactor Regeneration sequence for regeneration of the Thermal Olefination reactors requires two-steps. This sequence is specifically designed to (1) safely react hydrogen with oxygen to form water at low temperature (under such conditions that the carbon in the reactor does not burn), and (2) then after burning hydrogen, water is removed entirely from the system, before conducting a high-temperature carbon/oxygen reaction to cleanse/regenerate the reactor.

Step 1: Low Temperature Hydrogen Removal

The first step in the regeneration sequence is initiated by flowing a low concentration of oxygen, e.g., in air, through the Thermal Olefination reactor at a temperature where only hydrogen in coke will burn. The oxygen comprises preferably no more than 21% v/v, and more preferably no more that 5% v/v, and even more preferably no more than 1% v/v. A diluent gas, such as nitrogen, CO2 or argon, is used to decrease the concentration of combustible oxygen for the water production phase. The reduced oxygen concentration during regeneration allows for a lower temperature flame front.

This oxygen-containing feed gas is heated in the Thermal Olefination reactor until a flame front is observed in the reactor. This flame front is strictly due to the combustion of hydrogen to water at a lower temperature than that of combusting carbon. The flame front travels through the reactor until no hydrogen is present at the reactor outlet, and the hydrogen burndown process is then complete. The generated water is collected as a liquid in a condensing chamber or vented to the atmosphere, or recycled and mixed in the air containing regeneration gases.

Step 2: High Temperature Carbon Removal in the Absence of Hydrogen

The second step is a carbon combustion cleansing sequence performed once the water has been appropriately purged from the system. While an oxygenated gaseous stream is still being passed through the R1 reactor system the temperature is increased from its initial water removal step to a temperature at which a second flame front is observed. This second flame front is largely devoid of water as the first burndown sequence combusted preferably at least 90% of the hydrogen, more preferably at least 95%, and even more preferably at least 99% of the hydrogen. The only combustion product resulting from the second carbon combustion sequence is therefore primarily due to the production of carbon dioxide, with little to no carbon monoxide. This flame front is followed through the R1 reactor until a flame front is no longer observed. Once the flame front is no longer being produced, the reaction chamber of the Thermal Olefination units is sufficiently devoid of coke.

This two-step sequence can be conducted at any level of carbon build-up, but preferably not more than at 50% of the unit's lifecycle, more preferably not more that 30% of the unit's life cycle, and most preferably not more than 20% of the unit's lifecycle. This 2-step sequence can be performed in-situ, offline from the hydrocarbon flow, on an individual reactor operating in parallel with other Thermal Olefination reactors, to assure a continuous LG2F Process. In another embodiment, duplicate reactors of the same type are used in parallel with different burndown time rotations so at least one unit can be online continuously. The procedure can be fully automated to allow the starting and stopping of the regeneration sequence and the resumption of the hydrocarbon feedstream to continue Thermal Olefination reaction.

B. Compressed Air

A second option for the Reactor Regeneration method involves stopping the hydrocarbon feed before substantial coke formation occurs, then introducing compressed air into the reactor zone at 0-50° C. below the typical unit operating temperature. The regeneration proceeds for a short time duration, which may be limited by the effects of exothermic heat. This regeneration cycle is preferably designed to limit exothermic heat, by using a frequent regeneration cycle which keeps carbon build-up at low levels. Within minutes, the carbon build-up is purged. The process thereby emits CO2, $H_2O$ and excess air for venting to the atmosphere.

While any regeneration cycle can be used, a higher frequency regeneration cycle (e.g., 15 minutes every 1-15 days) allows for minimal water partial pressure in the combusted products as carbon and hydrogen become the limiting reactants, rather than oxygen. In general, the frequency of the regeneration is dependent on the feedstream quality which impacts the level and/or rate of coke formation.

Pre-Processing Natural Gas Feedstream for R1

The Thermal Olefination process is highly flexible and may function using any combination of feedstreams comprising any C2, C3, C4 and/or C5 alkanes. In addition, the R1 feedstream may also contain methane in any amount, which will be unreacted in the R1 and R2 processes, but which can serve as a diluent for thermal control in both the R1 and the R2 reactions. Based upon our research, the use of methane from 5%-35% (wt) in the R1 Thermal Olefination reaction can be cost-effective to reduce the undesirable cracking of C2+ alkanes into shorter-chain molecules that would otherwise form surplus methane and carbon coke. This intentional use of surplus methane represents a useful carbon mitigation technique that increases the overall yield of C2+ alkenes per net consumption of C2+ alkanes processed. The following example shows how in isolation the methane feed is increased up to 250% (from 183.4 to 458.6 lb/hr) resulting in a) an unexpected 12% reduction of "new" methane production, and b) increased ethylene and olefin production as a percent of converted ethane.

It is important to note that methane's behavior with the metallurgy of the R1 reactor is preferred vs steam cracking. Using steam in the R1 reaction is undesirable due to a) its corrosive impact to the metallurgy and b) its chemical reaction with C2+ alkanes results in excessive CO2 emissions which LG2F avoids by not using steam in the reaction. The amount of methane to consider merging into the R1 feedstream is driven by the ratio of C2+ compounds vs. methane, the tradeoff of capital vs. reduced and the sizing of the LG2F process. Any excess quantities of methane can be regulated during this pre-processing step and diverted at any point (e.g. via slit-stream) to be reused elsewhere, thereby assuring the ratio of the C2-C5 alkanes to methane is preferably >1.0:1.0 in the fresh feedstream or merged recycle feedsteam before passing this into the R1 Thermal Olefination reactor.

The availability of such C2+ alkane-rich feedstreams with or without methane may depend upon local oil & gas processing alternatives and ever-changing market economics. Accordingly, this invention identifies a unique method to prepare a C2+ alkane-rich feedstream for R1 processing by merging the two primary outputs of a typical wet-gas demethanizer unit, but in a specialized design called "C2Rich". This method calls for utilizing two feedstream—all or any portion of a C1+ vaporous methane stream (e.g. using the preprocessed "wet gas" or using the demethanized "dry gas" comprised of methane and ethane) as the Vapor Feed, and any demethanized C2+ alkane liquid stream (sometimes referred to as y-grade product) as the Liquid Feed. Then the Vapor Feed and the Liquid Feed are passed

TABLE X

Impact of Increased Methane on Net Olefin Yield

| | Impact of Methane on R1 Reaction | Base Methane | 1.5X Methane | 2X Methane | 2.5X Methane |
|---|---|---|---|---|---|
| IN | TOTAL FEED (lb/hr) | 1574 | 1666 | 1757 | 1849 |
| | Hydrogen Feed (lb/hr) | 11.4 | 11.4 | 11.4 | 11.4 |
| | Methane Feed (lb/hr) | 183.4 | 275.2 | 366.9 | 458.6 |
| | Ethane Feed (lb/hr) | 1022.2 | 1022.2 | 1022.2 | 1022.2 |
| | C3+ Feed lb/hr (Propane, i-Butane, n-Butane) | 356.9 | 356.9 | 356.9 | 356.9 |
| — | Ethane Consumed = Feed − Avg Out (lb/hr) | 558.5 | 549.6 | 545.5 | 540.0 |
| OUT | Unreacted Methane (lb/hr) | 183.4 | 275.2 | 366.9 | 458.6 |
| | Unreacted Ethane Out (avg) (lb/hr) | 463.7 | 472.6 | 476.7 | 482.2 |
| | New Methane Produced (lb/hr) | 209.8 | 200.6 | 192.2 | 184.7 |
| | Ethylene Production (lb/hr) | 584.6 | 591.4 | 596.7 | 600.4 |
| | Ethylene/Net Ethane Consumed | 105% | 108% | 109% | 111% |
| | Olefin Production (lb/hr) | 656.4 | 664.4 | 671.0 | 676.2 |
| | Olefins/Net Ethane Consumed | 118% | 121% | 123% | 125% |

In addition, the increased use of methane reduces the formation of carbon coke and thereby extends the operating horizon of the R1 reactor. In one simulation model calculation, the operational run length increased up to 25% (from 64 to 80 operating days) between R1 regeneration cycles.

into a single-stage gas stripper operating at a temperature and pressure to produce a) a heavier C1+ natural gas effluent stream with a greater proportion of ethane (C2Rich Tops) and b) a new comingled blend of heavier alkanes which now has a reduced quantity of ethane (Bottoms). This C2Rich

TABLE X

Impact of Increased Methane on Carbon Buildup/Regeneration

| | Impact of Methane on R1 Reaction | Base Methane | 1.5X Methane | 2X Methane | 2.5X Methane |
|---|---|---|---|---|---|
| COKE | Coking Rate (mm/d) | 0.35 | 0.31 | 0.29 | 0.27 |
| | Estimated Runlength (days) | 64 | 70 | 74 | 80 |
| | # Decokes/yr | 5.5 | 5.1 | 4.8 | 4.5 |
| | Decoke Days Down/yr | 11.1 | 10.1 | 9.6 | 8.9 | output stream may also include methane in any amount from 0% up to 50% (wt.) of this total newly comingled stream. (For those skilled in the art of gas processing, there is no requirement that the C1+ vapor stream or the C2+ liquid stream are produced from a demethanizer unit or that they are even from the same gas-processing source. The goal is to eliminate capital intensive cryogenic processing, refrigeration and complex multi-stage fractionation steps.)

The C2Rich gas stripper passes the C1+ vapor phase natural gases and C2+ condensable liquids past each other in a counter-current fashion to intermingle and separate in order to a) selectively capture residual ethane and increase its concentration preferably >50% in the methane stream making it C2Rich, b) removing some portion of the ethane in the liquid stream (known as rejected ethane) leaving a heavier product stream by using the mixed-phase action of the gas stripper, c) return any unused or unneeded methane to the natural gas source or utilize for alternate use, d) optionally knockout any condensed heavy liquids (e.g. C4+) from the gas stripper liquid effluent for alternate commercial use. The resulting C2Rich vapor stream from the gas stripping step is then comprised of 0% to 50% (wt) methane and 50% to 100% (wt) C2+ alkane compounds for feed into the Thermal Olefination R1 reactor. This method avoids the use of cryogenics or complex fractionation to extract the desired ethane components needed for the C2+ feedstream to R1, thereby reducing capital investment. This method is also more efficient than processing traditional "wet gas" (pre-demethanizer which may contain only 5-20% C2+ hydrocarbons) because the use of a controllable slit-stream of C1+ vapors allows for efficient use of the methane gas stream during volatile market conditions without having to handle the entire "wet gas" or "dry gas" methane gas stream in the Thermal Olefination reaction. The gas stripper provides a method to regulate an ever-changing volume and composition of vapor and liquid phase feedstreams. The preferred choice for R1 feedstream may be the "top" of the stripper output as shown in case #2 or #3. This stripping method does not use cryogenics or refrigeration or complex multi-stage fractionation as these temperatures shown are a function solely of evaporation.

TABLE X

Gas Stripper Tailoring C2 + Methane for R1

| Mass % | | | Case 1 | Case 2 | Case 3 |
|---|---|---|---|---|---|
| Feed | Vap. | C1 | 88% | 93% | 96% |
| | | C2 | 12% | 7% | 4% |
| | Liq. | C2 | 10% | 35% | 61% |
| | | C3+ | 90% | 65% | 39% |
| Strip Out | Top | C1 | 28% | 20% | 6% |
| | | C2 | 23% | 52% | 76% |
| | Bot. | C2 | 5% | 16% | 34% |
| | | C3+ | 86% | 78% | 57% |
| Pressure (PSI) | | | 425 | 400 | 400 |
| Feed Temp (C.) | | | 25 | 25 | 25 |
| Top Temp (C.) | | | 29 | 16 | 19 |
| Bot Temp (C.) | | | −6 | −25 | −28 |
| Vap Feed (Lb/hr) | | | 800 | 400 | 138 |
| Liq Feed (Lb/hr) | | | 4800 | 2400 | 1650 |
| Top Out (Lb/hr) | | | 1661 | 1165 | 950 |
| Bot Out (Lb/hr) | | | 3939 | 1635 | 839 |
| Total Top C2 (Lb/hr) | | | 377 | 605 | 719 |

In a preferred embodiment, a C1+ natural gas steam containing 85-95% methane and 5-15% ethane enters a gas stripping reactor simultaneously with a y-grade or demethanized product ranging from about 5-60% ethane plus heavier C3+ alkanes. The two streams interact in the stripper at 400 psi and 25° C. and the resulting C1+ light gases (C2Rich Tops) from the light ends have an increased ethane content and the resulting liquid effluent exiting the bottom of the stripper has correspondingly decreased its content of ethane. In addition, the C2Rich tops effluent has been comingled with a variable portion of C1+ methane gas ranging from 5% to about 35% (wt) from the natural gas stream using a control valve to compensate for changing conditions for use in LG2F. This methane serves as a diluent in the LG2F reaction processes and to reduce metallurgical corrosion in R1. Using this unique hydrocarbon recovery method maximizes the capture of low-cost ethane for use in LG2F while avoiding the use of a deethanizer and it avoids capital-intensive cryogenic processing, refrigeration and complex fractionation methods which are typically necessary in such gas processing operations. This C2Rich comingled alkane blend is then passed into the R1 thermal olefination reactor as described in this LG2F invention to produce a range of gasoline grade and diesel grade fuel products. The C2+ heavier liquid stream exiting the stripper (also called y-grade) now has a higher value per gallon due to the reduction of the lighter ethane molecules.

In another embodiment, the C1+ natural gas stream is a desulfurized wet-gas stream containing >80% methane, and a different C2+ light alkane stream (a y-grade stream, e.g. exiting a demethanizer), are passed in a multi-cycle gas stripper process augmented with a methane membrane unit. The methane and C2Rich light gases extracted from the top of the stripper now have a higher concentration of ethane (greater than methane) and are used as low-cost feedstream to the R1 Thermal Olefination process. The C2+ bottoms y-grade effluent is available for any alternate use, albeit at a higher value per gallon due to the ethane extraction process.

In another embodiment, a demethanizer is configured to add a single or multi-stage gas stripper module that allows wet gas or dry gas and any demethanized C2+ alkanes to converge and interact so as to strip a controlled portion of C2 light hydrocarbons into the C2Rich (tops) stream and a heaver y-grade effluent without the additional of any cryogenic processes. The C2Rich light hydrocarbons may contain any amount of methane but preferably from 0% up to 35% (wt), plus about 50%-90% ethane, and 0% up to about 15% propane of the C1+ light alkane stream. This C1+ stream then passes to the R1 Thermal Olefination reaction for further LG2F processing.

C2-5 Olefin Catalytic Processing

The Thermal Olefination results in a product stream which is passed to a catalytic reactor in which the olefins are converted into a broad spectrum of fuel grade hydrocarbons. The conversion involves chemical reactions comprising cracking, oligomerization and/or aromatic cyclization, and transforms the olefins without affecting lighter (C2/C3) paraffins in the Feedstream. In one sense, the catalytic conversion may be affected in any manner known in the art to be effective in cracking, oligomerizing and/or cyclizing C2-5 olefins. Particularly preferred catalytic processes are disclosed herein.

As used herein, the term "Olefin Feedstream" refers to a Feedstream comprising C2-5 olefins. The Olefin Feedstream may comprise all or a portion of the product stream of the Thermal Olefination reactor. For example, methane and hydrogen present in the olefination product may be separated prior to passing the stream to the catalytic reactor. Or alternatively, methane and hydrogen may be fed into the catalytic process, serving to help manage the isothermal 2reaction of the R2 reactor(s). Similarly, C2-5 Alkanes present in the product stream, particularly ethane and propane, may be separated out and recycled to the Thermal Olefination reactor at any point in the LG2F process—either combined with the C2-5 Alkane Feedstream, or separately. An Olefin Feedstream derived from the product stream of the Thermal Olefination reactor will contain C2-5 olefins.

In one aspect, the C2-5 Olefin Feedstream is input to the catalytic reactor. As used herein, the term "catalytic reactor" is used to refer to a reactor using a zeolite catalyst and operating under controlled conditions so as to cause cracking, oligomerizing, dimerizing, trimerizing and, in many conditions, cyclizing of the feed olefins to form higher carbon alkanes, alkenes and aromatics suitable for gas or diesel blending stocks. The use of zeolites as a three-dimensional crystalline structure is the preferred catalyst in all LG2F oligomerization reactions, but variations of the zeolite support structures using metalloids and post-transition metals may be used individually or in combinations in a given R2 reactor designed to maximize the commercial outcome of the LG2F oligomerization process. In addition, the LG2F process may use a multi-step oligomerization reaction sequence described herein for producing longer-chain molecules by operating first at low pressure (gas phase) and then condensing the effluent to a liquid for a second high pressure reaction, coupled with the use of single or multi-catalyst processing techniques offering a range of unique combinations to produce many specialized high-performance fuel grades, fuel blendstocks and base chemical feedstocks.

It will be appreciated that these reactions may occur in various combinations and orders, with some molecules undergoing several such reactions. Thus, reactions leading to the end products may act on the olefins in the feed, or may act on the olefins after they have already undergone one or more reactions. It is therefore contemplated, and is to be understood, that reference to reactions of the feed olefins refers generally to reaction of any molecule that was originally fed to the catalytic reactor as a C2-5 olefin.

The catalytic reactor uses a zeolite catalyst and operates above 200° C., at 0-1500 psig, and a weight hourly space velocity (WHSV) between 0.5 and 10 (preferably about 1). This reactor produces multi-iterative, random-sequenced chemical reactions to crack, oligomerize, and in many conditions, cyclize the broad-spectrum of hydrocarbons comprising olefins and olefin-derived compounds. The catalytic process can be caused to produce any range of fuel grade products, including for example, $C_{5+}$ or $C_{6+}$ or $C_{7+}$ gasoline ranges (primarily paraffins, olefins, and aromatics), or $C_{9+}$ or $C_{10+}$ or $C_{12+}$ ranges of light gas oil or middle distillate hydrocarbons (for use primarily as diesel fuel blendstocks).

The chemical reactions in the catalytic reactor (R2) comprise multi-iterative, building, degrading and sometimes cyclizing of different molecular formations creating a portfolio of hydrocarbons that can be selectively tailored to any specific carbon range of products. The end products can be affected, for example, based on the composition of the C2-5 Alkane Feedstream, the configuration of a recycle loop, and various other operating conditions of the overall LG2F Process. For example, operating conditions (e.g., T, P, WHSV) are varied depending upon the desired product—gasoline grade or middle distillate grade fuel blendstocks.

Catalysts

The catalytic reactions disclosed herein utilize catalysts in the R2 reactor(s) that crack, oligomerize, dimerize, trimerize and in many conditions cyclize the olefin feedstream with high efficiency. The catalysts used in the preferred embodiments of LG2F Process generally contains a strongly acidic (non-metallic) zeolite, with a high surface area support, for example, alumina.

Over the past several decades, the oligomerization of alkenes has involved the use of many types of catalysts to produce fuels. Examples of such catalysts include:

Heterogenous acid catalysts (primarily zeolites; preferable ZSM-5)

Dealuminated acid catalysts (zeolites) in proton form to dimerize olefins

Heterogenous nickel catalysts (to dimerize light olefins)

Homogeneous nickel catalysts (to dimerize or to produce long-chain linear oligomers)

Bi-functional catalysts using various metals (e.g. Co, Cu, Pt, Pd, Fe, Rh, Ir, Ru, Ta, Zn, Ga, In, Al, K, etc.) incorporated into heterogenous acid catalysts As anyone skilled in the art of catalysis knows that any of these catalytic methods or combinations thereof could be used in the LG2F oligomerization process under the proper temperature, pressure, and space velocity to produce a viable fuel or fuel blendstocks. Hence all these catalytic methods are hereby incorporated into this invention. (Reference: Alkene Oligomerization, C. T. O'Connor, Dept of Chemical Engineering, UCT, S. Africa, 1990; n-butene skeletal isomerization to isobutylene—Ferrierite/ZSM-35, Wen-Qing Xu, et. al. University of Connecticut, 1995; Conversion of n-Butane to iso-Butene on Gallium/HZ SM-5 catalysts, S. M. Gheno, et al., Dept de Engenharia Quimica, Sao Paulo Brazil, 2001; U.S. Pat. Nos. 3,325,465, 6,852,901, 6,914,166)

In some selected embodiments, the addition of the metalloid Boron (B), utilized with a ZSM-5 structure in a specialized synthesis process, greatly increases the number of crystals supported in the catalytic structure without limiting the pore size. This Boron-enhanced non-metallic zeolite structure with Boron >5 wt. % of the catalyst and Si/Al≥500, herein called "ZSM-5B", reduces activation and allows a more controlled dimerization and trimerization of olefin compounds when processing R1 effluent or any light olefin-containing feed stream, particularly any stream comprised of C2 or C3 olefinic compounds. Other experimental lab testing of ZSM-5 structures using >5% Boron substituted alumina with metalloid germanium and non-metallic phosphorus and found all three to be similar in their effectiveness at dimerizing ethylene. The use of the ZSM-5B catalyst in such an R2 reactor results in the intermediate production of effluent comprised of C4+ or C6+ olefins as a precursor to further downstream R2 catalytic conversions. The preferred embodiments of utilizing the ZSM-5B catalyst were found when operating a first R2 catalytic reactor with the ZSM-5B catalyst operating at low temperatures (about 250 to 400 C) and low pressures (about 0 to 300 psig) with limited reaction time thereby producing dimerized and trimerized olefins. This reaction was then followed by a high-pressure liquification step (via pump or compression) to concentrate the intermediate olefin-containing feedstream, followed by secondary R2 reaction using a non-metallic zeolite (with or without the use of ZSM-5B) operating at any appropriate pressure and temperature to produce a targeted range of longer-chain hydrocarbons particularly useful in the production of middle distillate fuel.

The initial production of the ZSM-5B catalyst outlined herein was developed using the follow laboratory procedures: 1) Ethylenediamine (80 mL) and Boric Acid (49.46 g) were added to water (735.07 g) and stirred for 15 min, 2)

Aluminum Nitrate Nonahydrate (6.00 g) and Tetrapropylammonium Bromide (21.31 g) were added to the mixture and stirred for 15 min., 3) Colloidal Silica (Ludox HS-40, 601.8 g) was added and stirred for 30 min. before transferring entire mixture to a 2-L autoclave with a Teflon cup. The mixture continued stirring at ambient conditions as the autoclave heated up, 4) The autoclave was set to heat at 175° C. and left for 132 hours, 5) After cooling down, solid products were recovered by decanting off the liquid. Solids were washed, alternating between water and acetone, 3 times each. Solids were recovered by decantation, 6) The wet solids were transferred to glass containers and placed in a 70° C. oven for 48 h. The oven temperature was increased to 100° C. for 24 h. Then increased again to 120° C. for 6 h, 7) Solids are calcined at 580° C. for 10 h to remove residual organics, 8) B—Al-MFI are converted to NH4-form by ion-exchange using a 1.0 M Ammonium Nitrate solution, then washed four times with water, 9) NH4-form zeolites are converted to H-form by heating in air at 500° C. Subsequent versions of the catalyst were prepared and tested to reduce activation, lower benzene content, lower total aromatic content and other tailorable fuel attributes.

In traditional hydrothermal synthesis of zeolites, the crystallite size is generally linked to the amount of aluminum heteroatoms; lower amounts of Al results in larger crystallite sizes. Large crystallite sizes are problematic for the LG2F R2 reaction for a variety of reasons such as diffusion issues and increased residence time inside the crystal, which can result in undesired secondary reactions and catalyst deactivation. Incorporation of ≥5% wt. non-catalytic boron heteroatoms during synthesis allows for independent control of crystallite size. At various low Al concentrations as illustrated below, increasing amounts of B yielded smaller crystallites. This allows for the synthesis of zeolites with low active-site concentrations (i.e. low Al) while avoiding the issues associated with large crystallite sizes.

The derivation of the ZSM-5B catalyst is outlined below as follows using a SUB ratio of 2.5:1. All the variations of ZSM-5B catalysts tested had a Boron weight ≥5% wt.

|  |  |  |  |  |
|---|---|---|---|---|
|  | Si | $O_2$ = |  | Silica (Silicone Dioxide) |
| $Si_{2.5}$ | B | $O_7$ = |  | Zeolite w/Boron (no Al) |
| $Si_{2.5}$ | B | $O_7$ | $Al_{0.xxxx}$ = | Zeolite w/Boron (with Alumina) |

| Alumina (wt %) per 2.5 units of Silica (Assuming Si/B = 2.5) | | | | | | | | | |
|---|---|---|---|---|---|---|---|---|---|
| Si/Al = 200 | | Si/Al = 333 | | Si/Al = 500 | | Si/Al = 750 | | Si/Al = 1000 | |
| Si | 2.5 | Si | 2.5 | Si | 2.5 | Si | 2.5 | Si | 2.5 |
| Al | 0.0125 | Al | 0.0075 | Al | 0.0050 | Al | 0.0033 | Al | 0.0025 |

|  | Si | B | O | Al |  |  |
|---|---|---|---|---|---|---|
| Atomic Wt. | 28.1 | 10.8 | 16 | 27 |  |  |
|  |  |  |  |  |  | Boron |
| Si/Al Ratio | $Si_{2.5}$ | B | $O_7$ | $Al_{0.xxxx}$ | Total Wt. | (% wt) |
| Si/Al = 200 | 70.25 | 10.8 | 112 | 0.3375 | 193.3875 | 5.585% |
| Si/Al = 333 | 70.25 | 10.8 | 112 | 0.2027 | 193.2527 | 5.589% |
| Si/Al = 500 | 70.25 | 10.8 | 112 | 0.1350 | 193.1850 | 5.590% |
| Si/Al = 750 | 70.25 | 10.8 | 112 | 0.0900 | 193.1400 | 5.592% |
| Si/Al = 1000 | 70.25 | 10.8 | 112 | 0.0675 | 193.1175 | 5.592% |

In one lab experiment of the Boron catalyst shown above, the liquid product from reacting C3= (propylene) with the BCat (Si/Al≈500, Si/B≈2.5) was run in a reactor. The resulting data shows a liquid rich in C4, C5, C6 and C7 olefin compounds, which has a density of 0.70 g/mL. This case demonstrates the effectiveness of the dimerization and trimerization process using Boron by slowing the activation process. The example here was obtained at 40 psig, reactor temperature of 300° C., and propylene flow of 5 WHSV.

| C3 = --> Dimers/Trimers R2 Dimerization | |
|---|---|
|  | Wt % |
| C1-C4 | 13.96 |
| C5 | 19.47 |
| C6 | 17.32 |
| C6AR | 0.10 |
| C7 | 18.97 |
| C7AR | 0.69 |
| C8 | 12.76 |
| C8AR | 1.66 |
| C9 | 6.22 |
| C9 AR | 1.57 |
| C10 | 2.85 |
| C10 AR | 0.96 |
| C11 | 0.63 |
| C11 AR | 0.00 |
| C12+/Unknown | 2.85 |
|  | 100.00 |

In a follow-up experiment, taking the liquid effluent produced above and reacting it over a regular ZSM-5 (80:1). This is GC/MS data to get info on the heavier compounds and shows a lot of heavier olefinic compounds—typical of diesel fuel. The attached data shows the chromatogram for this product. Approximately 80% of the product is C8 and up when using the C2-C5 recycle process. The liquid product had a density of 0.75 g/ml. For this reaction, the reactor pressure was 330 psig, a set point of 225° C., and flow at 3.5 WHSV. This product output is well within the range of typical diesel fuel products.

| R2 Oligomerization Reaction #2 (target Diesel) | | | |
|---|---|---|---|
|  | GCMS Area % | Recycle Options | Two Fuel Products |
| C3 | 0.19 | Recycle R2-Low P | Recycle R2-Low P |
| C4 | 1.65 | Recycle R2-Low P | Recycle R2-Low P |
| C5 | 4.18 | Recycle R2-High P | Gasoline |
| C6 | 6.04 | Recycle R2-High P | Gasoline |
| C7 | 7.25 | Recycle R2-High P | Gasoline |
| C8 | 10.64 | Recycle R2-High P | Gasoline |
| C9 | 8.95 | Diesel | Gasoline |
| C10 | 7.91 | Diesel | Gasoline |
| C11 | 7.57 | Diesel | Diesel |

-continued

R2 Oligomerization Reaction #2 (target Diesel)

| | GCMS Area % | Recycle Options | Two Fuel Products |
|---|---|---|---|
| C12 | 7.86 | Diesel | Diesel |
| C13 | 6.59 | Diesel | Diesel |
| C14 | 7.08 | Diesel | Diesel |
| C15 | 1.66 | Diesel | Diesel |
| C16 | 6.08 | Diesel | Diesel |
| C17 | 2.08 | Diesel | Diesel |
| C18 | 4.37 | Diesel | Diesel |
| C18+ | 9.90 | Diesel | Diesel |
| | 100.00 | | |

In one embodiment, the olefin effluent from the first low pressure R2 reactor processed using the ZSM-5B catalyst contains dimerized C4+ olefins which are then further oligomerized in a high pressure R2 reactor using a different combination of zeolite catalysts. The effluent of the high-pressure reaction is split between C5-C9 grade gasoline compounds and C10+ distillate grade compounds with the C2-C4 residual being recycled. In another embodiment, the C2-C8 portion of the high pressure R2 reactor effluent is recycled back to the inlet of the high-pressure R2 reaction to create more long-chain compounds. In another embodiment, the C2-C4 olefins from the effluent of the high pressure R2 reaction are recycled back to the low pressure gas-phase R2 reaction for re-dimerization, and the C5-C8 portion of the high pressure effluent is recycled to the inlet of the high pressure R2 oligomerization process to support the making of longer chain molecules.

Additionally, in selected embodiments involving the production of high aromatic compounds (e,g, pygas, toluene, LG2F pseudo-reformate, BTX, etc.), there may be a weakly active metal as outlined in earlier research, for example Pt, Pd, Re, Rh, Ir, or Mo, which may be utilized in any R2 reactor, either staged within the reactor downstream of a non-metallic zeolite catalyst or used in some sequence as a standalone R2 reactor, to saturate cracked olefins and/or hydrodealkylate cyclized aromatic compounds to produce methyl-aromatics using the R2C9 process (invented by inventor), which may be desirable in a specialized spectrum of targeted fuels or base chemicals. If utilized, these catalyst metals may be present as an oxide, metallic or alloy nano-particles. The preferred metals are Pt, Re and Mo operating at temperatures between 200-500 C at pressures from 0 to 1500 psig and a space velocity from 0.1 to 10 $hr^{-1}$. The metal loading can be from 0.05 to about 10 wt. % as metal impregnated in the catalyst. The metals are typically supported on a high surface area support such as alumina, silica, and other refractory oxides. These oxides provide high surface area, porosity and physical strength. The oxide support also contains an acidic form of zeolite Y(FAU), beta (BEA), mordenite (MOR), and ZSM-5 (MFI). The amount of zeolite may be from 10% to 90% wt. of the finished catalyst.

The LG2F Process uses any catalyst or combination of catalysts in the R2 reactor(s) which are functional to substantially crack, oligomerize, dimerize, trimerize and under some conditions cyclize the olefins in the feedstream. A catalyst is functional to substantially crack, oligomerize, and/or cyclize the olefins if it transforms at least 65%, preferably at least 80%, and more preferably at least 95% of the olefins to fuel grade compounds in a single-pass conversion. In selected embodiments, the reactions are accomplished by a two-step R2 zeolite reaction whereby C2+ olefins (e.g. ethene, propene) are initially dimerized and trimerized in an abbreviated (rapid) low-severity reaction using a ZSM-5B catalyst to limit the production of longer-chain molecules and this effluent comprising any C4+ or C6+ olefins is subsequently concentrated into a high-pressure liquid before entering another R2 vapor-phase reaction with a zeolite catalyst but at various temperatures and pressures that depend upon the desired product slate. This second R2 reaction when used along with a liquid/vapor flash drum and a recycle loop back to R1 can better control the production of longer-chain molecules (generally ≥C9 hydrocarbons) due to its thermodynamic stability (from less exothermic activity) for more tailored fuel products particularly in the middle distillate range.

In one embodiment, the catalytic reaction is performed using a zeolite catalyst. The acidic sites in zeolite catalyze cracking reactions more rapidly than other components. These reactions are conducted without metal impregnation to eliminate the undesired production of propane caused from hydrogen/metal reactions at higher temperatures. In another embodiment, the zeolite catalyst is used in the R2 reactor in combination with a metal impregnated zeolite to specifically hydrogenate unreacted olefins at temperatures below about 275 C to improve the targeted fuel characteristics.

In one aspect, the processes use a zeolite catalyst having a pore size of 2 to 8 Angstroms. Exemplary surface areas for the catalyst are 400 to 800 $m^2$/gram. Examples of the zeolite catalysts include Si, Al and O, preferably with an Si:Al ratio of 3 to 560. Zeolite catalysts with properties outside of these limitations may also be useful. The catalyst is preferably selected to substantially catalyze the olefins while not significantly affecting other components of value in the feed stream.

In embodiments, the catalyst is Zeolite ZSM-5, Zeolite Beta, Zeolite-Y or Zeolite Mordenite. Zeolites are characterized in the following ways: pore size—3 to 8 angstroms usually; pore structure—many types; and chemical structure—combination of Si, Al, and O. All have ammonium cations (except one version of mordenite) prior to any impregnation and all have molar Si/Al ratios of 3 to 560.

Zeolite Beta has the following properties: 2-7 angstroms pore size, SiO2 to Al2O3 molar ratio (Si/Al) ranging from 10 to 150, intergrowth of polymorph A and B structures, and surface area between 600 and 800 $m^2$/gram.

Zeolite-Y has the following properties: averaging 7-8 angstroms pore size, SiO2 to Al2O3 molar ratio (Si/Al) greater than 3, and surface area between 600 and 1000 m2/gram.

Zeolite Mordenite has the following properties: 2-8 angstroms pore size, sodium and ammonium nominal cation forms, Si/Al ratio of 10 to 30, and surface area between 400 and 600 m2/gram.

In a particular embodiment, the catalyst is Zeolite ZSM-5. ZSM-5 has the following properties: 4-6 angstroms pore size, pentasil geometry forming a 10-ring-hole configuration, Si/Al ratio of 20 to 560, and surface area between 400 and 500 $m^2$/gram. The ZSM-5 is the preferred catalyst for its ability to support the R2 transformation reaction to produce fuel grade gasoline and diesel products. The smaller pore size of the ZSM-5 catalyst results in far less undesired saturation, coking and deactivation. This preferred reaction is conducted without metal impregnation. However, in some specialized embodiments, a metal impregnated zeolite used downstream of a non-metallic zeolite allows hydrogen (e.g.

R1-produced hydrogen) to add across olefinic compounds which may produce a more desired result for some selected fuel grades.

Zeolite Catalyst Example

In one embodiment, the proprietary acid-based ZSM-5 zeolite catalyst specifically targets $C_2$-rich hydrocarbon streams (e.g., one embodiment: 80:1 silica on alumina ratio). The process design may also have catalyst beds which favor $C_2$ reactions more than $C_3$ reactions or $C_4$ reactions, etc., resulting in layers or sequences of oligomerization, dimerizing, trimerizing and cracking reactions with different conditions to maximize the yield and performance properties of the fuel products.

The R2 reactor design is tailored to mitigate the tendency of the chemical reaction to generate a highly exothermic response during the oligomerization process. The design considers the impact of isothermal vs. adiabatic methods. In one embodiment, the R2 reactor design is tailored as an isothermal reaction with intermittent heat and cooling applied to manage steady-state temperatures. In another embodiment, the R2 reactor design is tailored to utilize a combination of the isothermal method and adiabatic methods. In another embodiment, the R2 reactor design utilizes a unique cooling feature of the inner core of the reactor to stabilize the response to exothermic reactions.

The R2 reactor design may also utilize a variety of methods to support the regeneration of its catalysts. In one embodiment, a series of R2 reactors is used to alternate between active oligomerization processing and offline catalyst regeneration processing. In the preferred embodiment, the R2 reactor design utilizes a fluidized bed-style reactor with a continuous regeneration process employed to refresh the catalyst with sufficient turbidity and stabilized heat management without interrupting the process flow. In another embodiment, the R2 reactor design utilizes a static bed in combination with a fluidized bed reaction method to minimize latent heat and thereby reduce the utility cost of the reactor. In yet another embodiment, the R2 reactor design utilizes a static bed plug flow method is the lowest cost method due to no moving parts thereby offering a more predictable management of contact time between the flow and the catalyst. Other reactor designs known to those skilled in the art of catalytic processing are included in the available range of reactor designs for the R2 oligomerization process.

Reactor Regeneration—R2

Operability of the catalytic reactor is dependent upon reactor and catalyst life-cycles, and the resulting amount of deactivation or thermal resistance that may occur from carbon build-up on catalysts or reactor walls. Regeneration of any such reactor or catalyst operating at high temperatures involves a unique series of steps to restore active levels and prevent permanent catalytic deactivation of the downstream zeolite-based catalytic reactor. It has been determined that the regeneration methods previously described herein are also useful with the R2 catalytic reactor(s), and the timing of regeneration may be determined on a similar basis.

Both regeneration methods outlined herein can be tailored to operate in any suitable reactor, especially any Thermal Olefination reactor or any zeolite based catalytic reactor. For the R2 reactor(s) these methods beneficially restore the catalytic activity of the zeolite with the advantage of eliminating loss of active sites caused by traditional steam cracking methods resulting in steam dealumination.

LG2F System

Figure 3:
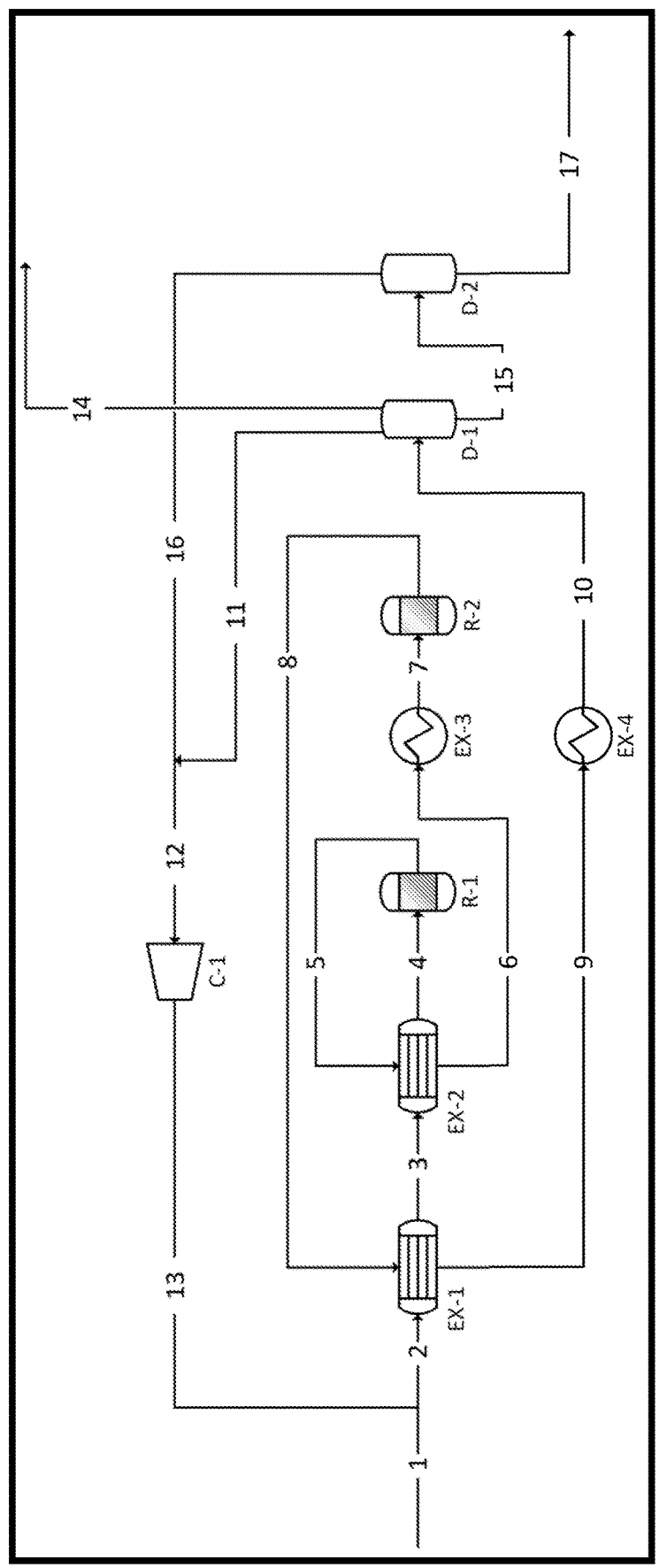
FIG. 3 is a more detailed flow diagram of an embodiment of the Light Gas to Fuels Process (the "LG2F Process").

Referring to FIG. 3, there is shown a process flow for the LG2F Process. Feedstock stream (1) comprises mostly C2-C5 paraffin-rich alkanes. Pretreatment (not shown) of the feed (1) can be conducted to remove excess methane if necessary (via membrane system or purging), C6+ hydrocarbons (via liquid-vapor flash drum), or any contaminants to support gasoline and diesel fuel production and/or to optimize feed composition. Feedstock stream (1) is combined with a recycled light stream (13) comprised of a $C_1$-$C_5$ mixture primarily including n-paraffins and i-paraffins with some olefins and the combined stream (2) is fed into heat exchanger (EX-1). As described later, light gas feedstreams that have primarily olefin-rich content (e.g., FCC off-gases, propylene, etc.) may be fed directly into R-2 via line (7), bypassing the Thermal Olefination step. The combined stream (2) is cross exchanged in EX-1 with stream (8), to recover heat produced in the catalytic reactor R-2. The outlet stream (3) of EX-1 is fed into another cross exchanger, EX-2, to further pre-heat the feed for R-1.

The pre-heated stream (4) is fed into a Thermal Olefination furnace (R-1) typically operating at 600-1100° C. and 0-1500 psig. Thermal Olefination reactor (R-1) conducts an endothermic reaction to produce olefinic compounds via carbon cracking and dehydrogenation. Excess heat from the reaction is used as the hot stream (5) for EX-2. The hot stream (6) exiting EX-2 may require additional cooling for the second reaction stage (R-2). EX-3 is an optional air-water or refrigerant-based cooling unit for the system depending upon heating requirements. It is useful here to conduct the appropriate heat transfer step to ensure proper set-point R-2 inlet conditions. A bypass can be implemented between streams (6) and (7) and streams (9) and (10) in lieu of cooling utility for EX-3 and EX-4 for dynamic operability between diesel and gasoline production. An optional knock-out step may be incorporated prior to the R-2 reactor in stream (7) to capture entrained liquid droplets and remove all C6+ compounds from entering R-2. See FIG. 4.

R-2 is catalytic reactor, typically operating at 200-1000° C. and 0-1500 psig, that cracks, oligomerizes, and under some conditions cyclizes olefinic compounds in multi-iterative reactions to produce a broad spectrum of n-paraffins, i-paraffins, naphthenes, and aromatics primarily across the $C_4$ to $C_{16+}$ range, resulting in high-octane gasoline or high-cetane diesel spectrum products. Depending upon the final product desired, excess $C_2$ to $C_{12}$ compounds from this catalytic reaction can be recycled into fuel grade constituents. The reaction is very exothermic and can be configured with or without inter-stage or integrated cooling to prevent overheating. The excess heat from the reacted stream (8) is used in EX-1 as the hot stream inlet to step up temperature for the combined feed (2).

The hot outlet (9) can support optional cooling for proper flashing in flash drum D-1. For this reason, EX-4 may not be required but it could be an air-cooler, water cooler, etc. to conduct appropriate heat exchange. The flash drum feed (10) is kept at the pressure of the system and is used to purge targeted light components from the mixed product stream. The primary function of D-1 is to control the pressure of the system. Light components (11, 14) consist of mostly H2 and C1-C3 compounds that can either be purged (14) from the system or directly recycled (11) back into the system by combining with the flash drum (D-2) lights stream (16) prior to compressor, C-1.

D-1 light streams will have H2 and C1 components which are unreactive for the system and will cause accumulation in the recycle if not properly removed. H2 and C1 can be purged (14) with other light components to stabilize the recycle system or a separator, such as a membrane, can be utilized to selectively remove H2 and C1. The liquid bottoms (15) from D-1 are fed into D-2 which is set at a lower pressure to remove mostly C3 and C4 compounds from the liquid stream (15). Lights (16) from D-2 are combined with lights (11) from D-1 to form stream (12) which is compressed in C-1 and recycled for further reaction. Recyclable light hydrocarbons (16) from D-2 (typically $C_2$-$C_4$ if targeting gasoline; $C_2$-$C_{10}$ if targeting diesel) will be fed back to the thermal reaction, unless the constituents are olefin-rich which can optionally be fed directly into R-2 to increase process efficiency. The resulting flashed liquid stream (17) exiting the bottoms of D-2 is the final product of the process which can be targeted to produce any range of $C_4$-$C_{12}$ high-octane gasoline blendstock or $C_{9-16+}$ high-cetane diesel fuel blendstock.

Recycle

Following the R2 catalytic reaction, the alkane-rich light gas recycle stream exiting the flash drum condensation unit can be directed back to the $C_{2+}$ Thermal Olefination reactor to be merged with other incoming light hydrocarbon streams as depicted in the process flow FIG. 1. The constituents outside the selected array are gathered into a single-loop recycling configuration. This recycle process maximizes the yield profile and performance properties of any type of the liquid effluent produced for transportation fuel use. Typically, for all compounds not used in a targeted gasoline range or diesel fuel range the process will direct the lighter byproducts (e.g. ≤C5 for gasoline or ≤$C_8$ for diesel) to be recycled for further upgrading. Operating with a continuous recycle loop with R2 effluent achieves high product yields, for example ranging from 65% to 95%.

Each recycle loop is continuous to allow the random redistribution of $C_{6+}$ liquid hydrocarbons yielded from the LG2F Process to unite in various formations (e.g., paraffins, olefins, aromatics) needed for a fuel based upon specific performance characteristics. Such performance characteristics for gasoline might include octane, vapor pressure, density, net heat of combustion, etc., while such characteristics for diesel fuel might include cetane, thermal stability, cold flowability, and others.

Figure 4:
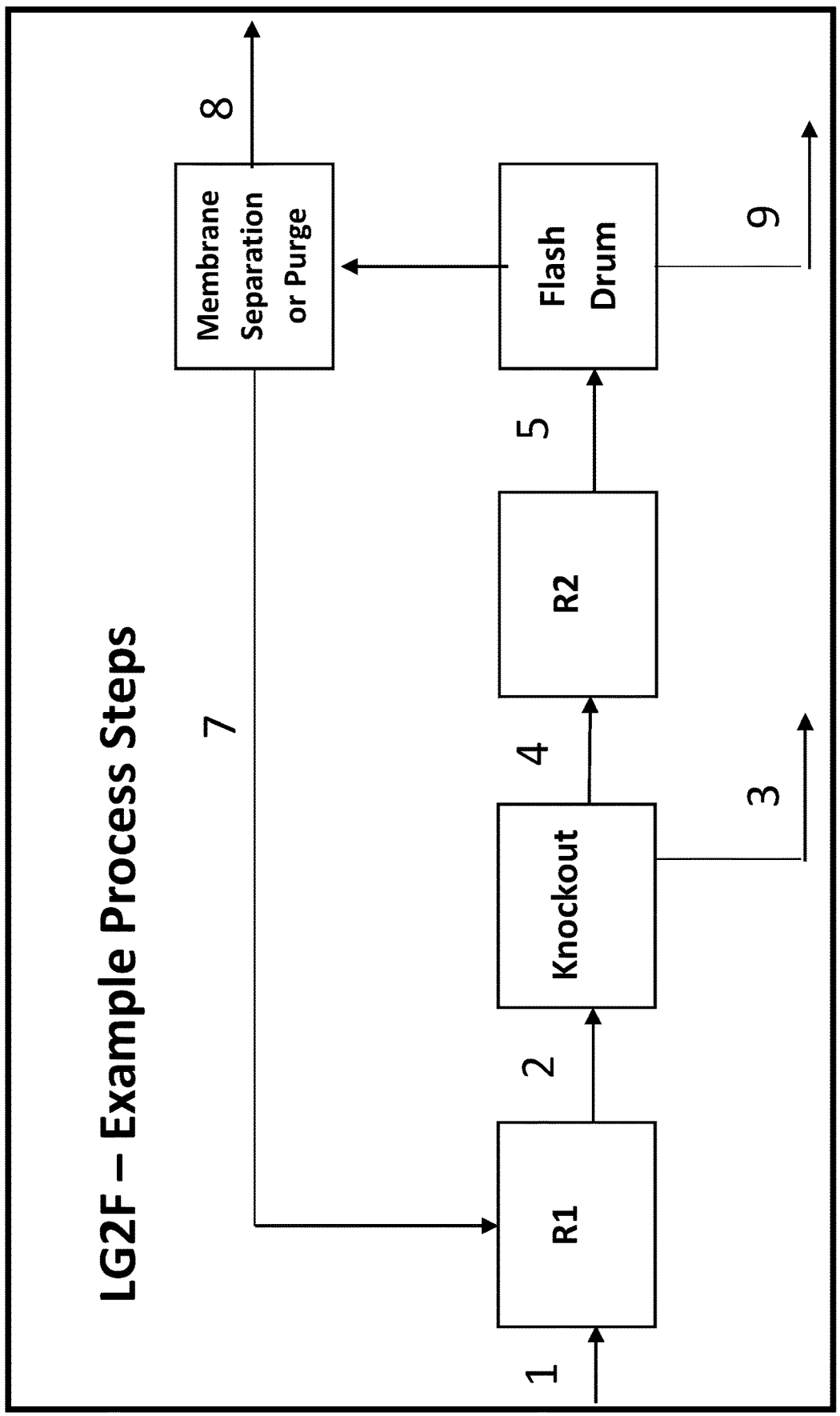
FIG. 4 is a simplified version of the flow diagram of FIG. 3, modified to include a Knockout Unit between the non-catalytic Thermal Olefination reactor ("R1") and the zeolite-catalytic reactor ("R2").

Referring to FIG. 4, there is shown a simplified schematic for an LG2F system in accordance with the present invention. The system is generally the same as shown in FIG. 3, except a "Knockout" is provided between reactors R1 and R2. As previously mentioned, the Knockout unit operates to remove entrained liquids and C6+ compounds from entering R2.

By way of example, the fully-recycled thermal and chemical reactions from processing a feed of 80% C2 (ethane) and 20% C5 (pentane) are depicted in a material balance as shown below in Table 3a. The process follows the steps in FIG. 4.

The resulting C6+ gasoline compounds yielded a 66% mass conversion of high-performance gasoline with a 25% (17/66% mass as aromatics) from the C2/C5 feed and resulted in an unexpectedly high 101.7 Research Octane number (using ASTM D2699 Test Method). This illustration using C2 and C5 as the feed to Thermal Olefination demonstrates the broad range of gasoline blend compositions that are possible.

TABLE 3a

Production of Gasoline Blendstock from C2 & C5 feedstock

| | \multicolumn{9}{c}{Process Step} |
|---|---|---|---|---|---|---|---|---|---|
| | 1 | 2 | 3 | 4 | 5 | 6 | 7 | 8 | 9 |
| | | | | | LG2F w/ C2 + C5 w Recycle Lb/hr | | | | |
| | Feed | R1 Out | Knockout | R2 Feed | R2 Out | Flash Tops | Recycle | Lights Purge | Gasoline |
| H2 | | 5.59 | | 5.59 | 5.59 | 5.59 | | 5.59 | |
| C1 | | 19.10 | | 19.10 | 19.11 | 19.11 | | 19.11 | |
| C2 | 80 | 148.82 | | 148.82 | 149.68 | 149.68 | 149.68 | | |
| C2= | | 75.43 | | 75.43 | 0.00 | | | | |
| C3 | | 0.65 | | 0.65 | 5.55 | 5.55 | 5.55 | | |
| C3= | | 9.54 | | 9.54 | 0.00 | | | | |
| C4 | | 0.61 | | 0.61 | 14.24 | 14.24 | 14.24 | | |
| C4= | | 2.21 | | 2.21 | 2.65 | 2.65 | 2.65 | | |
| C5 | 20 | 0.00 | | 0.00 | 14.27 | | | | 14.27 |
| C5= | | 0.97 | | 0.97 | 4.15 | | | | 4.15 |
| C6 | | 0.13 | | 0.13 | 11.19 | | | | 11.19 |
| C7 | | | | | 7.33 | | | | 7.33 |
| C8 | | | | | 6.01 | | | | 6.01 |
| C9 | | | | | 4.07 | | | | 4.07 |
| C10 | | | | | 1.46 | | | | 1.46 |
| C11 | | | | | 0.48 | | | | 0.48 |
| C12 | | | | | 0.61 | | | | 0.61 |
| A6 | | 4.83 | 4.83 | | 0.19 | | | | 0.19 |
| A7 | | 1.60 | 1.60 | | 1.45 | | | | 1.45 |
| A8 | | | | | 3.64 | | | | 3.64 |
| A9 | | | | | 5.45 | | | | 5.45 |
| A10 | | | | | 4.17 | | | | 4.17 |

TABLE 3a-continued

Production of Gasoline Blendstock from C2 & C5 feedstock

| | | | | | Process Step | | | | |
|---|---|---|---|---|---|---|---|---|---|
| | 1 | 2 | 3 | 4 | 5<br>LG2F w/<br>C2 + C5<br>w<br>Recycle Lb/hr | 6 | 7 | 8 | 9 |
| | Feed | R1 Out | Knockout | R2 Feed | R2 Out | Flash Tops | Recycle | Lights Purge | Gasoline |
| A11 | | | | | 0.94 | | | | 0.94 |
| Unknown | | 2.65 | 2.65 | | 0.82 | | | | 0.82 |
| Total | 100 | 272.13 | 9.08 | 263.05 | 263.05 | 196.82 | 172.12 | 24.69 | 66.23 |

A similar example shown in Table 3b depicts 100% C2 (ethane) with an 84% mass conversion to C5+ gasoline (for standard RVP) with a 25% (21/84% mass as aromatics) and a RON octane value of 93 and a vapor pressure of 11.6 psi. This demonstrates the broad spectrum of molecular outcomes typical of all C2-5 feedstreams. The $C_2$ to $C_5$ feedstocks can be fully recycled and converted to gasoline range molecules based upon the unique operating conditions of the reactor. The process follows the steps in FIG. 4.

resulted in a 25% m/m aromatic content. The aromatic content is variable and can be used to increase octane values of gasoline blendstocks. Surplus C6+ aromatics can be captured from the knockout as byproducts for petrochemical processing. Increasing the temperature of reactor 2 from 250° C. to 400° C. doubles the content of desirable aromatics in the gasoline blendstock and thereby increases the resulting octane. The lights purge (via flash drum and membrane separation) allows methane and hydrogen TABLE 3b Production of Premium Gasoline Blendstock from C2 (ethane) feedstock

| | | | | | Process Step | | | | |
|---|---|---|---|---|---|---|---|---|---|
| | 1 | 2 | 3 | 4 | 5<br>LG2F:<br>C2 w/<br>Recycle<br>Lb/hr | 6 | 7 | 8 | 9 |
| | Feed | R1 Out | Knockout | R2 Feed | R2 Out | Flash Tops | Recycle | Lights Purge | Gasoline |
| H2 | | 4.67 | | 4.67 | 4.67 | 4.67 | | 4.67 | |
| C1 | | 10.68 | | 10.68 | 10.69 | 10.69 | | 10.69 | |
| C2 | 100 | 238.41 | | 238.41 | 239.32 | 239.32 | 239.32 | | |
| C2= | | 108.32 | | 108.32 | 0.00 | 0.00 | 0.00 | | |
| C3 | | 1.11 | | 1.11 | 7.36 | 7.36 | 7.36 | | |
| C3= | | 2.33 | | 2.33 | | | | | |
| C4 | | 0.88 | | 0.88 | 18.71 | 18.71 | 18.71 | | |
| C4= | | 1.77 | | 1.77 | 3.39 | 3.39 | 3.39 | | |
| C5 | | | | | 22.94 | | | | 22.94 |
| C6 | | 0.22 | | 0.22 | 14.35 | | | | 14.35 |
| C7 | | | | | 9.39 | | | | 9.39 |
| C8 | | | | | 7.70 | | | | 7.70 |
| C9 | | | | | 5.22 | | | | 5.22 |
| C10 | | | | | 1.87 | | | | 1.87 |
| C11 | | | | | 0.62 | | | | 0.62 |
| C12 | | | | | 0.78 | | | | 0.78 |
| A6 | | 0.39 | 0.39 | | 0.24 | | | | 0.24 |
| A7 | | | | | 1.86 | | | | 1.86 |
| A8 | | | | | 4.66 | | | | 4.66 |
| A9 | | | | | 6.99 | | | | 6.99 |
| A10 | | | | | 5.35 | | | | 5.35 |
| A11 | | | | | 1.21 | | | | 1.21 |
| Unknown | | | | | 1.05 | | | | 1.05 |
| Total | 100 | 368.78 | 0.39 | 368.39 | 368.39 | 284.14 | 268.78 | 15.36 | 84.25 |

This illustration also depicts how specific operating conditions can be used to control the resulting slate of compounds. The temperature of Reactor 2 was 250° C. which byproducts to be reused in other downstream processes. Table 3c is similar for a C6+ compounds (>98 RON with vapor pressure of 7.8 psi) gasoline with a total yield of 79% from 100% ethane; aromatics were 35% (28/79) of the total yield. The process follows the steps in FIG. 4.

a single static-bed design that operates with greater than 50% less operational downtime.

TABLE 3c

Production of Gasoline from C2 (ethane) feedstock (high-octane, low RVP)

| | | | | | Process Step | | | | |
|---|---|---|---|---|---|---|---|---|---|
| | 1 | 2 | 3 | 4 | 5 LG2F: C2 w/ Recycle Lb/hr | 6 | 7 | 8 | 9 |
| | Feed | R1 Out | Knockout | R2 Feed | R2 Out | Flash Tops | Recycle | Lights Purge | Gasoline |
| H2 | | 6.09 | | 6.09 | 6.09 | 6.09 | | 6.09 | |
| C1 | | 13.94 | | 13.94 | 13.95 | 13.95 | | 13.95 | |
| C2 | 100 | 311.16 | | 311.16 | 312.63 | 312.63 | 312.63 | | |
| C2 = | | 141.38 | | 141.38 | | | | | |
| C3 | | 1.45 | | 1.45 | 9.61 | 9.61 | 9.61 | | |
| C3 = | | 3.04 | | 3.04 | | | | | |
| C4 | | 1.15 | | 1.15 | 24.94 | 24.94 | 24.94 | | |
| C4 = | | 2.31 | | 2.31 | 4.45 | 4.45 | 4.45 | | |
| C5 | | | | | 29.68 | 29.68 | 29.68 | | |
| C6 | | 0.28 | | 0.28 | 18.60 | | | | 18.60 |
| C7 | | | | | 12.17 | | | | 12.17 |
| C8 | | | | | 9.98 | | | | 9.98 |
| C9 | | | | | 6.76 | | | | 6.76 |
| C10 | | | | | 2.42 | | | | 2.42 |
| C11 | | | | | 0.80 | | | | 0.80 |
| C12 | | | | | 1.01 | | | | 1.01 |
| A6 | | 0.51 | 0.51 | | 0.31 | | | | 0.31 |
| A7 | | | | | 2.42 | | | | 2.42 |
| A8 | | | | | 6.04 | | | | 6.04 |
| A9 | | | | | 9.06 | | | | 9.06 |
| A10 | | | | | 6.93 | | | | 6.93 |
| A11 | | | | | 1.57 | | | | 1.57 |
| Unknown | | | | | 1.36 | | | | 1.36 |
| Total | 100 | 481.31 | 0.51 | 480.80 | 480.80 | 401.36 | 381.31 | 20.05 | 79.44 |

Enhanced R2 Reactor—Dual Phase Catalytic Quench

Figure 19:
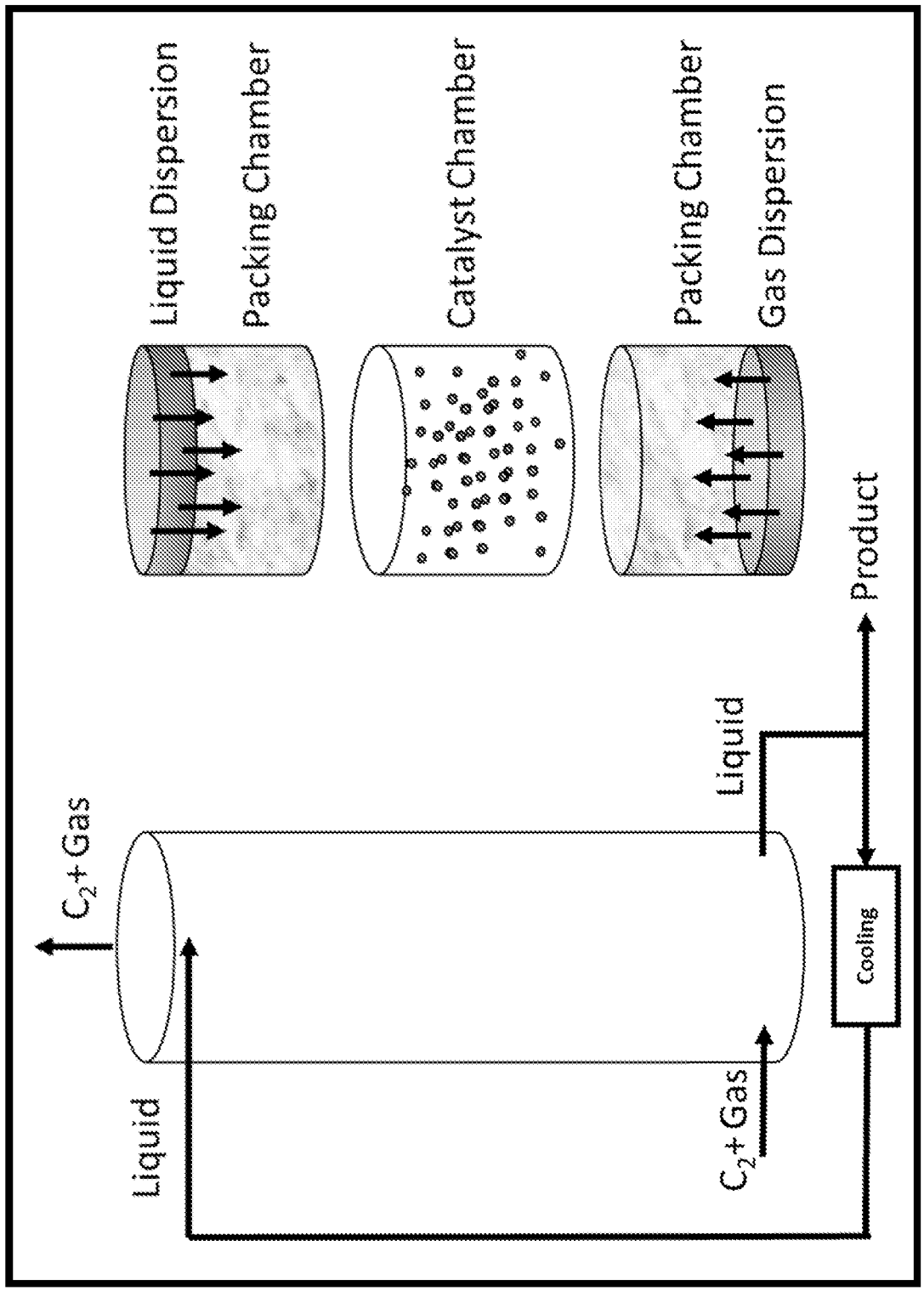
FIG. 19 is a diagram showing components of a novel reactor design featuring a dual phase catalytic quench.

This invention includes a new reactor design shown in FIG. 19, featuring a dual phase catalytic quench (DPCQ) method of processing gas and liquid phase feedstreams in a cross-current technique whereby the liquid phase compounds effectively wash the oligomerization catalyst held in a static-bed configuration and vaporous gases pass in a counterflow direction through the reactor chamber. This technique can be operated at 300-1200 psi but preferable from 400-600 psi with operating temperatures near the dew point of the liquid feed at such pressure, but generally at 250-450° C. Our research has found that the combination of catalytic reaction and molecular absorption methods in a non-adiabatic chamber tends to slow the activity level of the exothermic reaction, thereby allowing greater control over the product selectivity. Our research shows that the key aspects of this DPCQ technique include a) longer catalyst life with virtually no catalytic regeneration required due to the effect of washing the catalyst, b) a decrease in catalytic activity levels thereby improving product selectivity and fuel quality without modifying the chemistry of the catalyst, and c) a lower projected total cost of operation by consolidating the catalytic reactor(s) and absorption functions into This DPCQ technique can be applied to any appropriate R2 related oligomerization-type reactions in the LG2F process used to make targeted hydrocarbon end-product such as gasoline and diesel fuel.

Product Selectivity

The LG2F process uses the feed composition, the Thermal Olefination reaction, and the zeolite catalyst operating conditions (T, P, SV) to establish a predictable result to various fuel performance criteria described on industry fuel specifications. The following outlines how this technique is achieved. Also, see FIGS. 5 and 6.

In one aspect, the process is configured to produce a desirable, broad-range of fuel products. The fuel products are typically in the C5-24+ range of hydrocarbon fuels or fuel blendstocks. The range of fuel products depends in part on the C2-C5 alkane feedstream and is controlled based on operation of the LG2F Process. In one approach, the fuel products are determined in the following manner. First, the available feedstream is analyzed in relation to the desired fuel target. Then a baseline is established taking into account the nature of the feedstream and typical operating conditions for the LG2F Process. For example, it can be established that a given feedstream, e.g., 100% ethane, will produce a predictable array of fuel products with the operation of the Process at certain conditions of temperature, pressure, space velocity and recycle.-

It can further be determined that changes to these conditions will move the product mix in one direction or another. For example, raising the temperature in the zeolite-catalytic reactor R2 will increase cracking of the hydrocarbons and the production of lighter aromatics, resulting in a lower final boiling point of the targeted fuel. A higher pressure, used for example in a secondary R2 reaction will increase the chain-length of middle distillate compounds produced, also impacting the final boiling point of diesel fuel. Higher space velocities result in a higher exotherm temperature which produces lighter compounds (as depicted in FIGS. 5a and 6a). Higher reactor temperatures at a fixed space velocity and pressure reflect a similar tendency to produce lighter compounds (as depicted in FIGS. 5b and 6b). In this manner, it is possible to identify baseline reactor operating conditions and then adjust from there to produce differing product mixes.

Upper Boiling Limit

The temperature of the R2 reactor(s), particularly the second R2 reactor if used in series, is used to prescribe the cut-point of the fuel product, which determines the limit of the final boiling point of the fuel. For example, a fuel specification may call for a final boiling point of 340° C. or 225° C. or 180° C. and the reactor conditions can be set to limit the upper boiling condition to a specific temperature.

TABLE 4

| Upper Boiling Point | Reason | R2 - Zeolite Operating Condition |
|---|---|---|
| To include C12 | FBP 225° C. | Baseline R2 Reactor - 275-325° C. (less cracking) |
| To include C11 | FBP 215° C. | Baseline R2 Reactor - 325-375° C. |
| To include C10 | FBP 200° C. | Baseline R2 Reactor - 400° C. (hot/more cracking) |
| To include C18 | Mid Cetane | Baseline R2 Reactor - (hot/more aromatics) |
| To include C17 | Best Pour Point | Baseline R2 Reactor - (less hot) |
| To include C16 | High Cetane | Baseline R2 Reactor - (cool/less aromatics) |

Lower Boiling Limit

The use of a single stage flash-drum with a preset liquid-vapor temperature limit can establish any lower bound to the liquid fuel without the expense of cryogenics or complex multi-stage fractionation columns. The flash-drum temperature is set at a predetermined point (e.g. for C4 butane (high RVP) for the preferred liquid/vapor cut. The level of precision can be enhanced by using a 2-stage drum.

TABLE 5

| Low Boiling Point | Reason | Flash Cut Point |
|---|---|---|
| To include C4 | High RVP | set flash at 0° C. |
| To include C5 | Mid RVP | set flash at 27° C. |
| To include C6 | Low RVP | set flash at 50° C. |
| To include C7 | Aromatic Cut | Set flash at 105° C. |
| To include C9 | High Cetane | set flash at 125° C. |
| To include C10 | High Cetane | set flash at 150° C. |

Benzene Knock-Out Feature

The Thermal Olefination reaction is known to produce small amounts of benzene, which typically has a control limit in fuels. Accordingly, the LG2F Process utilizes an optional liquid-vapor knockout separation technique set at or below the boiling point of benzene at the appropriate pressure to capture any light aromatics exiting Thermal Olefination. In some embodiments, benzene be separated prior to the R2 reaction. In some embodiments, benzene may alhydrate with olefins in the R2 reaction. In some embodiments, the knockout feature may be undesired as BTX aromatics may be the preferred product for use as a petrochemical feedstock. Since C2-C5 hydrocarbons are generally cracked into C5 and smaller compounds, the primary exception to this is the production of the liquid C6H6 aromatic (albeit valued in select markets) which can then be largely eliminated from the final fuel. This compound can be marketed as BTX or reacted with olefins to make C7+ alky-aromatics to increase octane in gasoline.

Aromatics Content in Gasoline

The temperature of the R2 Reactor is used to pre-determine the level of activation which directly effects aromatic production. Accordingly, the higher octane gasoline formulations favor a C7-C10 aromatic content of up to 50%. This results in the following operating conditions:

TABLE 6

| Activation Level | Reason | Aromatics in Gasoline |
|---|---|---|
| High | High octane (RON > 95) | Up to 55% C7+ aromatics; Baseline + 60-100° C. |
| Medium | Mid octane (RON > 91) | Up to 20% C7+ aromatics; Baseline + 20-60° C. |

TABLE 6-continued

| Activation Level | Reason | Aromatics in Gasoline |
|---|---|---|
| Low | Low octane (RON > 89) | Up to 15% C7+ aromatics; Baseline reactor at 320° C. |

Aromatics Content in Distillate

The temperature of the R2 reactor is used to pre-determine the level of activation which directly affects aromatic production. Accordingly, the higher cetane formulations favor lower aromatic content of less than 25%. The aromatic content of diesel fuel is limited to not exceed 35% and the presence of C16+ aromatics can impede the cetane performance. So the diesel fuel spectrum is generally targeted to C9-C16 range compounds and aromatic content is limited to <35%. This results in the following operating conditions:

TABLE 7

| Activation Level | Reason | Aromatics in Distillate |
|---|---|---|
| High | Low cetane (<40) | Up to 35% C9+ aromatics in distillate; Baseline + 100-175° C. |
| Medium | Mid cetane (>40) | Up to 30% C9+ aromatics in distillate; Baseline + 50-100° C. |
| Low | High cetane (>45) | Up to 25% C9+ aromatics in distillate; Baseline reactor conditions |

Gasoline performance was measured using ethylene with baseline operating at 320° C., atm (0 psig) and 0.75 WHSV.

Space velocity graphs using aliphatics and aromatics were performed at atm (0 psig) at temperature 284° C., 293° C., 318° C. and 343° C. All results demonstrate the core principles for determining the appropriate R2 reactor operating conditions to produce performance fuels. The actual operating parameters will vary depending upon the feedstream. Diesel fuels follow the same basic chemistry and thermodynamic principles as gasoline spectrum reactions.

Control of operating parameters (Temperature, Pressure, Space Velocity) can directly impact the scope and range of molecules produced in a catalytic oligomerization unit. Temperature directly impacts the level of cracking that occurs during oligomerization. An increased temperature causes more cracking to occur which will result in smaller molecules to be produced. Lower temperature will produce longer chained molecules as they crack less while coupling still occurs.

High pressures are preferred for diesel range production as a higher gas concentration will allow for more opportunities for coupling. Locally, more molecules will occupy a given area at high pressure allowing for more reactions to occur in a given time frame. Modifying pressure will have a direct impact on the boiling point of the product as more pressure would create longer molecules. However, more reactions due to high pressure will significantly increase the exotherm so the energy would need to be removed at the rate of generation to minimize cracking.

The same applies for space velocity where an increased space velocity gives a shorter duration of residence time on the catalyst but more reactions per second that will increase temperature as well. Chain propagation can be reduced at high space velocities at the expense of an increased exotherm. Thus, proper heat management can dynamically control product slate, distribution and final boiling point while modifying pressure and space velocity.

Recovery from Entrained C3+ Hydrocarbons from Gas Flows

This invention utilizes a novel technique to maximize liquid volume yield by extracting H2 and all vapor-phase entrained hydrocarbons from a light gas stream comprised of any combination of C1-C5+ hydrocarbons at near ambient temperatures. The preferred embodiment of this liquid separation process uses a quench tower to strip all C3+ vapor-phase hydrocarbons and H2 at temperatures ranging from about 8° C.-40° C. thereby eliminating the need to require cryogenic or subzero processing temperatures that could greatly increase utility costs. This is in direct contrast to traditional absorber technology methods known to those schooled in the art of gas processing which require repeated low-temperature cooling cycles as gases are absorbed from the stream which results in the need for a repetitive, capital intensive process of subzero cooling.

Figure 20:
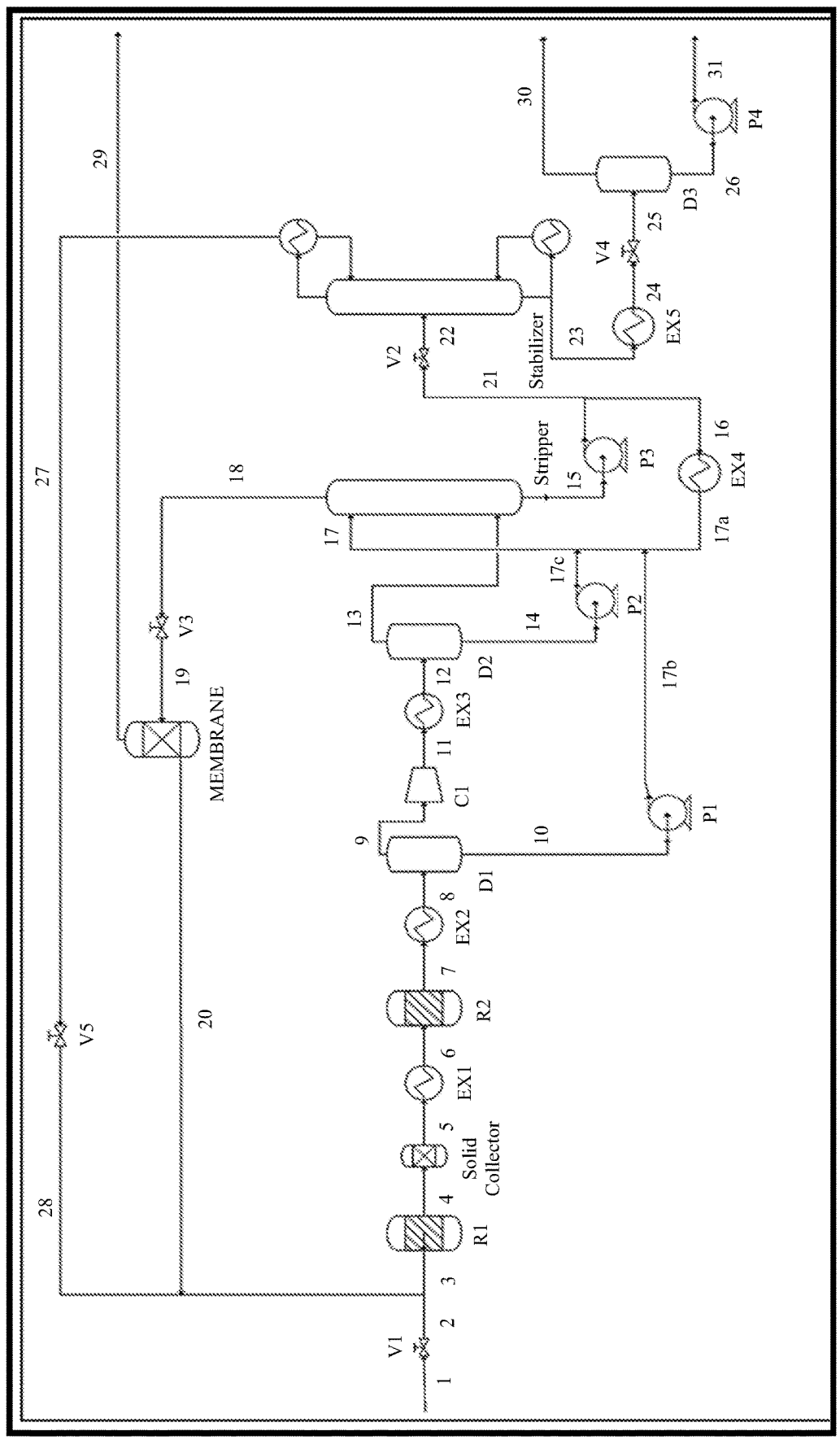
FIG. 20 is a flow diagram showing the LG2F process including liquid recovery, H2 separation, and a recycle subsystem.

This invention operates the quench tower (stripper) shown in FIG. 20 below at pressures up to 1000 psi, but preferably at about 400 psi. However, the downstream stabilizer and recycle loop feeding the Thermal Olefination reactor (R1) are stepped down to lower pressures ranging from 14 to 140 psi. Our research experience for the R1 Thermal Olefination reactor shows that sending a recycle stream at high pressures (e.g. above about 140 psi) to be operated at temperatures above 500° C. will result in lower olefin conversions and trigger serious challenges in the metallurgy of the reactor tubes that could also damage the welds, joints and junctions to the downstream transfer line exchanger. For this reason, the recycle stream feeding R1 necessitates a low-pressure operation. Accordingly, the preferred operating condition of the Thermal Olefination reaction is a low-pressure environment operating at no more than 140 psi. The preferred embodiment of this liquid separation process utilizes a compressor upstream of the quench tower (stripper) to provide effective operating conditions for maximizing the extraction of all light vapor-phase components, while lowering the pressure of the stabilizer (14-140 psi). Accordingly, this low-pressure environment for the stabilizer also prevents unnecessary vaporizing and recycling of valuable liquid product.

This unique design utilizes a quench tower and stabilizer with low cost utilities while eliminating the capital-intensive cost of cryogenics. The higher cost of subzero cooling, cryogenics and compression are not cost-justified for merely extracting the last marginal portion of entrained liquids from the gas stream.

The unique design also depicts the partial separation of methane and hydrogen for alternate uses including powering the LG2F utilities. Also, a balanced portion of these gases is used as a diluent in the R1 reaction to control effective heat duty.

In one aspect of the liquid recovery design, if liquid streams being produced in the quench tower become overly saturated, i.e. C4/C5 lights overflow to heavies, then a flash drum can be used to separate the C4/C5 compounds to re-stabilize the quench process. In this case, the C4/C5 compounds exiting the flash drum can be quenched and commingled with the feed to the stabilizer. Also in this case, the remaining heavies can be split between the stabilizer and the remaining majority (i.e. 50-98% of the split volume) being merged and fed into the quench column.

Commercial Significance

The LG2F Process and System allows for the midstream or refinery production of performance-grade fuels which are tailored to meet ever-changing industry performance criteria in areas where stranded light hydrocarbons are not accessible to traditional fuel and petrochemical supply chains. The US NGL market currently rejects approximately 407,000 BPD of ethane (~10% of the total production NGL's) by selling ethane as natural gas where an ethane market does not exist, despite ethane's higher volumetric BTU value.

Eliminating the "ethane rejection" mode opens up the opportunity for more cost efficient gasoline and diesel fuel production from NGL's and streamlines otherwise stranded, shut-in, or flared methane gas reserves. LG2F also offers a low-cost pathway to upgrade ethane, propane and butane+ compounds to performance-grade fuel values or in some cases petrochemical feedstocks. Producing gasoline and diesel to a fuel performance standard reduces unnecessary logistics costs and allows fuels to enter markets via the existing finished product fuel supply chains.

The LG2F Thermal Olefination reaction (R1) along with the catalytic reaction (R2) and recycle loop can be used independently and can be interchangeably tailored based upon feedstock composition and desired end products to produce gasoline blendstocks and/or diesel fuel blendstocks. The process is flexible to allow the reactor operating conditions to be established to produce the desired blend components and compositional features to meet fuel performance requirements (e.g. aromatics for gasoline octane value, cetane for diesel performance). The byproducts of the reaction may include methane and hydrogen.

The tailoring effects of the gasoline and diesel fuel reactions include a variety of factors including the final boiling point cut-off of the product, the lower cut-off of the product—both of which are based on the operating conditions for any given feedstream. Other factors include the % m/m of C6 aromatics, the % of C5 used in the gasoline (RVP index), the cetane number, the % aromatics, the % C18+ compounds, etc.

A major feature of the LG2F Process is the targeting of performance grade fuel products. Rather than indiscriminately producing a stream of random hydrocarbons, this invention serves to tailor the process and operating conditions for specific purposes. For example, when targeting gasoline, C4 and C5 compounds typically have higher vapor pressure and lower octane values than preferred C6-C12 compounds, so too much concentration of C4/C5 compounds in the targeted fuel will result in a low-grade off-spec fuel. Similarly, high-performance gasoline with more than 50% aromatics, while high in octane, can be undesirable for environmental emissions. Yet other users of the process may prefer to produce a very high concentration of aromatics in a constrained market—only to be used as blendstocks with other surplus components (e.g. before blending into a final fuel at a refinery). In yet another example, the presence of excess benzene can also be on operating limitation to some fuel specifications. Diesel fuel requires a high proportion of C9-C16 compounds with relatively high cetane values; diesel also requires hydrocarbons that do not form wax (solids) at lower temperatures. Accordingly, this invention offers a wide variety of process techniques and optionality for the user to configure the catalytic operating conditions to meet the intended performance-grade product outcomes.

An optional feature of LG2F is to produce C4 and C5 alkanes which may be useful for increasing the volatility and raising the vapor pressure in gasoline, although often at the expense of octane levels. Thus, some or all the C4-5 alkanes may be targeted for production into the gasoline blendstock. Alternatively, C4 or C4-C5 production may be avoided, in which case the process directs $\leq C_4$ or $\leq C_5$ byproducts to be recycled for further upgrading.

It will be appreciated that the LG2F Process can include split multi-iterative variations of both R1 and R2 that may require more than a single recycle loop for optimal operation. As an example, R2 may be separated into two or more reaction sequences with some form of separation between and after the operations. The separation off-gas may be merged or recycled independently and at different locations from one another.

LG2F Products

The process configuration utilizes a recycle loop to produce a specified range, for example $C_5$ to $C_{12}$ gasoline compounds or $C_9$ to $C_{20}$ diesel fuel compounds for use as blendstocks in high grade transportation fuels. Using the LG2F process, the liquid yields using recycling can range from 65% to 95+% of the initial feedstream depending upon the severity of operating conditions. This process offers flexibility in making paraffinic molecules of higher yield, or olefinic molecules and aromatic hydrocarbons of somewhat lower yields for gasoline range products, or alternatively, it can be switched to create a blend of middle distillates (primarily paraffins, olefins and aromatics) primarily for diesel range products. As an alternative, excess methane can be used as process fuel or recycled into fuels.

Gasoline Blendstocks

In one aspect the LG2F Process is tailored to the production of gasoline blendstocks, as exemplified in the foregoing discussion. As used herein, the term "gasoline blendstock" refers to a formulation comprising n-paraffins, iso-paraffins, cyclo-paraffins, olefins and aromatics having 4 to 12 carbons. The gasoline blendstocks from this invention preferably have 5-12 carbons, and more preferably comprise 6-11 or 7-10 carbons. The gasoline blendstocks also typically have branched-chain paraffins and aromatic hydrocarbons having 6 to 11 carbons, preferably 7 to 10 carbons. In preferred embodiments, the LG2F Process yields a product containing at least about 65% C5-10 branched-chain paraffins and at least 25% C7-9 aromatic hydrocarbon compounds. The following examples further demonstrate the ability to tailor the LG2F Process depending on the C2-5 feedstream and the desired end product(s).

TABLE 8

Typical Gasoline Composition

| | Typical Gasoline Constituents | | | | | | | |
|---|---|---|---|---|---|---|---|---|
| | C4 | C5 | C6 | C7 | C8 | C9 | C10 | C11 | C12 |
| n-paraffins | X | X | X | X | ◯ | ◯ | ◯ | ◯ | ◯ |
| iso-paraffins | X | X | X | X | X | X | X | ◯ | ◯ |
| cyclo-paraffins | | X | X | X | X | X | X | ◯ | ◯ |
| olefins | | X | X | X | X | X | X | ◯ | ◯ |
| aromatics | | | X | X | X | X | X | ◯ | ◯ |

While the gasoline blendstocks described as the products of LG2F in this invention may be comprised of varying chemical compounds, the compounds output from this invention is not randomly indiscriminate. This is accomplished as described herein by, inter alia, selection of C2-5 Alkane Feedstreams, operating parameters and recycle between the R1 and R2 reactors. The production of high-performance gasoline requires the adherence to a minimum set of performance conditions for gasoline grade products. The LG2F Process produces, for example, fuel compositions and blendstocks including the following:

In one embodiment, the gasoline compound is ≥95 research octane number (RON) with no ethanol, with a ≥9 psi vapor pressure (RVP) but ≤13.5 psi, aromatic content ≤50% m/m and with benzene content below 1.30% (v/v), and a final boiling point <225° C.

In one embodiment, the gasoline compound is >95 RON with no ethanol, with a vapor pressure ≥9 psi but ≤13.5 psi, aromatic content <55% m/m and with benzene content below 1.30% (v/v), and a final boiling point <225° C.

In one embodiment, the gasoline compound is ≥91 [using R+M/2] with no ethanol, with a vapor pressure ≥9 psi but ≤13.5 psi, aromatic content ≥35% m/m and with benzene content below 1.30% (v/v), and a final boiling point <225° C.

In one embodiment, the gasoline compound is ≥89 [using R+M/2] with no ethanol, with a vapor pressure ≥9 psi but ≤13.5 psi, aromatic content ≤35% m/m and with benzene content below 1.30% (v/v), and a final boiling point <225° C.

In one embodiment, the gasoline compound is ≥87 [using R+M/2] with no ethanol, with a vapor pressure ≥9 psi but ≤13.5 psi, aromatic content ≤30% m/m and with benzene content below 1.30% (v/v), and a final boiling point <225° C.

In one embodiment, the gasoline compound is ≥84 [using R+M/2] with no ethanol, with a vapor pressure ≥9 psi but ≤15.0 psi, aromatic content ≤25% m/m and with benzene content below 1.30% (v/v), sulfur content below 0.008% (m/m), and a final boiling point <225° C.

C2-5 Hydrocarbons to C6-8 Aromatics

In an embodiment, the LG2F Process is tailored by isolating the catalytic R2 reaction to convert $C_2$-$C_5$ light olefin feedstocks into aromatic hydrocarbons comprising a narrow range of $C_6$ to $C_8$ aromatics for use as a high-octane fuel blendstock or petrochemical use. This is done by use of operating conditions to obtain an aromatic yield up to the upper boiling limit of o-xylene, for example 145° C., and recycling all byproducts in the flash drum with boiling points below benzene at 80° C. The yield of $C_6$ to $C_8$ aromatics is valuable to the petrochemical market as a base aromatic feedstream to aromatics fractionation or as an alternative, if the BTX product stream is first processed by a hydrodealkylation step to decouple and remove ethyl-propyl and butyl-aromatic constituents leaving only methyl-aromatic products.

C2-5 Hydrocarbons to C7-8 Aromatics

In another embodiment, this invention can be tailored by isolating the catalytic R2 reaction to convert $C_2$-$C_5$ light olefin feedstocks into aromatic hydrocarbons in a narrow range of $C_7$ to $C_8$ aromatics. Again, this is done by targeting the aromatic yield up to the upper boiling limit of o-xylene, for example 145° C., and recycling all byproducts in the flash drum with boiling points below toluene at 110° C. The yield of $C_7$ and $C_8$ aromatics have a very high-octane value and a very high energy density in the absence of benzene and are useful gasoline blendstocks to meet premium high-octane grades.

C2-5 Hydrocarbons to C8 Aromatics

In another embodiment, the LG2F Process is tailored by isolating the catalytic R2 reaction to convert $C_2$-$C_5$ light olefin feedstocks into aromatic hydrocarbons in a narrow range of solely $C_8$ aromatics by targeting operating conditions for the aromatic yield up to the upper boiling limit of o-xylene, for example 145° C., and recycling all byproducts in the flash drum with boiling points below p-xylene at 138° C. The yield of $C_8$ aromatics will have a very high-octane value and a very high energy density which can be a useful gasoline blendstock to meet premium high-octane grades. In addition, these $C_8$ compounds may be further valuable to the petrochemical market, particularly if they are produced by a hydrodealkylation step to decouple and remove any close-boiling ethyl-aromatic constituents and produce methyl-aromatic products.

C2-5 Hydrocarbons to C7-9 Aromatics

In one embodiment, this invention is tailored by isolating the catalytic R2 reaction to convert $C_2$-$C_5$ light olefin feedstocks into aromatic hydrocarbons in the $C_7$ to $C_9$ range by specifying operating conditions for the aromatic yield up to the upper boiling limit of trimethylbenzenes, for example 175° C., and recycling all byproducts in the flash drum with boiling points below toluene at 110° C. The yield of $C_7$ to $C_9$ aromatics will have a very high-octane value and a very high energy density, without the presence of benzene, and can be a useful gasoline blendstock to meet premium high-octane grades.

C2-5 Hydrocarbons to High-Octane Aliphatic Compounds

One specialized technique to produce high-octane gasoline blendstocks is the use of LG2F in a tailored fashion to limit the production of aromatics and instead produce high-octane aliphatic compounds by the targeted conversion and/or dimerization of C2-C4 alkanes and olefins without coupling or cyclizing of the reaction to produce fuels without the expense of complex fractionation. This is achieved without traditional high-toxicity HF and H2S type alkylation methods by setting the synthesis protocol and operating conditions of the catalytic R2 chemical reaction(s) to produce the desired product stream. All light hydrocarbon gases below a lower targeted boiling point limit are recycled to maximize the yield potential of this technology. This technique allows production of a simple narrow band of desirable of C6, C7, or C8+ hydrocarbons (in one preferred case C7 trimethylpentenes) from C2+ light gases that may be particularly valuable to the high-octane gasoline blending process while avoiding the production or use of benzene and C7-C9 aromatics traditionally used by refiners to increase the octane value of the fuel.

This version of the LG2F process is particularly tailored to selectively convert or dimerize C2-C4 feedstreams with catalysts at low activity levels to make higher carbon products while minimizing cycling and coupling of the molecules during the R2 catalytic reactions to make aliphatic hydrocarbons. This technique will serve to maximize the yield of targeted high-octane gasoline blendstocks comprised of C6, C7 or C8+ aliphatic hydrocarbons or in some configurations longer-chain diesel fuel blendstocks comprised of C9-C16+ aliphatic hydrocarbons.

The choice of feedstream may include those comprising a) light C2-C4 alkanes (e.g. from wet gas processing or industrial sources), or b) light C2-C4 alkenes (e.g. from refinery FCC units, specifically as byproducts of a ZSM-5 catalytic reaction).

In one aspect using wet-gas supply sources, feedstreams comprised of C2+ alkane-rich hydrocarbons flow into the R1 Thermal Olefination reaction producing C2+ alkenes which are subsequently passed to a R2 catalytic reaction to be dimerized by one or more sequential R2 reactions using various specialized zeolite catalysts including those in proton form. A wide range of available zeolite catalyst processes are known to those schooled in the art. In addition, non-zeolite catalysts (e.g. Cobalt/triethyl-aluminum, Ni-MFU-41, etc.), may also be utilized for selective dimerization reactions targeting C4+ alkenes. The R2 effluent may then pass into an optional skeletal isomerization technique using ZSM-35 to created high-valued iso-alkanes for specialized uses. Unreacted C1+ alkanes comprised in the R1 effluent can be carried throughout each of the catalytic reactions and the light-ends extracted by the liquid recovery module can be recycled back to R1 to be merged with fresh feedstreams to optimize the overall process and maximize yields. Unreacted light alkenes can be recycled while the C6+ liquid streams can optionally then be hydrogenated for use as high-octane gasoline blendstocks and/or C9+ liquid streams for diesel fuel. A truncated version of this aliphatic production process can occur when concentrated sources of either ethene or butene are available to be fed directly into the R2 catalytic reaction(s) (i.e. bypassing the need for Thermal Olefination) again using the R2 dimerization process with the specialized catalysts including those in proton form, with or without skeletal isomerization, followed by the liquid recovery process and light gas recycle loop back to R2 catalytic reaction process, after which the C6+ aliphatic liquids are recovered, with or without a hydrogenation step as may be required for fuel quality.

In one aspect using refinery processes, light gas feedstreams comprised of C2+ alkene-rich hydrocarbons are captured as a byproduct of adding ZSM-5 catalyst to any refinery Fluid Cat Cracking (FCC) process to effectively crack C7+n-paraffin compounds typically produced in such processes. This inventors prior art has shown that these C7+n-paraffins have very low octane values. Refiners often avoid such n-paraffin cracking in the FCC unit (and the use of ZSM-5 zeolites) as it reduces the FCC liquid yield via the production of large amounts of unwanted light C3-C4 alkenes. However, this LG2F invention selectively captures these C2-C4 light alkene gases (preferably propene and butene) and converts them into high-value C6, C7 and C8+ liquid aliphatic hydrocarbons—notably without the formation of aromatics—for use in gasoline. The alkene-rich feedstreams comprised of C3 and C4 alkenes pass directly into an R2 catalytic reaction process at appropriate temperature (up to 550° C.) and pressure (up to 750 psi) using weak-acidic catalysts generating lower activity levels by using post-transition metals and/or metalloids, preferably Ga(III), Zn(II), In(III), B(III), Ge(IV) or Bi(V). Reactor design is any variety of plug-flow, semi-regen or continuous regeneration capability using fixed or fluidized bed design based upon the best practices of those skilled in the art. The resulting R2 liquid effluent is condensed via the quench and stabilization process resulting in a C6+ liquid admixture comprising high-octane di-methyl or tri-methyl alkenes (i.e. typically -butene and/or -pentenes); see chart. This fuel blendstock may be used directly as a fuel blendstock or it may be further hydrogenated or mixed with antioxidants depending upon the degree of tailoring needed in the finished blendstock. The resulting upgrade from C7+n-paraffins to C3-C4 alkenes to C6+ high octane fuel by this invention is coupled with the benefit that the n-paraffin octane "penalty" of the FCC liquid stream is erased via ZSM-5 cracking, making the resulting FCC liquid effluent (containing aromatics) a higher octane refined product admixture as well, thereby providing a double benefit.

| Admix C6+ Compounds | # Carbons | ASTM Motor Octane Number |
| --- | --- | --- |
| 2,3-Dimethyl-1-butene | 6 | 128 |
| 2,4-Dimethyl-2-pentene | 7 | 123 |
| 2,3,3-Trimethyl-1-butene | 7 | 130 |
| 2,4,4-Trimethyl-1-pentene | 8 | 156 |

Example Alkene Compounds in the C6+ Aliphatic Admixture

In one embodiment of the LG2F process tailored to produce high-octane non-aromatic fuels, a hydrocarbon feedstream comprised of >80% isobutane is processed by the R1 Thermal Olefination reaction operating at about 400-700° C. to form an effluent comprised of high concentrations of isobutene along with unreacted iso-alkanes which is then enters the R2 catalytic reaction and the iso-alkenes are dimerized using specialized zeolite catalysts including in a proton form configured with or without particular metals (e.g. B, Ga, Zn, Ni, Co, Ca, etc.) to directly convert the isobutene to an aliphatic liquid comprised of C8 trimethylpentenes. The preferred embodiment of the R2 reaction utilizes a dealuminated zeolite H-beta catalyst with Si/Al ratio of 30, operating below 150 psi at 30-100° C., to selectively dimerize isobutene. The R2 catalytic reaction converts at least 50% of the isobutene to C8 alkenes per pass. Any non-olefin hydrocarbon byproducts comprised in the R1 effluent are unreacted in the R2 catalytic process. This R2 reaction is tailored to limit the dimerization of n-olefins if they exist that might otherwise reduce octane values in the targeted C8 stream of trimethylpentanes. The R2 effluent is then processed by one or more liquid recovery processes (e.g. quench and stabilization) to recycle the light ends of the R2 effluent comprised of unreacted alkanes and olefins. The R2 effluent >C4 is then hydrogenated in preparation to produce effective fuel grade blendstocks and is then separated to isolate the C8 branched alkanes from the >C8 branched alkanes. As an alternative, the <C4 light gas recycle stream may be hydrogenated prior to recycling to increase the presence of alkanes in the merge stream prior to reentering the R1 Thermal Olefination process, but this is an economic decision. The hydrogenated liquid effluent from R2 is then passed via simple separation, either via knock-out or optionally under higher pressure to condense the liquids, to isolate the C8 stream comprised of high octane trimethylpentanes from >C8 stream comprised of C12 and higher alkanes desirable for diesel fuel. The hydrogenation step may utilize hydrogen from the membrane separation process or from any available hydrogen source.

Figure 21:
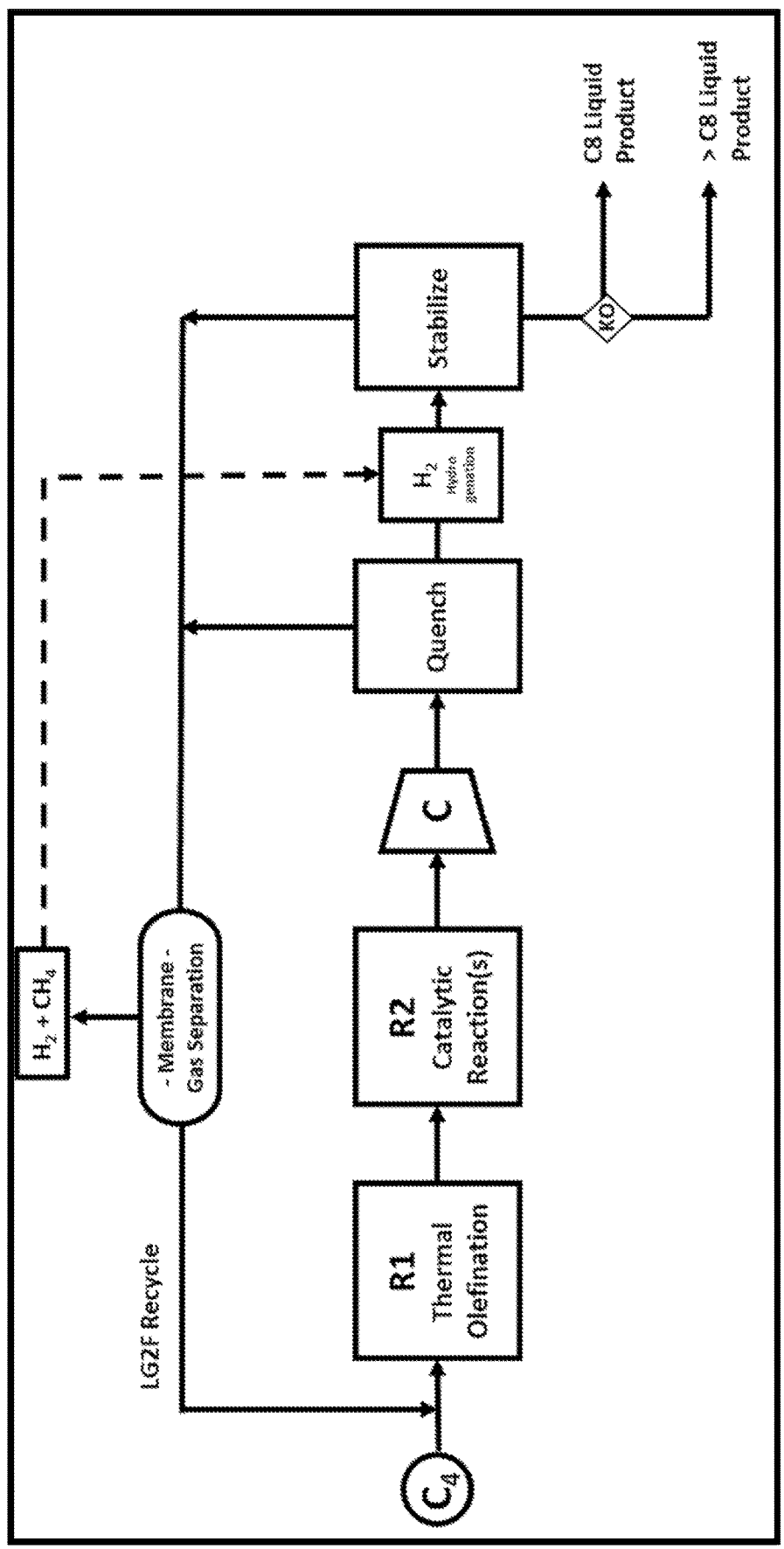
FIG. 21 is a flow diagram showing an embodiment tailored to produce non-aromatic fuel compounds.

In another embodiment tailored to produce non-aromatic fuel compounds, shown in FIG. 21, a feedstream comprising >80% of the combination of n-butane and isobutane in a ratio of 0-1:1.0, the alkanes are fed single pass in the absence of a recycled stream into the R1 Thermal Olefination process whereby n-butenes and isobutenes are produced with >80% alkane conversion and passed to the specialized R2 dimerization process using specialized zeolite catalysts including in a proton form to convert the isobutenes to isooctenes and higher while leaving the n-butenes virtually unreacted. In this case, unconverted C4-alkanes and n-butenes are high-vapor pressure byproducts of this reaction useful for selective gasoline blending.

In another embodiment, a feedstream comprising >80% (wt) of the combination of n-butane and isobutane in any ratio ranging from 0-1:1.0 respectively is fed into the R1 Thermal Olefination process operating at about 400-700° C. whereby an effluent stream comprised of proportional amounts of n-butene and isobutene results in >80% "fresh" alkane conversion. This R1 effluent is then passed to the specialized R2 alkene dimerization process using specialized zeolite catalysts including in a proton form configured with or without particular metals (e.g. B, Ga, Zn, Ni, Co, Ca, etc.) to directly convert the isobutene to an aliphatic liquid comprised of C8 trimethylpentenes, while n-butenes are unreacted. The preferred embodiment of the R2 reaction utilizes a dealuminated zeolite H-beta catalyst with Si/Al ratio of 30, operating below 150 psi at 30-100° C., to selectively dimerize isobutene. The R2 catalytic reaction converts at least 50% of the isobutene to C8 alkenes per pass. Unreacted light gases exiting the R2 catalytic reaction are isolated during the liquid recovery (quench) process and those comprising n-butenes and isobutene are then passed without fractionation directly to a specialized single or multi-loop n-butene isomerization reaction to increase the proportion of isobutene in this admixture by up to 20-50%. This skeletal isomerization process preferably utilizes a dealuminated ZSM-35 zeolite catalyst operating at about 400° C. with WHSV 5h-1 or other preferred methods known to those skilled in the art of n-butene isomerization. Iso-alkanes and iso-alkenes in this specialized isomerization process are unreacted. The resulting isomerized effluent, now comprised of a higher concentration of isobutene, is then recycled and merged to re-enter either the R1 Thermal Olefination reaction (if the merged stream is alkane-rich) or the R2 catalytic reaction (if the merged stream is alkene-rich) to maximize C8+ liquid product yield. The C5+ liquid recovered from the R2 effluent is then hydrogenated and passed via simple separation, either via knock-out or optionally under higher pressure to stabilize and condense the liquids, to isolate the C8 stream comprised of high octane trimethylpentanes from >C8 stream comprised of C12 and higher alkanes desirable for diesel fuel. The hydrogenation step may utilize hydrogen from the membrane separation process if utilized for system equilibrium or from any available hydrogen source.

In another embodiment, a refinery FCC unit is tailored to use zeolite catalysts to generate a surplus of isobutene gas. This stream of light gas comprising >80% (wt) isobutene is then isolated from the remaining FCC effluent and passed directly to the R2 catalytic process (not depicted). In this example, the R1 Thermal Olefination process is unnecessary and the LG2F recycle loop following the R2 reaction can merge and reenter the R2 catalytic reaction. In one case, methane and hydrogen may accompany the isobutene stream from the source to provide an equilibrium for fuel, as diluent and for hydrogenation proposes. In a different case, "on-purpose" methane or hydrogen can be supplied to balance the LG2F process needs and thereby avoid the need for the membrane separation process.

In a similar embodiment, any available feedstream comprised of >80% isobutene gas can utilize the LG2F process using the methods outlined above.

In another embodiment, a alkane-rich hydrocarbon feedstream comprised of >80% ethane is converted via the R1 Thermal Olefination reaction to an C2+ effluent stream comprised of ethene and unreacted compounds which then enters the specialized R2 catalytic reaction to be dimerized, isomerized and selectively re-dimerized in a combination of reaction steps to produce a high portion of C8+ olefins. The specialized catalytic process includes a combination of selective dimerization and isomerization techniques in a three-part sequence to convert C2 alkenes to C4 alkenes to a high proportion of C4 iso-alkenes which are finally re-dimerized to yield C8+ iso-alkenes. These iso-alkenes are then hydrogenated, condensed, and separated via a simple knock-out technique to yield a high proportion of C8 trimethylpentanes useful for high-octane gasoline (without aromatics) and a remaining liquid portion comprised of C12 to C16 alkanes very useful as premium diesel fuel blendstocks. The specialized dimerization process can be adjusted to raise or lower the proportion of C8's vs the C12-16 range of products yielded from this catalytic protocol.

One such example of the optionality is the targeting of isobutane, a high-octane compound typically used to add vapor pressure (RVP) to gasoline blending, but also used as a feedstock to any traditional paraffin alkylation process. The catalytic R2 chemical reaction favors the production of branched-chain paraffins, which reduces the likelihood of producing n-paraffins which boil on either side of isobutane. Accordingly, as a result of the tailored LG2F R2 reaction, isobutane ($C_4H_{10}$) can be isolated using a high-pressure separation vessel. The target is a narrow boiling range of between −40° C. and −2° C. at atmospheric conditions, which can be pressurized to partially liquefy the stream and extract $C_4$ iso-paraffins. All the lights below −40° C. (notably ethane and propane) are recycled to maximize the yield of branched paraffins within the temperature band.

In a similar example, the LG2F R1 Thermal Olefination reactor in this invention can be targeted to produce any combination of $C_3$-$C_5$ olefins (propene, butene and/or amylene) from any C3-C5 light gas alkanes which can then be directly applied into any traditional paraffin alkylation unit with the additional feed of isobutane (from any source) for production of high-octane, branched-chain paraffinic hydrocarbons, particularly 2,2,4-trimethylpentane (Isooctane).

In a combined example, the LG2F R1 Thermal Olefination reaction can be processed using any C3-C5 alkane gases to produce C3-C5 olefins. The ≤C3 stream can be extracted and processed by R2 (with the option to add additional light olefin streams) to target the production of isobutane or isobutene as described above. Any C6+ byproducts from the R1 reaction can be captured by liquid-vapor knockout for surplus gasoline or reuse. This tailored configuration results in the critical feedstreams necessary for input to paraffin alkylation.

Diesel Blendstocks

Diesel fuel has several key performance characteristics which depend upon the chemical composition of the fuel. Diesel fuels are generally comprised of n-paraffins, iso-paraffins, cycloparaffins and aromatics in such a way as to meet key performance requirements of the fuel. For example, in a diesel engine, cetane number is the measure of the speed of the compression ignition upon injection of the fuel, as well as the quality of the fuel burn in the combustion chamber. Accordingly, a high-performance diesel fuel is preferred to have an aggregate cetane index value (using ASTM D613) of at least 40 and as high as 60.

Figure 7:
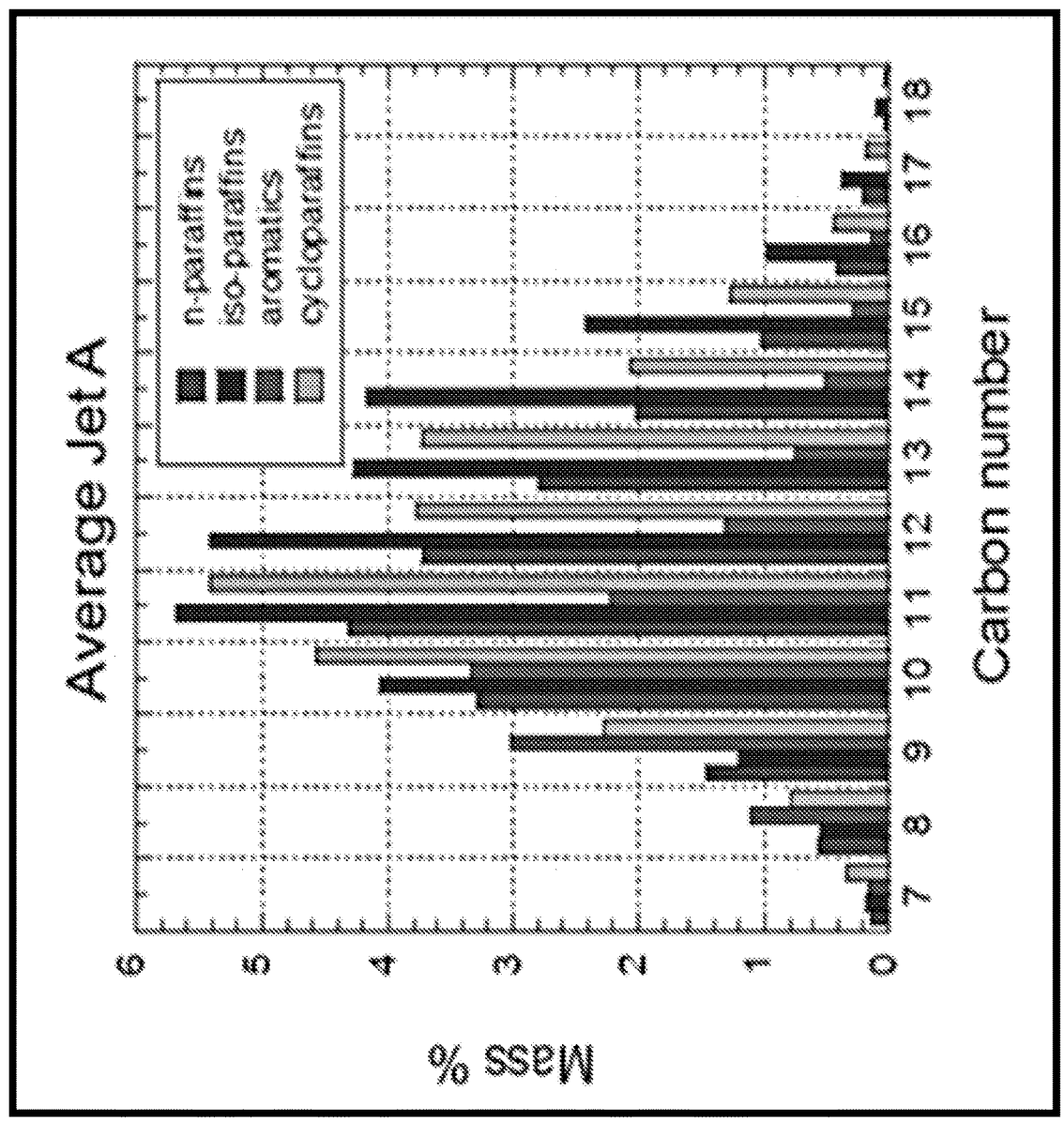
FIG. 7 is a graph showing mass percentages of hydrocarbons for Average Jet A fuel.
Figure 8:
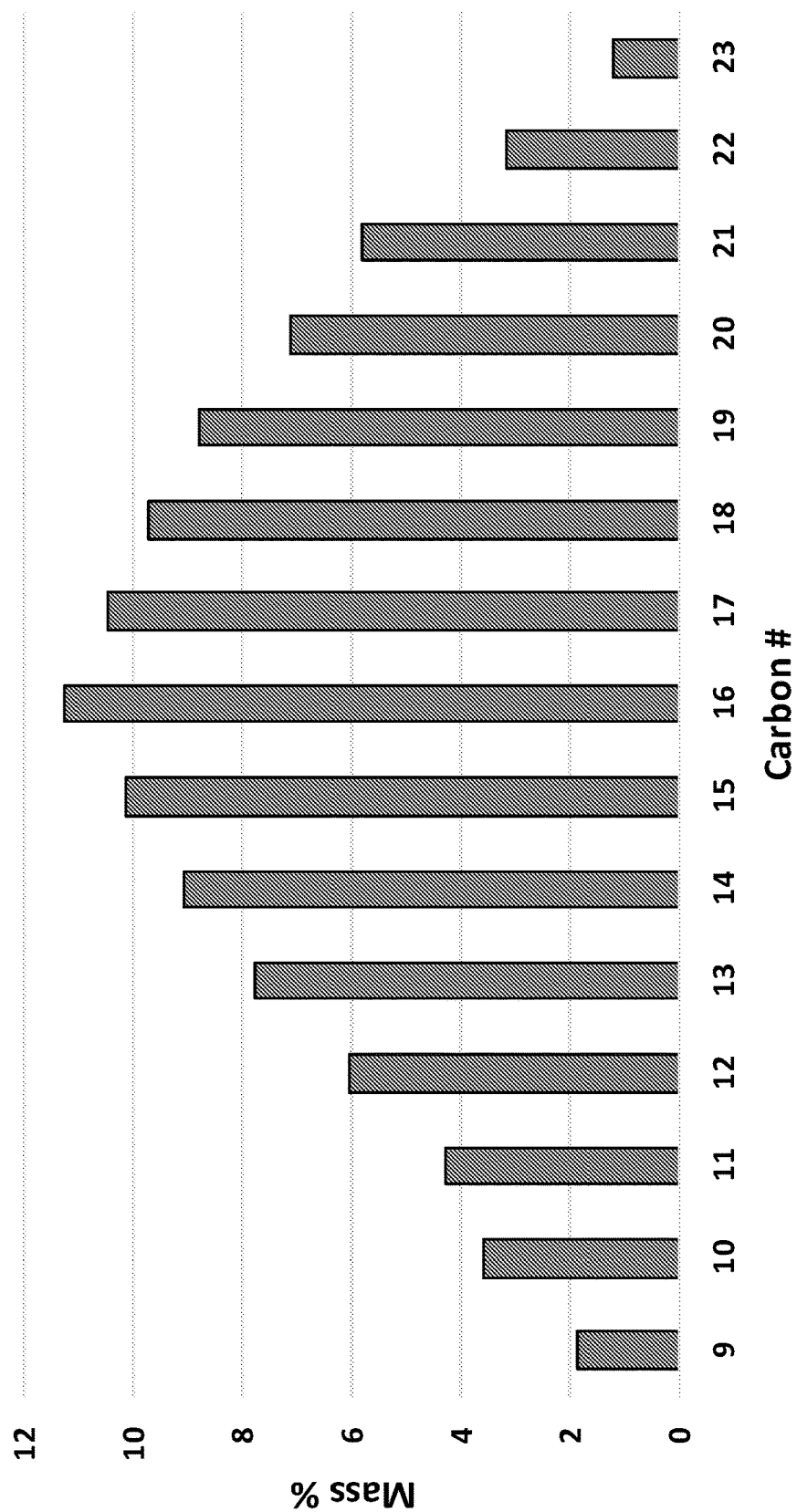
FIG. 8 is a graph of mass percentages in a typical carbon distribution for diesel fuel.

In addition, very low sulfur levels are also highly desirable in diesel fuel to eliminate corrosive wear-and-tear and prevent engine emission control system issues. Jet fuel and diesel fuel, both derived from middle distillates, share many common features. See FIG. 7 and FIG. 8. However, ASTM International fuel specifications call for different performance-based fuel test results impacting cetane, lubricity, viscosity, low temperature flowability, sulfur content, heating value, and more. The performance requirements are what dictate the composition and operating requirements to produce the desired fuel.

Generally, $C_{9+}$ n-paraffins, iso-paraffins and cycloparaffins have higher cetane values than aromatics and are key constituents in the diesel blendstock to achieving high cetane measures (e.g. 40-60) for good fuel performance. Cetane Values for various n-paraffins are shown below in Table 8.

TABLE 8

C9+ n-Paraffin Compounds Have Highest Cetane Values

| C9 to C20 n-Paraffins | Formula | Boiling Pt (° C.) | Melting Pt (° C.) | Cetane # |
|---|---|---|---|---|
| N-NONANE | C9H20 | 150 | −48 | 72 |
| N-DECANE | C10H22 | 174 | −30 | 76 |
| N-UNDECANE | C11H24 | 196 | −26 | 81 |
| N-DODECANE | C12H26 | 216 | −10 | 87 |
| N-TRIDECANE | C13H28 | 235 | −5 | 90 |
| N-TETRADECANE | C14H30 | 254 | 6 | 95 |
| N-PENTADECANE | C15H32 | 271 | 10 | 96 |
| N-HEXADECANE | C16H34 | 287 | 18 | 100 |
| N-HEPTADECANE | C17H36 | 302 | 22 | 105 |
| N-OCTADECANE | C18H38 | 316 | 28 | 106 |
| N-NONADECANE | C19H40 | 336 | 32 | 110 |
| N-EICOSANE | C20H42 | 344 | 36 | 110 |

However, while C14+n-paraffins have high Cetane Values, their melting point is above low ambient temperatures leading to wax crystals forming in the fuel, which can foul or block fuel lines in cold weather, for example. See Table 10. Specialized pour point, cloud point and cold filter plugging tests often call for a reduction of heavier n-paraffinic compounds in middle distillates (often via dewaxing) to improve the cold flowability and operability of a diesel fuel. In addition, n-paraffins have lower volumetric heating value (btu/gal) in comparison to aromatics.

TABLE 10

C14+ n-Paraffin Compounds Melting Points

| $C_9$ to $C_{20}$ n-Paraffins | Formula | Boiling Pt (° C.) | Melting Pt (° C.) | Cetane # |
|---|---|---|---|---|
| N-NONANE | C9H20 | 150 | −48 | 72 |
| N-DECANE | C10H22 | 174 | −30 | 76 |
| N-UNDECANE | C11H24 | 196 | −26 | 81 |
| N-DODECANE | C12H26 | 216 | −10 | 87 |
| N-TRIDECANE | C13H28 | 235 | −5 | 90 |
| N-TETRADECANE | C14H30 | 254 | 6 | 95 |
| N-PENTADECANE | C15H32 | 271 | 10 | 96 |
| N-HEXADECANE | C16H34 | 287 | 18 | 100 |
| N-HEPTADECANE | C17H36 | 302 | 22 | 105 |
| N-OCTADECANE | C18H38 | 316 | 28 | 106 |
| N-NONADECANE | C19H40 | 336 | 32 | 110 |
| N-EICOSANE | C20H42 | 344 | 36 | 110 |

Unlike gasoline for spark-ignited piston engines, which depend upon $C_7$-$C_9$ high-octane aromatics to retard early ignition, $C_{10}$ to $C_{20}$ aromatics provide diesel engines thermal stability, heating value (btu/gallon) and desirable elastomer swell characteristics. Unfortunately, these aromatics generally have low cetane values which can impede effective diesel engine performance. The right balance of aromatic vs. aliphatic compounds will impact the performance characteristics of the diesel blendstock. See Table 11.

TABLE 11

C10+ Aromatic Compounds Cetane Values

| C10 to C20 Aromatics | Formula | Boiling Pt (° C.) | Melting Pt (° C.) | Cetane # |
|---|---|---|---|---|
| N-BUTYLBENZENE | C10H8 | 183 | −88 | 6 |
| 1-METHYLNAPHTHALENE | C11H10 | 245 | −30 | 0 |
| N-PENTYLBENZENE | C11H16 | 205 | −75 | 8 |
| N-HEXYLBENZENE | C12H18 | 226 | −61 | 19 |
| N-HEPTYLBENZENE | C13H20 | 246 | −48 | 35 |
| 1-N-BUTYLNAPHTHALENE | C14H16 | 289 | −20 | 6 |
| N-OCTYLBENZENE | C14H22 | 264 | −36 | 32 |
| N-NONYLBENZENE | C15H24 | 282 | −24 | 50 |
| N-DECYLBENZENE | C16H26 | 298 | −14 | |
| N-UNDECYLBENZENE | C17H28 | 313 | −5 | |
| 2-N-OCTYLNAPHTHALENE | C18H24 | 352 | −2 | 18 |
| N-DODECYLBENZENE | C18H30 | 328 | 3 | 68 |
| N-TRIDECYLBENZENE | C19H32 | 341 | 10 | |
| N-TETRADECYLBENZENE | C20H34 | 354 | 16 | 72 |

It is therefore desirable to be able to produce diesel blendstocks that primarily contain high Cetane Value components (e.g. $C_9$-$C_{16+}$ n-paraffins) with lesser targeted amounts of aromatics (e.g. $C_9$-$C_{16}$) whose lower melting points help increase cold flowability of the fuel.

Olefins are also a product of the R1 and R2 reactions and play a key role in diesel fuel blendstocks. The Cetane Values of $C_9$ to $C_{20}$ olefins are moderately high (above 50) and the $C_9$-$C_{15}$ melting points tend to be cooler than ambient temperatures helping to improve cold flowability, making them ideal compounds for diesel fuel. See Table 12.

TABLE 12

| Olefin Compounds | Formula | Boiling Pt ° C. | Melting Pt ° C. | Cetane # |
|---|---|---|---|---|
| 1-NONENE | C9H18 | 146.87 | −81 | 51 |
| 1-DECENE | C10H20 | 170.57 | −66 | 56 |
| 1-UNDECENE | C11H22 | 192.67 | −49 | 65 |
| 1-DODECENE | C12H24 | 213.36 | −35 | 71 |
| 1-TRIDECENE | C13H26 | 232.78 | −13 | |
| 1-TETRADECENE | C14H28 | 251.10 | −12 | 80 |
| 1-PENTADECENE | C15H30 | 268.39 | −3 | |
| 1-HEXADECENE | C16H32 | 284.87 | 4 | 86 |
| 1-HEPTADECENE | C17H34 | 300.33 | 11 | |
| 1-OCTADECENE | C18H36 | 314.82 | 14 | 90 |
| 1-NONADECENE | C19H38 | 329.10 | 23 | |
| 1-EICOSENE | C20H40 | 342.40 | 26 | |

These varying factors and fuel requirements call for flexibility in the compositions of diesel fuels. In an aspect, the LG2F Process is tailored to the production of diesel blendstocks. As used herein, the term "diesel blendstock" refers to a formulation comprising n-paraffins, iso-paraffins, cyclo-paraffins, olefins and aromatics having 9 to 24 carbons. The diesel blendstocks preferably have 10-20 carbons preferably have less than 35 wt % aromatic hydrocarbons, and more preferably less than 30 wt %. The following discussion further demonstrates the ability to tailor the LG2F Process depending on the C2-5 feedstream and the desired diesel product(s).

This invention can be tailored by isolating the LG2F R2 chemical reaction to convert $C_2$-$C_5$ light olefin-rich feedstocks into any range of $C_9$ to $C_{24+}$ middle distillate hydrocarbons used in jet fuel/kerosene, heating oil, marine gasoil, and ideally for high-value diesel fuel blending. When using olefin-rich feedstocks from any source with the LG2F R2 reactor for producing diesel fuel blendstocks, the zeolite-based chemical reaction produces a broad-spectrum of paraffin, iso-paraffin, cycloparaffin, olefin and aromatic output in a normal (gaussian) distribution. The distribution of the final product can be widened (e.g. $C_9$ to $C_{24+}$) or narrowed (e.g. $C_{10}$ to $C_{17}$) depending upon the desired performance characteristics of the middle distillate blendstock.

For example, one embodiment targets the LG2F finished product yield by setting the operating conditions to produce hydrocarbons up to the upper boiling limit of n-hexadecane for example 295° C. and recycling all byproducts in the flash drum with boiling points just above $C_9$ n-nonane at for example 145° C. This will yield a very high cetane blendstock with limited need for dewaxing. This can be a very useful premium diesel fuel blendstock, particularly if processed in the absence of any sulfur contaminates (e.g. using the optional $C_2$-$C_5$ light gas feeds from any hydrotreated alkane streams). The lower carbon paraffins have low freezing points which improve fuel flowability in cold weather (pour point). Many other LG2F R2 operating conditions may also be modified to optimize the fuel performance characteristics (e.g. cetane, pour point, density, heat of combustion, thermal stability, etc.) of the LG2F final product as a fuel blendstock in comparison with other possible middle distillate blending components. The LG2F R1 and R2 reactions can be used together in a recycle loop or independently depending upon the availability of the alkane or alkene light gas feedstreams. Assessing the middle distillate product requirements in relation to the feedstream quality available will determine the targeted operating conditions and product yields from LG2F processing. Table 8 depicts the varying range of carbon numbers that would include n-paraffin, iso-paraffins, cyclo-paraffins, olefins and aromatic compounds found in the middle distillate fuel. Using the operating conditions to select the upper boiling point and lower boiling point directly impacts the resulting cetane values, melting point and flowability attributes of the all-hydrocarbon blendstock. Selecting 3 ranges of carbon numbers C9-C14 results in excellent low-temperature flowability characteristics, selecting C10-C20 has a lower cetane value, selecting C12-C16 is a boutique diesel fuel blend with very high cetane values.

TABLE 13

Targeting C9-20 Paraffins, Olefins & Aromatics

| Carbon # | Broad Spectrum | Low Temp Flowability | Custom Blend | High Cetane |
|---|---|---|---|---|
| 9 | X | X | | |
| 10 | X | X | X | |
| 11 | X | X | X | |
| 12 | X | X | X | X |
| 13 | X | X | X | X |
| 14 | X | X | X | X |
| 15 | X | | X | X |
| 16 | X | | X | X |
| 17 | X | | X | |
| 18 | X | | X | |
| 19 | X | | X | |
| 20 | X | | X | |
| 21 | X | | | |
| 22 | X | | | |
| 23 | X | | | |

In one embodiment, the LG2F Process is tailored to produce a narrow range of C9 to C14, high-cetane paraffins with few low-melting compounds, thereby minimizing any need for dewaxing. This product is a desirable diesel fuel blendstock due to its speed of starting, clean combustion and low temperature flowability.

Examples—Diesel Blendstocks

This same fully-recycled LG2F Process can be operated at conditions to produce any targeted range (e.g. $C_{9+}$) of hydrocarbons for use as middle distillate, marine fuel, jet fuel or for diesel fuel blendstocks. The Thermal Olefination reaction depending upon the feed content creates a spectrum of $C_2$ to $C_5$ olefinic hydrocarbons, and the zeolite-catalyzed R2 reactor(s) uses operating conditions, particularly a low-pressure R2 reaction followed by a high-pressure R2 reaction sequence with recycling, which favor the $C_9$ to $C_{24+}$ range of hydrocarbon compounds used in diesel fuel blendstocks largely via the dimerization, trimerization, etc. of reacted C2-C5 olefin compounds. Selecting the $C_2$ to $C_8$ range of molecules output from the R2 catalytic reaction for recycle or aromatic reuse, and setting the appropriate operating conditions (T, P, WHSV) allows a tailored outcome of middle distillate with high cetane and low pour point values ideal for diesel fuel blendstocks. Byproducts of the reaction include methane, hydrogen and aromatic surplus.

In one embodiment, the R2 feedstream is comprised of ≥60% m/m ethene and is subjected to a high-pressure, low-temperature catalytic reaction just above activation energy to allow additional thermodynamic control over the reaction. This embodiment utilizes an integrated cooling/dilution mechanism and/or a deactivating agent to minimize the exothermic reaction.

In one embodiment, the R2 feedstream is comprised of ≥40% m/m ethene and ≥10% propene and is subjected to a high-pressure, low-temperature catalytic reaction just above activation energy to allow additional thermodynamic control over the reaction. This embodiment utilizes an integrated cooling/dilution mechanism and/or a deactivating agent to minimize the exothermic reaction.

In one embodiment, the R2 feedstream is comprised of ≥50% m/m any C2/C3 olefins and is subjected to a high-pressure, low-temperature catalytic reaction just above activation energy to allow additional thermodynamic control over the reaction. This embodiment utilizes an integrated cooling/dilution mechanism and/or a deactivating agent to minimize the exothermic reaction.

In one embodiment, the R2 feedstream is comprised of ≥50% m/m any C3/C4 olefins and is subjected to a high-pressure, low-temperature catalytic reaction just above activation energy to allow additional thermodynamic control over the reaction. This embodiment utilizes an integrated cooling/dilution mechanism and/or a deactivating agent to minimize the exothermic reaction.

In one embodiment, the R2 feedstream is comprised of ≥50% m/m any C3-C5 olefins and is subjected to a high-pressure, low-temperature catalytic reaction just above activation energy to allow additional thermodynamic control over the reaction. This embodiment utilizes an integrated cooling/dilution mechanism and/or a deactivating agent to minimize the exothermic reaction.

By-Products

In all LG2F embodiments, excess methane and hydrogen are byproducts of the Thermal Olefination reaction. Since methane and hydrogen are unreactive to the LG2F process, there is no restriction on their being present in the light hydrocarbon gas feedstream.

The LG2F Process will produce varying amounts of methane (e.g. 5-20%) subject to operational and economic choices, which may have utility as process fuel particularly in remote operating locations or returned for credit as dry gas to pipelines or refineries. Depending upon the C2+ feedstock quality, the LG2F process provides the option of extracting excess methane and hydrogen via membrane separation. Byproduct methane can also be recycled via MTO to maximize finished product yields from a given light gas feedstream.

Produced H2 is highly desirable if reusable as a byproduct, particularly in refining and petrochemical applications. If membrane separation is not feasible then a purge stream of the same composition as the recycle loop can be drawn to prevent byproduct accumulation.

Middle Distillates—R2

Low-Pressure/High Pressure Catalytic Reaction

The LG2F catalytic reaction sequence can also be configured to combine a low-pressure and high pressure reaction sequence to target the conversion of light olefinic gases (e.g., $C_2$-$C_5$) from the Thermal Olefination reaction, to chemically transform into longer-chain components through intermediary low-molecular coupling. This pressure and conversion control method produces high-grade distillates used particularly in middle distillates, jet fuel and diesel fuel blendstocks with added quality control by utilizing a high-pressure catalytic reaction sequentially following a low-pressure catalytic reactor.

In one such embodiment, the R1 Thermal Olefination reaction occurs upon receipt of alkane-rich $C_2$ to $C_5$ light gases at high temperatures (e.g., above 700° C.) operating at low pressure (e.g., 0-200 psig) and producing a $C_{2+}$ olefin-rich mixed gaseous yield. These gases are cooled and proceed to the initial R2 catalytic reactor which operates at temperatures between about 200-500° C. and low pressure (e.g. 0-200 psig) to avoid using expensive compression techniques. Using R2 with a WHSV above 30 and a residence time <1.0 second produces many molecular combinations (dimers, trimers, etc.) in the R2 gas-phase effluent.

Figure 9:
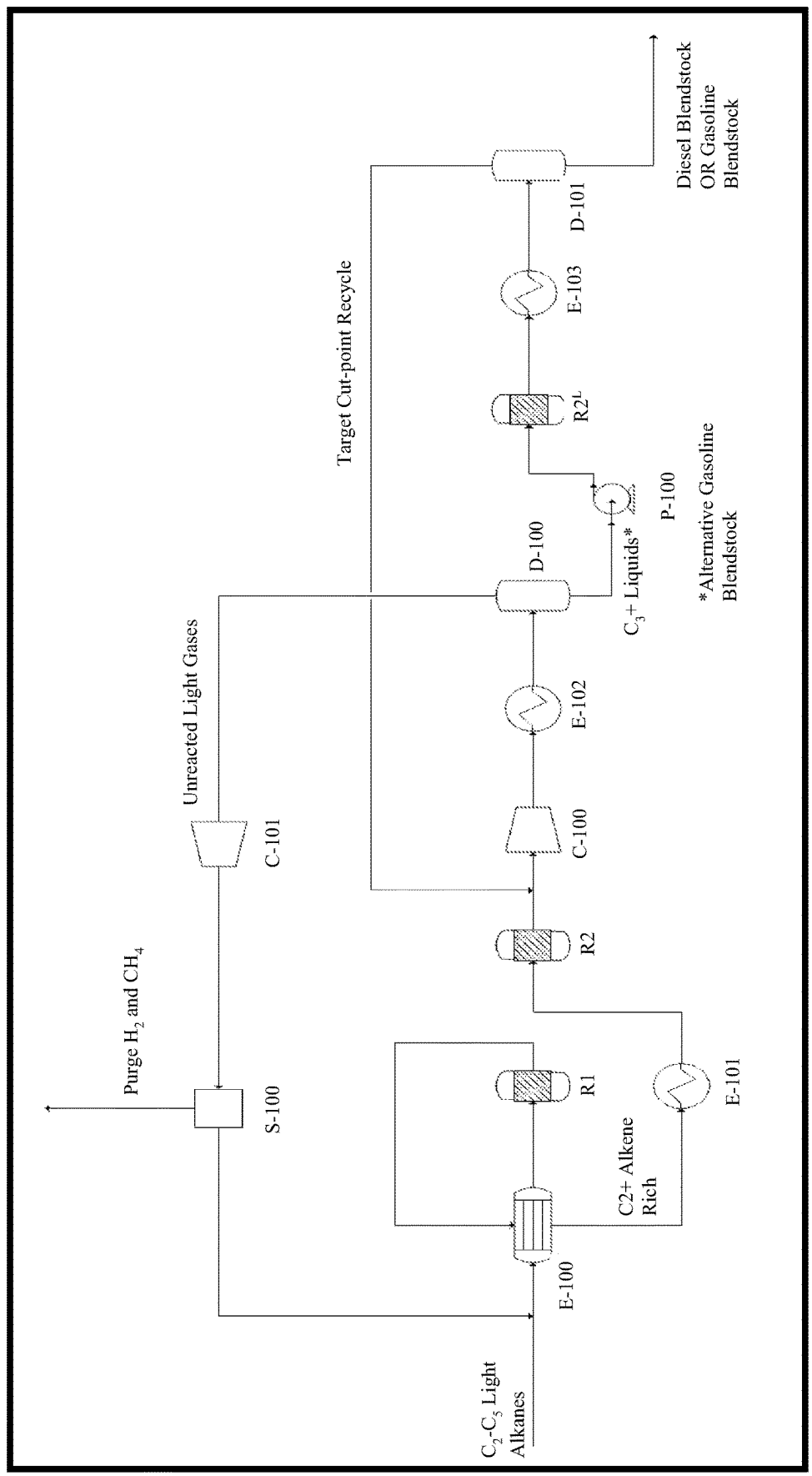
FIG. 9 is a flow diagram of an alternate embodiment of the LG2F Process including a series of zeolite-catalytic R2 reactors.

A compressor is utilized downstream of R2 and the pre heat-exchanger to compress the gas phase effluent into a phase separation flash drum whereby condensed liquids are captured, methane and hydrogen are separated or purged, and $C_2$-$C_{4+}$ residual light gases are recycled back to R1. The liquid phase from R2's condensed effluent, which comprises C4+ hydrocarbons (a marketable low grade gasoline product), can be further pressurized by a pump operating at from 100 to 1000+ psig for processing into another zeolite-catalytic reactor R2. This secondary R2 reactor (depicted as R2L in the graphics) operates at similar temperatures (e.g. 150-300° C.) and uses a zeolite catalyst which may be the same or different as used in initial R2 reactor, but in a high-pressure environment, resulting in a high concentration reaction. This high concentration reaction maximizes long-chain molecule formation (e.g., $C_{8+}$ which are ideal for various middle distillates). The resulting R2 reactions from the secondary reactor produce an effluent which then undergoes vapor/liquid flash drum separation to remove C4 and lighter gaseous components for recycle back upstream of R2, and yields performance grade diesel fuel or targeted $C_6$-$C_{10}$ gasoline blendstocks. This low-pressure/high-pressure catalytic method provides a more controllable coupling of light olefinic gases to produce longer-chain molecules thereby enhancing the tailoring of middle distillates, particularly those used in any targeted range of $C_9$ to $C_{16+}$ diesel fuel blendstocks or tailored gasoline blendstocks. See FIG. 9.

Similar to the previously described two-reaction (R1 and R2) sequence, there also exists an acceptable configuration for R1 plus two R2 zeolite reactions operating in series with a low and high-pressure configuration for increased molecular concentration thereby improving longer-chain hydrocarbon yield, suitable for middle distillates, especially diesel fuels.

The R1 feedstream is similarly comprised of the indicated C2-C5 light alkane components that render the process productive. These alkanes are combined with recycled light alkanes that are unreacted or formed downstream. A combined feed is then preheated in a heat exchanger (E-100) with the recycled gas outlet from R1 and then fed into the Thermal Olefination reactor (R1). R1 has operating conditions similar to previous embodiments where this high temperature reaction is conducted between 600 and 1100° C. and 0-1500 psig. R1's products consist of thermally dehydrogenated alkenes that are suitable for the next iteration of reactions. The outlet of the reactor has integrated heat with E-100 as described during heat exchange previously. It is expected that the stream will need to be further cooled after cross exchange before entering the Zeolite-Catalytic reactor (R2). E-101 will further cool the stream to an appropriate operation temperature and pressure for R2. R2 operates to largely dimerize, trimerize, and tetramerize the incoming olefinic components to produce a partially condensable stream at high pressure.

The R2 effluent is then combined with a recycle stream originating downstream in the final flash drum (D-101). There should be enough suction head from C-100 to return the compressed gas from the downstream drum otherwise additional compression may be necessary. The combined stream is then compressed to a pressure resulting in some initial liquification of C3+ components (200-1000 psig) that are then further liquified in a cooler (E-102). It shall be appreciated that further heat integration can occur to increasingly preheat the feed into the first reactor as the temperature will notably increase post compression. A flash separator (D-100) is used to remove any vaporous light alkanes that can be further processed by R1. The light alkane stream that contains mostly ethane, propane, methane, and hydrogen is fed into a compressor (C-101) to ensure consistent flow through the recycle loop. C-101 may be unnecessary depending on operating conditions and this high-pressure gas may have enough head to proceed through the loop unaided before being stepped down with a valve. The outlet of C-101 is led into a separator (S-100) where it can either be simply purged or passed through a membrane(s) to remove methane and hydrogen byproducts. After mass removal the first recycle loop is then fed back upstream in the process.

The high-pressure liquid of D-100 is pumped (P-100) to very-high-pressure (>1000 psig) as a liquid to mitigate the need for expensive very-high-pressure compression. This very-high-pressure liquid is fed into a third reactor (R2L) where the liquid is vaporized and further oligomerized to heavy molecular weight components. A heated expansion chamber pre-R2L may be needed to ensure appropriate vaporization. Heavy molecular weight production under this pressure will result in a largely condensed stream down-flow of the third reactor. This heavy molecular weight stream exiting the third reactor is then cooled in E-103 where it is further cooled/liquified to a temperature that is appropriate for vapor/liquid separation. D-101 separates the unliquified gases that may contain some mid-range olefinic components. Regardless of alkane/alkene composition, the tops of D-101 are fed upstream to be re-compressed, cooled, and separated. Any recycled byproducts downstream that are C2 or less will consequently be recycled through the initial recycle loop. Finally, a liquid stream is recovered from D-101 that resembles a diesel or gasoline spectrum product produced via a three-reactor, pressure swing process for very-high-pressure and high concentration oligomerization.

In a related embodiment, a source comprising about 70% ethane gas can be processed in the R1 Thermal Olefination reactor to primarily produce ethylene which is then processed in R2 at low pressure with a fast residence time to create dimers, trimers and tetramers from the olefin-rich feedstream. The exiting light gases are then cleaved away for recycle and the remaining C4+ liquid, a low-grade natural gasoline product, is available for the next processing step. The R2 liquid effluent from the low-pressure reaction may optionally serve as a finished product in this example with higher value than ethane, or it may be further processed as a pressurized liquid at high concentration into the secondary R2 reactor where longer-chain coupling occurs. The high molecular concentration in the liquid phase and the low residence time of the secondary R2 reaction produce a premium grade distillate for use in diesel fuel blendstocks or targeted gasoline blendstocks. The unused compounds from R2 are recycled based upon targeted hydrocarbon cut-points and moved upstream of the liquid/gas condenser and the liquid pump. Unprocessed light gases from R2 are recycled back to R1 and methane and hydrogen are purged for reuse.

In a similar embodiment, a low-value ethane/propane mixture is processed into R1 and the same options and features of the invention result in either $C_{5+}$ gasoline grade fuel blendstocks (from R2) and/or high-performance distillate (from a secondary R2 reactor) which can be targeted to produce any range of fuel grade molecules, e.g., $C_9$ to $C_{16+}$ for use in diesel fuel blendstocks or targeted gasoline blendstocks. In processing R2 for diesel fuel, the $C_8$ and lighter pressurized stream is recycled for reprocessing. The light compounds from R2 are recycled, and the byproduct methane and hydrogen are purged for reuse.

In another embodiment, any two R2 reactors performing in series can be operated at the same pressure as R1 Thermal Olefination with intermediary separation of light gases. This will increase the concentration of hydrogen and methane in the gaseous stream for easier membrane separation or less yield loss from purge. Generated byproducts in the second R2 catalytic reactor can then be recycled directly into R1 without removal of unreactive hydrogen and methane since they will be unremarkable in stream composition.

In an environmentally distinct embodiment, a modification of the gas phase reaction of R2 can be conducted as a very-high-pressure liquid or supercritical phase reaction (>500 psig) to even further increase its concentration past that of high-pressure gas.

Configurationally, the LG2F system can also operate with multiple R1 Thermal Olefination reactions and a single R2 catalytic reaction. Stepping temperature up and down from the first R1 to the second R1 will give more selective control of olefinic product distributions and also serve to limit heavy coking of a single R1 reactor system.

A further embodiment is the LG2F process is a multi-stage R1 configuration and multi-stage R2 catalytic reactions with low/high pressure optionality to produce a more optimized product distribution and yield. These two-, three- and four-step LG2F reactor designs may utilize any commercially viable process technique known in the art (e.g. fixed bed, moving bed, or fluid bed) embodied herein allow for the interchangeable production of C4-C12 gasoline blendstocks and/or C9-C16+ diesel fuel blendstocks from alkane-rich light gases.

The LG2F process conditions are easily convertible to switch processing methods which offers a unique capability to adjust the production of key transportation fuels depending upon ever-changing market conditions. A particular feature of the LG2F process is the option to produce gasoline blendstocks at one set of operating conditions and/or switch to produce middle distillate blendstocks at a different set of (R2) reactor operating conditions. Depending upon the availability of downstream processing often available at refining plants, the timing of the process switching can be tailored using distinctive cuts to eliminate the need for any distillation of the blendstocks.

In one embodiment, the process is solely devised to produce middle distillate grade product blendstocks of a high cetane and net heat value. In a different embodiment, the process is solely devised to produce higher octane gasoline blendstocks. In yet another embodiment, the process is set to produce higher octane gasoline blendstocks during one period, then switched and reconfigured to produce middle distillate blendstocks in another period. In yet another embodiment, the process is set to produce a full spectrum of, for example, $C_{5+}$ or $C_{6+}$ or $C_{7+}$ fuel products which could be distilled downstream for different commercial uses. Once again, the preferred end product of the reaction (e.g., the targeted performance requirements of a fuel blendstock) may have a determining factor on the ideal operating conditions (T,P,WHSV) and choice of the R2 catalyst.

While the diesel fuel blendstocks described as the products of LG2F in this invention may be comprised of varying chemical compounds, targeted performance grade diesel fuels can be tailored by feed characteristics, catalyst choices and operating conditions to achieve a minimum set of performance conditions for diesel grade products.

In one embodiment, the diesel fuel product is ≥40 cetane number, with aromatic content ≤35% m/m, satisfactory cloud point and cold temperature flowability, lubricity ≤520 microns at 60° C., and distillation temperature ≤338° C. at 90% point.

In one embodiment, the diesel fuel product is ≥50 cetane number, with aromatic content ≤35% m/m, satisfactory cloud point and cold temperature flowability, lubricity ≤520 microns at 60° C., and distillation temperature ≤338° C. at 90% point, In one embodiment, the diesel fuel product is ≥55 cetane number, with aromatic content ≤35% m/m, satisfactory cloud point and cold temperature flowability, lubricity ≤520 microns at 60° C., and distillation temperature ≤338° C. at 90% point.

Another distinguishing feature of the LG2F process is that the composition and performance characteristics of the C9+ distillate products do not require a hydrogenation step. However, some tailored fuel applications may favor a more paraffinic composition in which case a hydrogenation reaction is included as an optional embodiment. In this case, hydrogen can be supplied by the LG2F process. In the case of excess hydrogen from the LG2F process, the hydrogen byproduct may be highly valued by other markets, e.g. refining.

The LG2F process also offers a wide range of modular configurations (e.g., to eliminate benzene or increase octane or increase energy density or increase net heat of combustion or lower vapor pressure) when processing C2 to C5 light gases which allows for the tailoring of the operating conditions resulting in a specified composition of gasoline blendstock. In one embodiment, the LG2F R1+R2 reaction with recycling is specified to produce only C7 to C10 aliphatic and aromatic hydrocarbons between the boiling point range of 85° (above benzene) up to 200° C. This results in a well-balanced high-octane gasoline blendstock with no benzene. In another embodiment, the LG2F R1+R2 reactions with recycling is specified to produce C5 to C10 aliphatic (favoring paraffins and olefins) with virtually no aromatics. This results in a lower octane blendstock, but with higher volumetric yields. In another embodiment, the LG2F R1+R2 reaction is specified to produce primarily C7 to C10 high octane aromatics with only a minor content of aliphatic hydrocarbons. This results in a high-octane gasoline blendstock, in the absence of benzene, and a high energy density.

This modular functionality in designing tailored hydrocarbon product streams from C2-C5 light gas streams is a major feature of this invention. This tailoring can be applied to adjust to ever-changing market conditions and locational arbitrage opportunities. The LG2F R1 and R2 reactors can operate independently or in an integrated fashion. Any available source of olefins can be used in the R2 reaction once the feedstock composition is assessed for the ideal temperature, pressure and reaction time for a given product specification. The product high (final) boiling point is specified by the R2 operating conditions and the product low (initial) boiling point is set by the flash drum cut point which eliminates any need for distillation.

Combining R1 Thermal Olefination with an R2 Reactor

There is an added feature of this invention to combine the benefits of Thermal Olefination and the basic Oligomerization, Dimerizing and Trimerizing features of R2 into a single catalytic reaction. This bi-functional reaction feature is called an "Oli-Par" process whereby a single reactor produces an olefin and paraffin cocktail which can be separated using knockout techniques described herein. The olefins can pass to a downstream R2 reactor(s) to complete the conversion to distillate fuels while the paraffins can be used as high-quality gasoline or aromatic products. This bi-functional reactor process reduces costs and allows operational flexibility for the producer of gasoline and distillate types fuels, particularly for those who may prefer to produce more than one finished product. A key advantage of the Oli-Par process is operating temperatures of the catalytic reaction are generally 500 C to 750 C thereby reducing some of the operational severity of the Thermal Olefination process that may otherwise harm certain catalysts.

In one embodiment, the Oli-Par process receives feedstreams comprised of at least 90% C2+ alkanes, operating at 600 C with a light gas (<C4) recycle loop to produce a cocktail comprising ≥C4+ olefins and ≥C8+ paraffins. Following a targeted knockout step, the C4+ olefins are then passed to a downstream R2 reactor for further processing to produce longer-chain distillate fuels. Depending upon the tailored cut, any C6+, C7+ or C8+ paraffins can be used for gasoline blendstocks, fuels and/or aromatic uses. The proportion of olefins to paraffins can vary depending upon the operating conditions of the Oli-Par process. A simple liquid/vapor knockout separator is used to separate the two constituent product types which do not need to be of high purity for fuel uses. In some embodiments, the use of hydrogen (H2) as a feed to a secondary R2 reaction can increase the performance characteristics of the distillate fuel products by increasing cetane values of the fuel.

Combining Refinery Processes and LG2F

Figure 10:
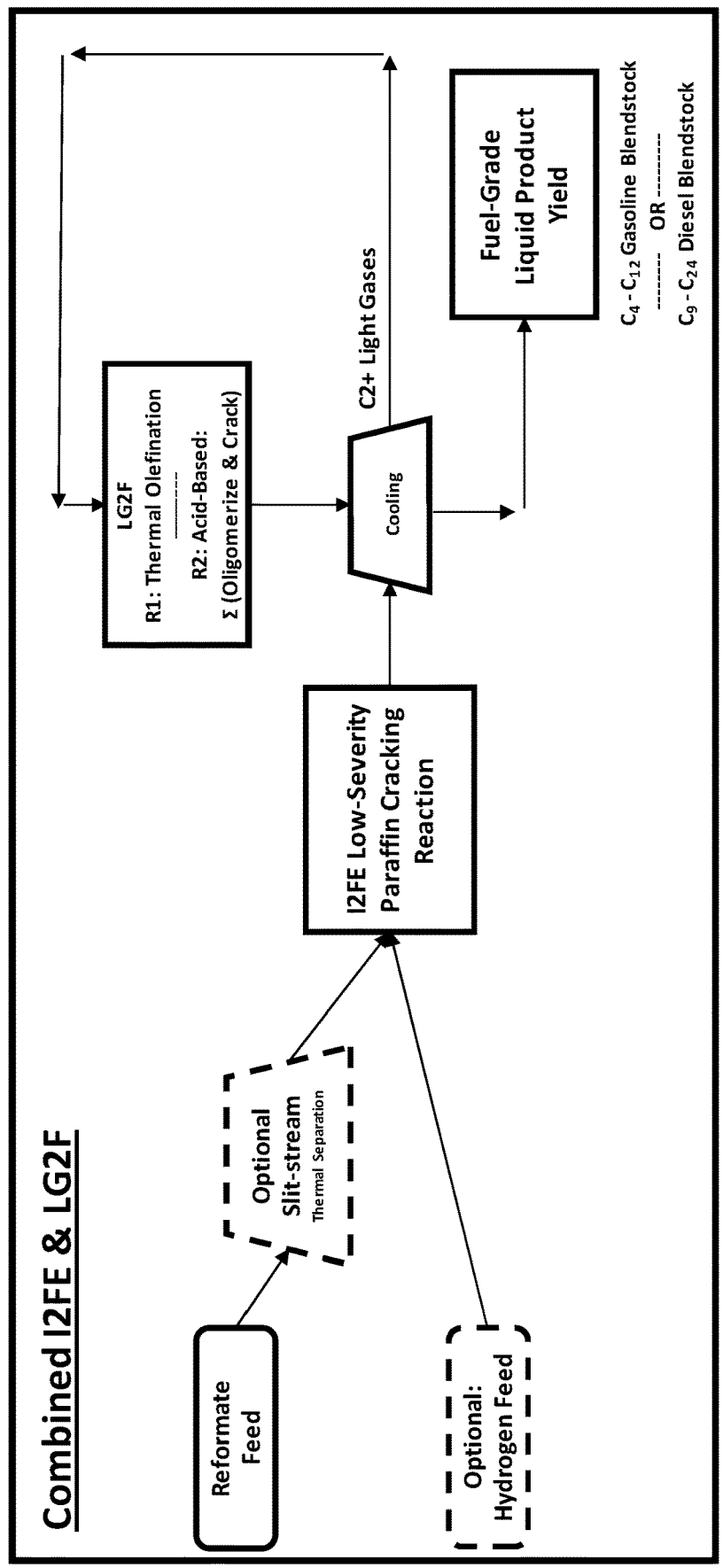
FIG. 10 is a flow diagram of an alternate embodiment of the LG2F Process including a combination with light gas feedstreams from refining processes.

Another aspect of the LG2F Process is the ability to combine the process with any other hydrocarbon process which provides a source of C2-5 hydrocarbons useful as a feed to the LG2F Process. In addition to the light gas offtake from NGL plants (e.g. demethanizers), this could include the light gas byproducts from a catalytic reforming, hydrodealkylation, paraffin cracking, fluid catalytic cracking (producing olefin byproducts), a coking unit, or any similar example with sufficient access to C2-C5 light hydrocarbons, (One such process is described in a co-pending application, U.S. Ser. No. 16/242,465, also owned by Applicant. This process is called "I2FE" and comprises a long-chain paraffin cracking technique that generates C2+ byproducts as a feedstream to LG2F. This combined process is presented in FIG. 10.)

In one combined embodiment, a paraffin cracking process (I2FE) can be designed to consume a small amount of hydrogen to maintain the longevity of the metal catalyst. Depending upon design configurations, hydrogen byproduct from LG2F may offset on-purpose hydrogen consumed in I2FE, if these two processes are used together. The design of both units can be balanced and optimized to be hydrogen natural or a net producer of hydrogen, depending upon the needs of the business operation.

In another combined embodiment, the LG2F Process converts the clean light gas compounds (typically C3+) specifically from any appropriate refining process to produce C6+ blendstocks using Thermal Olefination (R1) followed by a multi-iterative, acid-catalyzed cracking, oligomerizing and/or cyclizing reactions (R2) in a single or multi-bed reactor configuration with a recycle loop. In another embodiment from a catalytic reformer, the process is used to yield any range of $C_9$ to $C_{24+}$, zero-sulfur, middle distillate compounds with effective performance properties for use in diesel fuel and other transportation fuel blendstocks. The same process can be performed targeting a narrower range of middle distillate compounds such as $C_{10}$-$C_{20}$, or $C_{12}$-$C_{18}$, or $C_9$-$C_{14}$, etc. depending upon the performance requirements of the finished product. A byproduct of this process depending upon the configuration is unused hydrogen, methane and surplus aromatics.

Another embodiment of this LG2F invention converts the clean light gas compounds ($C_2$+) specifically from the I2FE process, with or without reformer off-gases, to produce gasoline range blendstocks using only Thermal Olefination and a multi-iterative acid-catalyzed zeolite reaction oligomerization, cyclization and cracking reaction in a single or multi-bed reactor configuration with a recycle loop. This process is designed to handle excess hydrogen to yield any $C_4$ to $C_{12}$ range gasoline compounds (i.e., paraffins, olefins and aromatics) for use with other gasoline blendstocks. All gasoline products in this embodiment are very-low benzene, sulfur-free and nitrogen-free. A byproduct of this process depending upon the configuration is unused hydrogen, methane and surplus aromatics.

Another embodiment of this LG2F invention converts the clean light gas compounds ($C_2$+) specifically from the I2FE process to produce gasoline range blendstocks using thermal cracking (R1) and multi-iterative, acid catalyzed reactions (R2) in a single or multi-bed reactor configuration along with a recycle loop. This process is designed without excess hydrogen to yield $C_4$ to $C_{12}$ range gasoline compounds (i.e., paraffins, olefins and aromatics) for use with other gasoline blendstocks. All gasoline products in this embodiment are sulfur-free and nitrogen-free. Alternatively, this process is designed to provide excess hydrogen for reuse. Depending upon the configuration, methane and surplus aromatics may be byproducts of the reaction.

Direct Alkene Feeds

The LG2F Process is also useful with other sources of the C2-C5 alkenes processed in the catalytic reactor (R2). For example, FCC cat-cracked gasoline byproducts including C3 alkenes and LPG can be utilized as feedstocks directly into the catalytic reactor of the LG2F Process. Another source comes from any methane activation process, such as oxidative coupling of methane, or methane pyrolysis and hydrogenation of acetylene, or any other technique known in the art to produce ethene from methane. The presence of greater than about 20% alkenes in the light hydrocarbon feedstock allows the use first of the zeolite-catalyzed R2 reaction in the LG2F process. The unconverted paraffins are then recycled to the Thermal Olefination reactor (R1).

Figure 11:
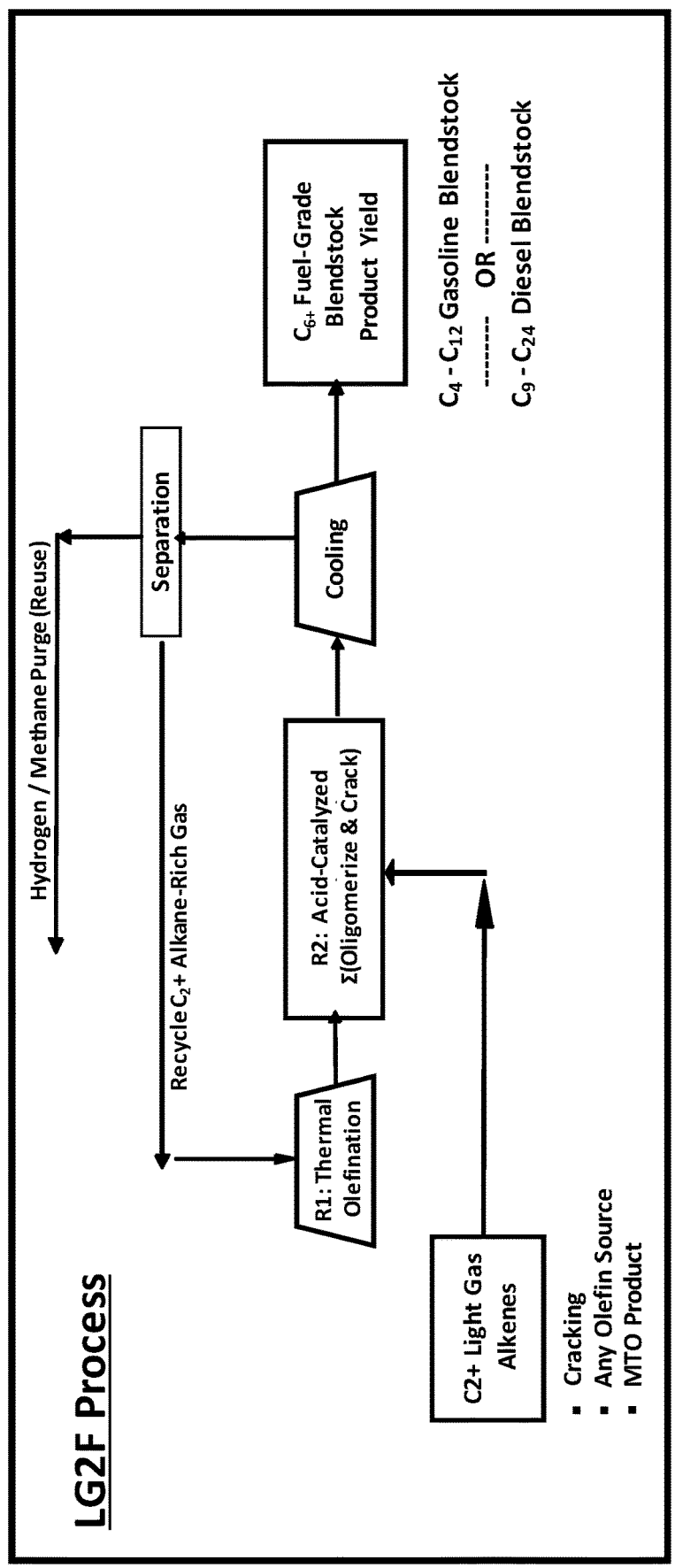
FIG. 11 is a flow diagram of an alternate embodiment of the LG2F Process including direct alkene feed to the zeolite-catalytic R2 reactor.

Referring to FIG. 11, the basic LG2F Process is shown. However, the Process is augmented by having the C2-5 alkene feed directed first into the R2 catalytic reactor, bypassing the Thermal Olefination reactor and going straight into the multi-iterative, acid-catalyzed reactions in a single or multi-bed reactor configuration with a recycle loop. This feedstream is processed as previously described to yield C6+ fuel-grade blendstocks. Light gases from the catalytic process (often containing $C_{3+}$ olefinic compounds, e.g., propylene) are then sent to the R1 reactor to proceed through the system as previously described, thereby producing additional gasoline range blendstocks. This process is designed to provide excess hydrogen to yield $C_6$ to $C_{11}$ range gasoline compounds (i.e., paraffins, olefins and aromatics) for use with other gasoline blendstocks. All gasoline products in this embodiment are very-low benzene, sulfur-free and nitrogen-free. A byproduct of this process is unused hydrogen.

Figure 12:
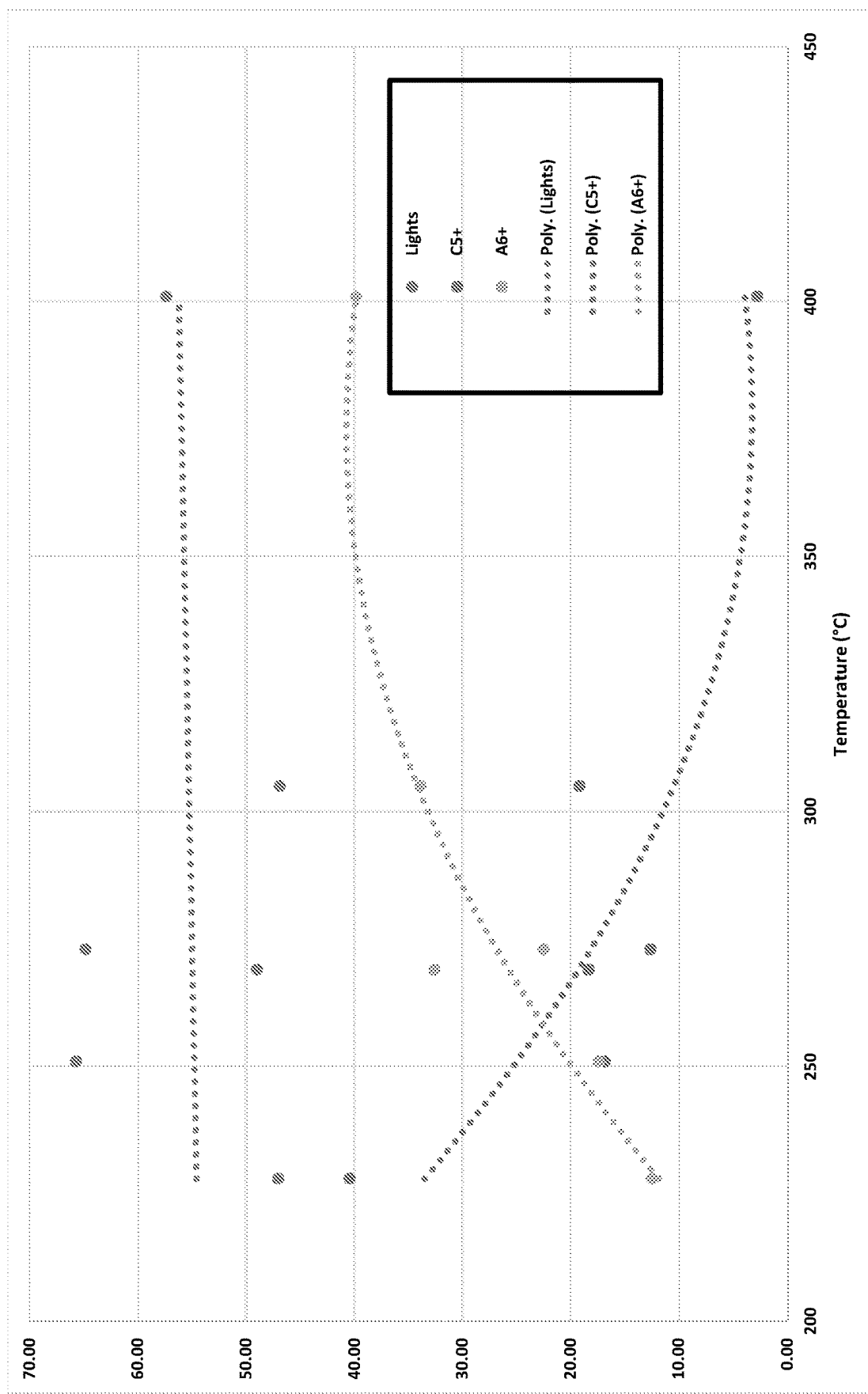
FIG. 12 is a graph showing a single pass yield of propene in accordance with the flow diagram of FIG. 11.

As an illustration of the processing of alkene gases, a single pass yield of the $C_{2+}$ acid-based chemical reaction, shown in FIG. 12, is from a C3 olefin feedstock and demonstrates the production of gasoline grade compounds. This reaction was made at 45 psig and 3 WHSV across a range of temperatures. As illustrated, the aromatic hydrocarbon content ($A_{6+}$) varied by the reaction temperature, which can be used to increase octane values of gasoline blendstocks.

Another embodiment of this LG2F invention receives the byproduct light gases from the catalytic cracking process (often containing $C_{3+}$ olefinic compounds, e.g. propylene) to produce diesel range fuel blendstocks. This embodiment again bypasses the initial Thermal Olefination and goes straight into the multi-iterative, acid-catalyzed reactions in a single or multi-bed reactor configuration with an R2 catalyst tailored for the feedstream before re-entering the LG2F recycle loop. This process is designed to provide excess hydrogen and to yield any specified range of $C_4$ to $C_{12}$ gasoline blendstocks or $C_9$ to $C_{24}$ middle distillate for use as diesel fuel blendstocks. A byproduct of this process is unused hydrogen.

The foregoing processes are examples of a range of processes using alkene feeds, further including the following:

$C_2+$ alkene gas streams exiting the catalytic cracking unit are transformed to $C_6+$ gasoline constituents first via LG2F chemical reaction (R2), followed by a recycle loop that restarts Thermal Olefination and a chemical reaction loop resulting in higher liquid gasoline yields;

$C_{2+}$ light hydrocarbon streams with primarily olefinic compounds are merged to increase the available volume of light gas compounds for conversion via R2 processing with recycle loops to R1+R2 to produce gasoline blendstocks using the LG2F process;

$C_{2+}$ light hydrocarbon streams with primarily olefinic compounds are merged to increase the available volume of light gas compounds for conversion to light gas oil or diesel fuel blendstocks using LG2F.

Reducing Benzene

Figure 13:
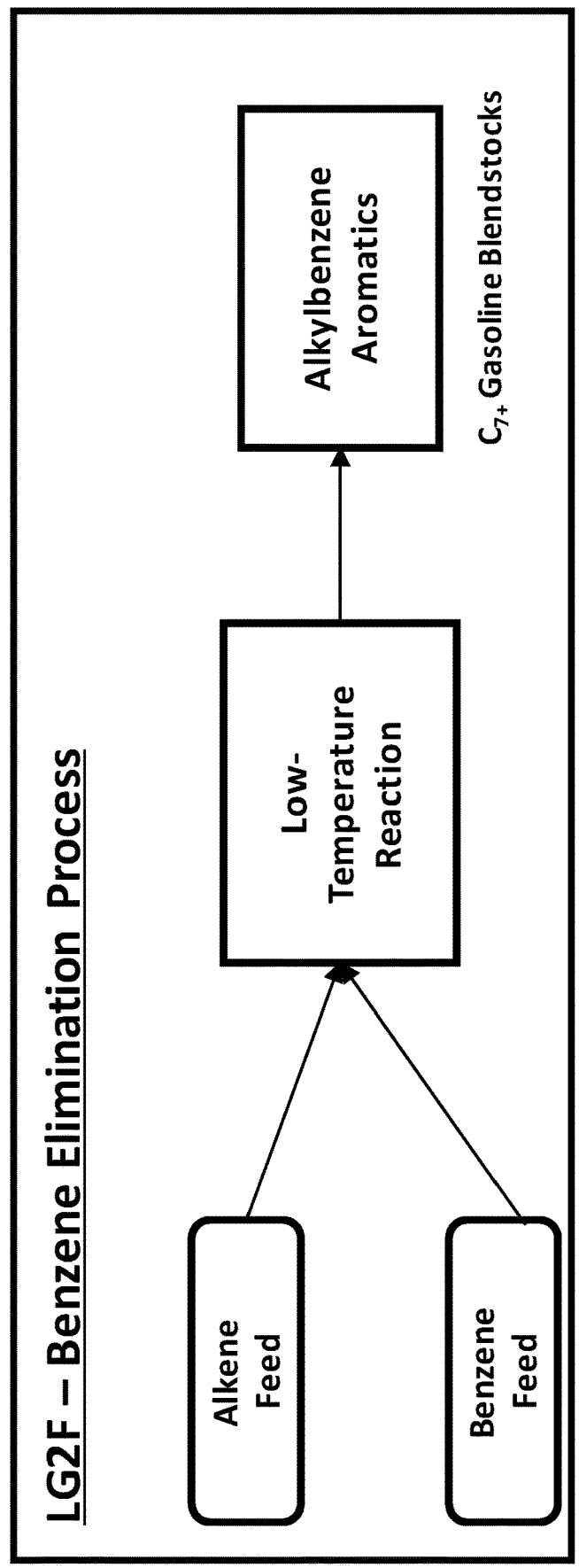
FIG. 13 is a flow diagram showing optimal elimination of benzene from gasoline blendstocks produced by methods herein.
Figure 14:
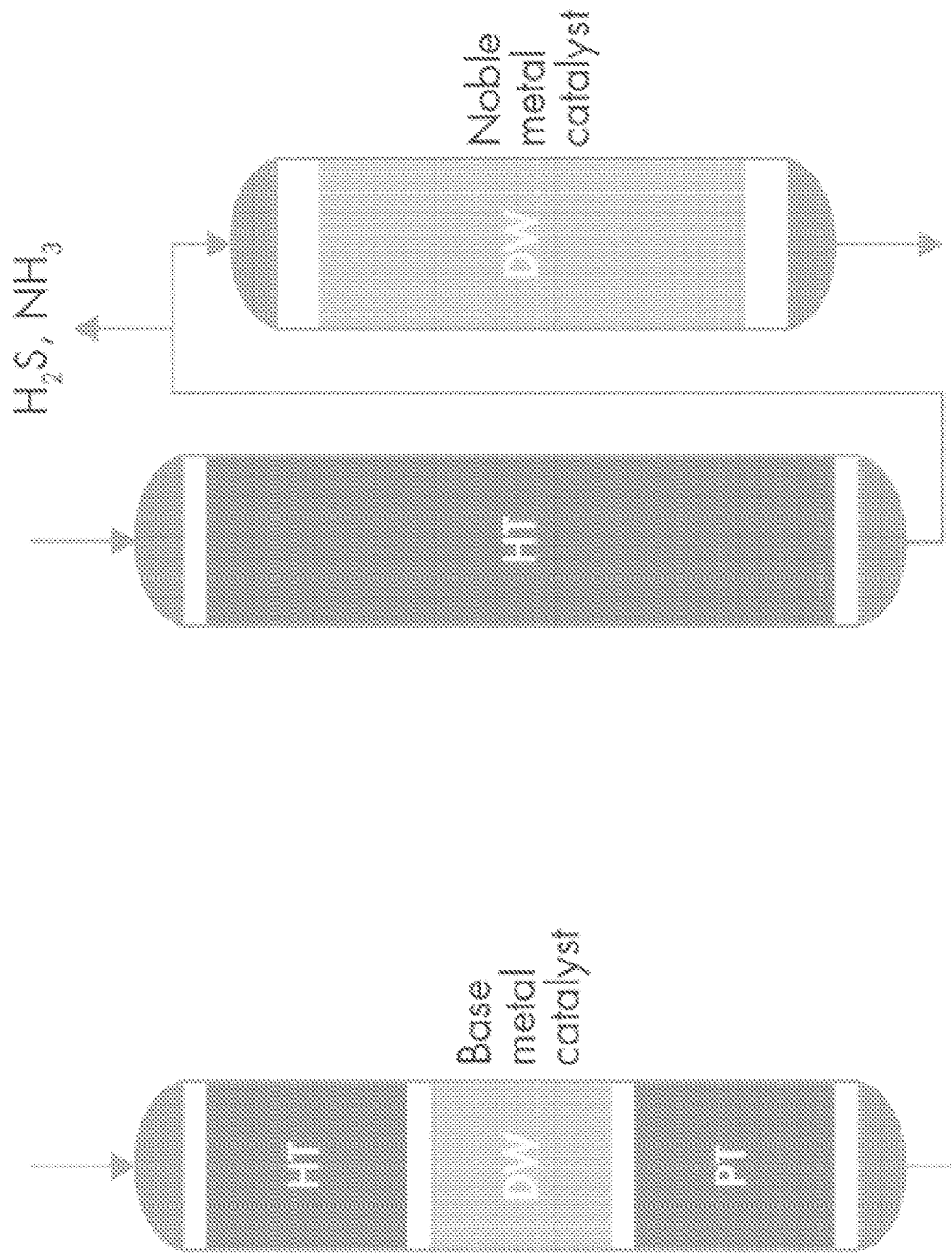
FIG. 14 is a diagram showing construction elements typical of single and dual reactors.
Figure 15:
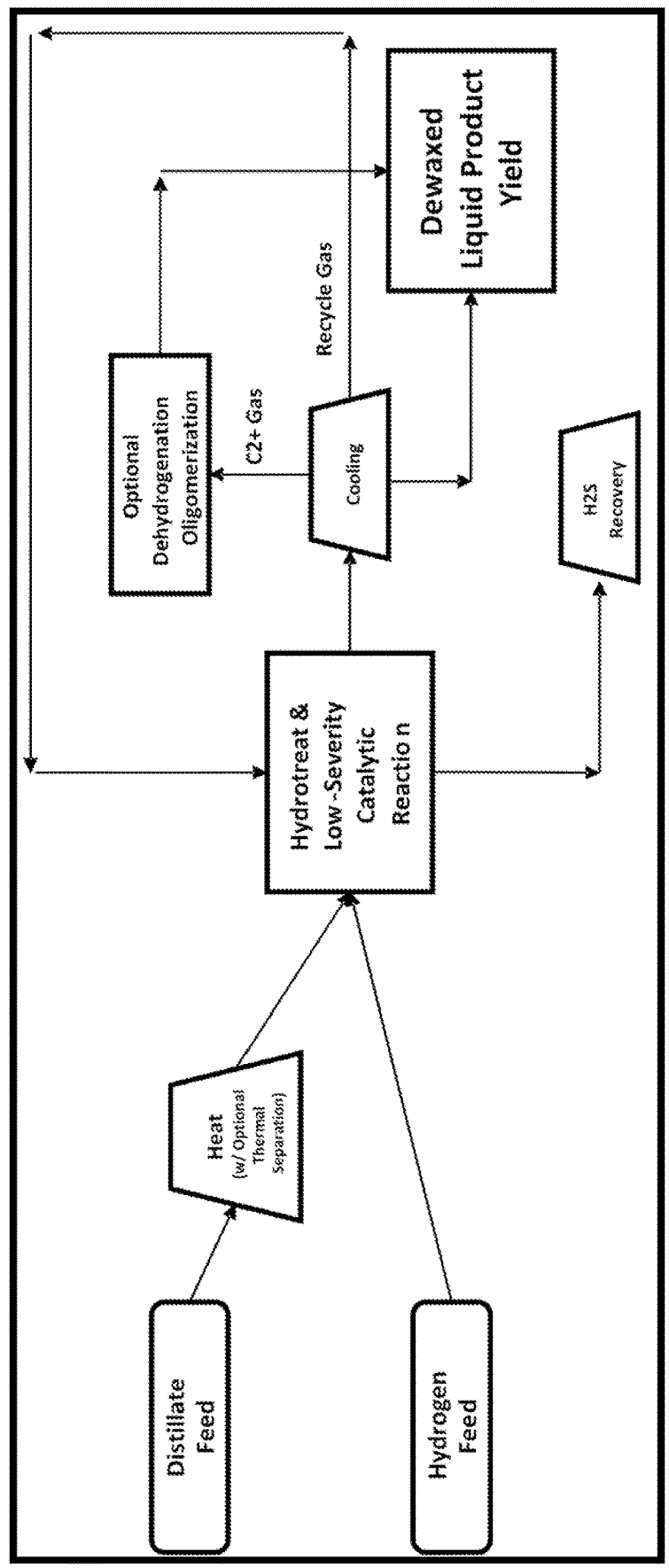
FIG. 15 is a diagram of a dewaxing process flow in accordance with the present disclosure.

Another major feature of this light gas transformation to transportation fuel is the selective reduction of benzene, which makes the resulting products excellent for gasoline blending due to low specification limits placed on benzene for use in fuels. In the case where there is an unwanted surplus of benzene-rich C6+ aromatics extracted by liquid-vapor knockout from the R1 Thermal Olefination effluent, an added feature of LG2F is to combine light alkene compounds (e.g. C2-C3) from the R1 reaction with the surplus C6+ aromatic compounds into a simple low-temperature acid-catalyzed reaction to create alkyl-benzenes. See FIG. 13. This processing will convert benzene via electrophilic substitution to become productive gasoline grade blendstocks that adhere to existing limitations in gasoline specifications for high-octane aromatic compounds. This process may utilize aluminum chloride and hydrogen chloride catalysts. This process will further increase the value of the gasoline blendstock.

Another aspect of this invention is a simplified method to dewax paraffinic compounds from $C_{14}$ to $C_{40}$ hydrocarbon streams using a single-stage, low-severity, acid-catalyzed reaction process to both hydrocrack and hydrotreat middle-to-heavy grade distillate feedstocks to produce a higher-value, higher-grade middle distillate with higher fuel performance properties.

Catalytic dewaxing is typically referred to as a process that selectively removes $C_{14+}$ paraffinic compounds from middle- to heavy-distillate hydrocarbon streams. This technology is usually applied to hydrocarbons used in diesel fuel and heating oils to improve its physical properties including cloud point, pour point and cold flowability. Increasing quality reduces the need of using fuel additives to improve properties and allows for more detailed control of blending specifications. The primary alternative technology to catalytic dewaxing is solvent based dewaxing which applies a solvent extraction method to heavy paraffinic compounds that preserves the chemical structure.

Configurations of traditional dewaxing units vary but are most often categorized in two categories: a single or dual bed reactor. The choice in configuration depends on preference for hydrotreating integration into the dewaxing catalytic system. The inlet streams have higher concentrations of sulfur and nitrogen which will deactivate noble metal catalysts. So, a hydrotreating bed is typically integrated before the dewaxing catalyst to ensure minimal degradation of performance.

Traditional Dewaxing Methods

Traditional refinery dewaxing catalysts are nickel- or platinum-based selective zeolites, which is a molecular sieve catalyst. By controlling pore size, these methods control the types of molecules that enter the catalytically active sites. Specifically, the pore sizes are set to allow n-paraffinic compounds but not isoparaffinic compounds (0.6 nm). Traditional hydrotreating catalysts commonly use Ni/Mo metal combination to perform the hydrogenation of nitrogen and sulfur-based compounds. The configuration of these catalyst depends on the level of protection needed in a dewaxing unit. If there are lower than normal catalyst poisons, then a single reactor can be used with a protective bed above the dewaxing bed. However, if poisons are an issue then a separate hydrotreating bed will be beneficial to sustained catalyst life. A comparison between typical single and dual bed catalysts is shown in Table 14.

TABLE 14

| Product distribution (wt %) | Single stage (SDD-800) | Second stage (SDD-821) |
|---|---|---|
| C1-C4 | 4.3 | 0.2 |
| C5-177° C. | 9.2 | 5.9 |
| 177° C.+ | 86.7 | 94.5 |
| Total | 100.2 | 100.6 |

Traditional methods for dewaxing require a separation between two catalytic beds with one performing hydrotreating and the other selectively cracking n-paraffinic compounds. Noble metal catalysts propose too high of a risk for poisoning from hydrogen sulfide and ammonia, hence the removal of these gases before dewaxing. However, base metal catalysts lack the activity needed to dewax a hydrocarbon stream effectively and require larger utility costs.

This invention utilizes a unique, low-severity method for hydrocracking the $C_{14}$- to $C_{40+}$ paraffins or any targeted range of n-paraffins compounds using a specialized zeolite catalyst with the capability to simultaneously hydrotreat the feedstream thereby removing the sulfur and nitrogen-based compounds and cracking the low-melting paraffins in a single step process. This unique method reduces total costs of processing and eliminates the need for additives used in the field. The main target is cracking broad scope n-paraffinic compounds since even n-tetradecane ($C_{14}$) melts above low ambient temperatures. Having even a single branch significantly reduces the melting point by ~80 F while still having a cetane value of 67.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected.

The invention claimed is:

1. A method for converting $C_{2-5}$ alkanes to a broad-range of fuel products constituting higher-value $C_{5-24}$ hydrocarbon fuels or fuel blendstocks, comprising:
   passing a fresh, $C_{2-5}$ alkane-rich feedstream through a thermal olefination reactor, the fresh, $C_{2-5}$ alkane-rich feedstream having any one or more of the $C_{2-5}$ alkanes and containing at least 90 wt % $C_{2-5}$ feed alkanes, the thermal olefination reactor operating without a dehydrogenation catalyst and without steam, the thermal olefination reactor converting the $C_{2-5}$ feed alkanes to product olefins in an effluent olefination stream;
   passing at least a portion of the effluent olefination stream to an oligomerization reactor containing a zeolite catalyst and operating at a temperature, pressure and space velocity to crack, oligomerize and cyclize the product olefins to form an effluent oligomerization stream comprising the fuel products, unconverted $C_{2-4}$ alkanes and methane;
   separating $C_{2-4}$ alkanes and methane from the effluent oligomerization stream;
   passing a recycle stream comprising the separated $C_{2-4}$ alkanes and methane from the effluent oligomerization stream directly back through the thermal olefination reactor,
   separating $C_5$ alkanes from the effluent oligomerization stream;
   passing a recycle stream comprising the separated Cs alkanes from the effluent oligomerization stream directly back through the thermal olefination reactor,
   the olefination reactor operating at a temperature, pressure and space velocity to convert at least 80 wt % of the $C_{2-5}$ feed alkanes to product olefins in the effluent olefination stream; and
   recovering the fuel products from the effluent oligomerization stream.

2. The method of claim 1 in which the effluent olefination stream undergoes membrane separation of inert gases.

3. The method of claim 1 in which the fresh, $C_{2-5}$ alkane-rich feedstream comprises 80-100% ethane and 0-20% propane.

4. The method of claim 1 in which the fresh, $C_{2-5}$ alkane-rich feedstream comprises at least about 90 wt % ethane.

5. The method of claim 1 and which further comprises passing a recycle stream comprising methane from the effluent oligomerization stream back through the oligomerization reactor.

6. The method of claim 1 in which the fresh, $C_{2-5}$ alkane-rich feedstream comprises at least 95 wt % $C_{2-5}$ alkanes.

7. The method of claim 1 in which the effluent olefination stream has at least 95 wt % of the $C_{2-5}$ feed alkanes converted to product $C_{2-5}$ olefins.

* * * * *